(12) United States Patent
Desmond et al.

(10) Patent No.: US 10,543,252 B2
(45) Date of Patent: Jan. 28, 2020

(54) REGULATING CALCIUM IN EXCITABLE CELLS WITH A NOVEL PROTEIN

(71) Applicant: University of Maryland, Baltimore, Baltimore, MD (US)

(72) Inventors: Patrick F. Desmond, Baltimore, MD (US); Robert J. Bloch, Baltimore, MD (US); Mark A. Rizzo, Nottingham, MD (US); Joaquin Muriel, New Freedom, PA (US); Michele L. Markwardt, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 15/016,086

(22) Filed: Feb. 4, 2016

(65) Prior Publication Data
US 2016/0228502 A1 Aug. 11, 2016

Related U.S. Application Data

(60) Provisional application No. 62/112,195, filed on Feb. 5, 2015.

(51) Int. Cl.
*A61K 38/17* (2006.01)
*A61K 31/7105* (2006.01)

(52) U.S. Cl.
CPC ...... *A61K 38/1709* (2013.01); *A61K 31/7105* (2013.01)

(58) Field of Classification Search
CPC ................................................. A61K 38/1709
See application file for complete search history.

(56) References Cited

PUBLICATIONS

Gokin et al. J cell Biol 2010;194:105-20. (Year: 2010).*
Albaran et al. Biochi Biophys Acta 2013;1833:3025-34. (Year: 2013).*
Andrade et al. Am J Physiol Renal Physiol 2011;300:F1223-34. (Year: 2011).*
Nassini et al. PLoS ONE 2012;7:e42454, pp. 1-12. (Year: 2012).*
Brini et al. Physiol Review 2009;89:1341-78. (Year: 2009).*
Toral-Ojeda et al. (Expert Rev Mole Med 2016;18-e7:1-14.*
Giacomello et al. (Am J Physiol Cell Physiol 308: C123-C138, 2015. First published Oct. 29, 2014) (Year: 2015).*
Jeffrey S. Chamberlain (Human Molecular Genetics, 2002, vol. 11, No. 20 2355-2362). (Year: 2002).*
Ackermann et al, "Integrity of the network sarcoplasmic reticulum in skeletal muscle requires small ankyrin 1", Journal of Cell Science, 2011, pp. 1-12.
Desmond et al, "Identification of Small Ankyrin 1 as a Novel Sarco(endo)plasmic Reticulum $Ca^{2+}$-ATPase 1 (SERCA 1) Regulatory Protein in Skeletal Muscle", The Journal of Biological Chemistry, vol. 290, No. 46, 2015, pp. 27854-27867.
Giacomello et al, "Deletion of small ankyrin 1 (sAnk1) isoforms results in structural and functional alterations in again skeletal muscle fibers", Am. J. Physiol. No. 308, 2015, pp. C123-C138.
Zhou et al, "Small, Membrane-bound, Alternatively Spliced Forms of Ankyrin 1 Associated with the Sarcoplasmic Reticulum of Mammalian Skeletal Muscle", The Journal of Cell Biology, vol. 156, No. 3, 1997, pp. 621-631.
Adams KF, Jr. "New epidemiologic perspectives concerning mild-to-moderate heart failure." *Am J Med* 110: 6S-13S, (2001).
Bhupathy et al., "Threonine-5 at the N-terminus can modulate sarcolipin function in cardiac myocytes," *J Mol Cell Cardiol*, 47:723-729, (2009).
Bhupathy et al., "Sarcolipin and phospholamban as regulators of cardiac sarcoplasmic reticulum Ca2+ ATPase," *J Mol Cell Cardiol*, 42:903-911, (2007).
Birkenmeier et al., "An alternative first exon in the distal end of the erythroid ankyrin gene leads to production of a small isoform containing an NH2-terminal membrane anchor," *Genomics*, 50:79-88, (1998).
Burr et al., "Genetic evidence in the mouse solidifies the calcium hypothesis of myofiber death in muscular dystrophy," *Cell Death Differ.* 22:1402-1412, (2015).
Cao et al., "Transmembrane dynamics of the Thr-5 phosphorylated sarcolipin pentameric channel." *Arch Biochem Biophys*, 604:142-151, 2016.
Coelho et al., "Heart failure and health related quality of life," *Clin Pract Epidemiol Ment Health*, 1:19, (2005).
Desmond et al., "Interactions between small ankyrin 1 and sarcolipin coordinately regulate activity of the sarco(endo)plasmic reticulum Ca2+-ATPase (SERCA1)," *J Biol Chem*, 292:10961-10972, (2017).
Goonasekera et al., "Mitigation of muscular dystrophy in mice by SERCA overexpression in skeletal muscle," *J Clin Invest*, 121:1044-1052, (2011).
Hovnanian, "SERCA pumps and human diseases," *Subcell Biochem*, 45:337-363, (2018).
Kimura et al., "Phospholamban inhibitory function is activated by depolymerization," *J Biol Chem*, 272:15061-15064, (1997).
Lipskaia et al., "Sarcoplasmic reticulum Ca(2+) ATPase as a therapeutic target for heart failure," *Expert Opin Biol Ther*, 10:29-41, (2010).
MacLennan et al., "The regulation of SERCA-type pumps by phospholamban and sarcolipin," *Ann N Y Acad Scie*, 986:472-480, (2003).

(Continued)

*Primary Examiner* — Scott Long
(74) *Attorney, Agent, or Firm* — Norton Rose Fulbright US LLP

(57) ABSTRACT

Embodiments of the disclosure concern methods and compositions related to the small Ankyrin 1 (sAnk1) protein and its role as a regulatory protein in at least muscle cells. In particular embodiments, its expression and/or activity are modulated with one or more compositions. In specific embodiments, compositions such as nucleic acids that inhibit expression of sAnk1 are utilized for a variety of methods, whereas in other embodiments compositions such as polypeptides, peptides, or sAnk1-encoding nucleic acids that enhance sAnk1 levels are utilized for certain methods.

11 Claims, 14 Drawing Sheets
Specification includes a Sequence Listing.

(56) References Cited

PUBLICATIONS

MacLennan et al., "Mechanistic models for muscle diseases and disorders originating in the sarcoplasmic reticulum," *Biochim Biophys Acta*, 1813:948-964, (2011).

Periasamy et al., "SERCA pump isoforms: their role in calcium transport and disease," *Muscle & Nerve*, 35:430-442, (2007).

Spinazzola et al., "Pharmacological therapeutics targeting the secondary defects and downstream pathology of Duchenne muscular dystrophy," *Expert Opin Orphan Drugs*, 4:1179-1194, (1974).

Tada et al., "The stimulation of calcium transport in cardiac sarcoplasmic reticulum by adenosine 3':5'-monophosphate-dependent protein kinase," *J Biol Chem* 249:6174-6180, (1974).

Tada et al., "Transient state kinetic studies of Ca2+-dependent ATPase and calcium transport by cardiac sarcoplasmic reticulum. Effect of cyclic AMP-dependent protein kinase-catalyzed phosphorylation of phospholamban," *J Biol Chem*, 255:1985-1992, (1980).

Wilson et al., "Epidemiology of cardiovascular disease in the United States," *Am J Kidney Dis*, 32:S56-S65, (1998).

\* cited by examiner

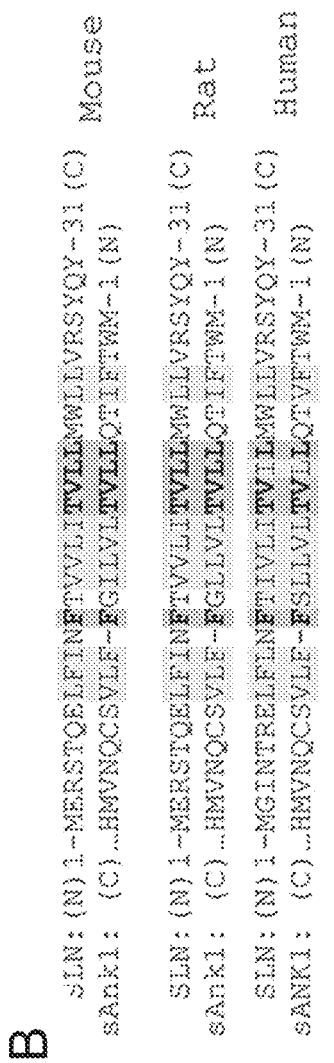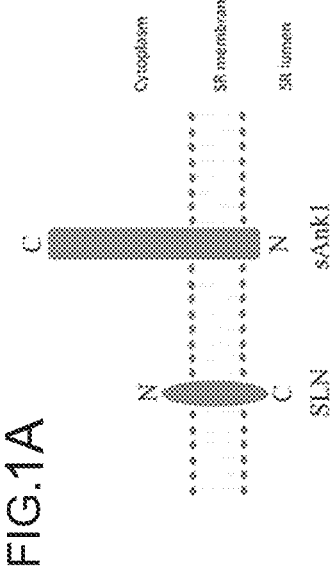

FIG. 3A
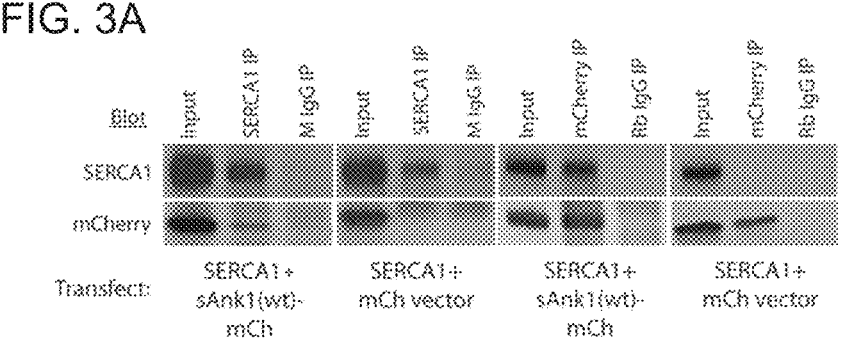
FIG. 3B
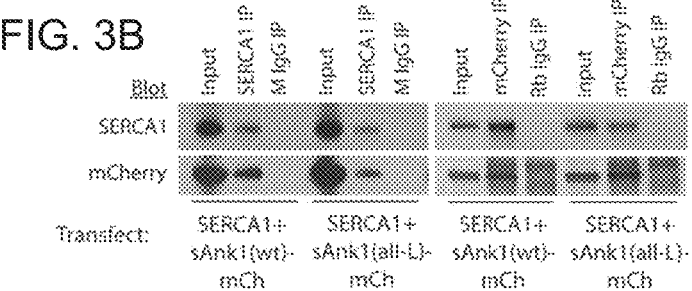
FIG. 3C sAnk Co-Immunoprecipitation
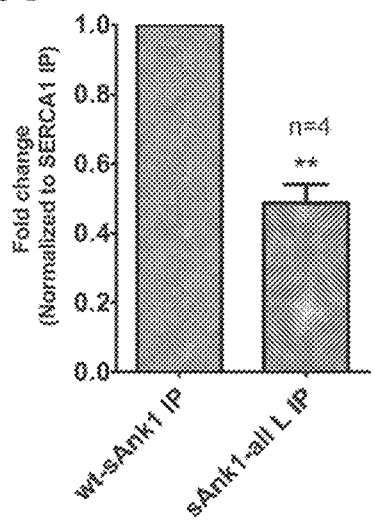
SERCA1 Co-Immunoprecipitation FIG. 3D
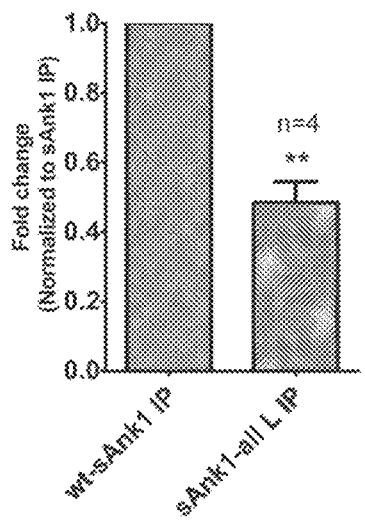

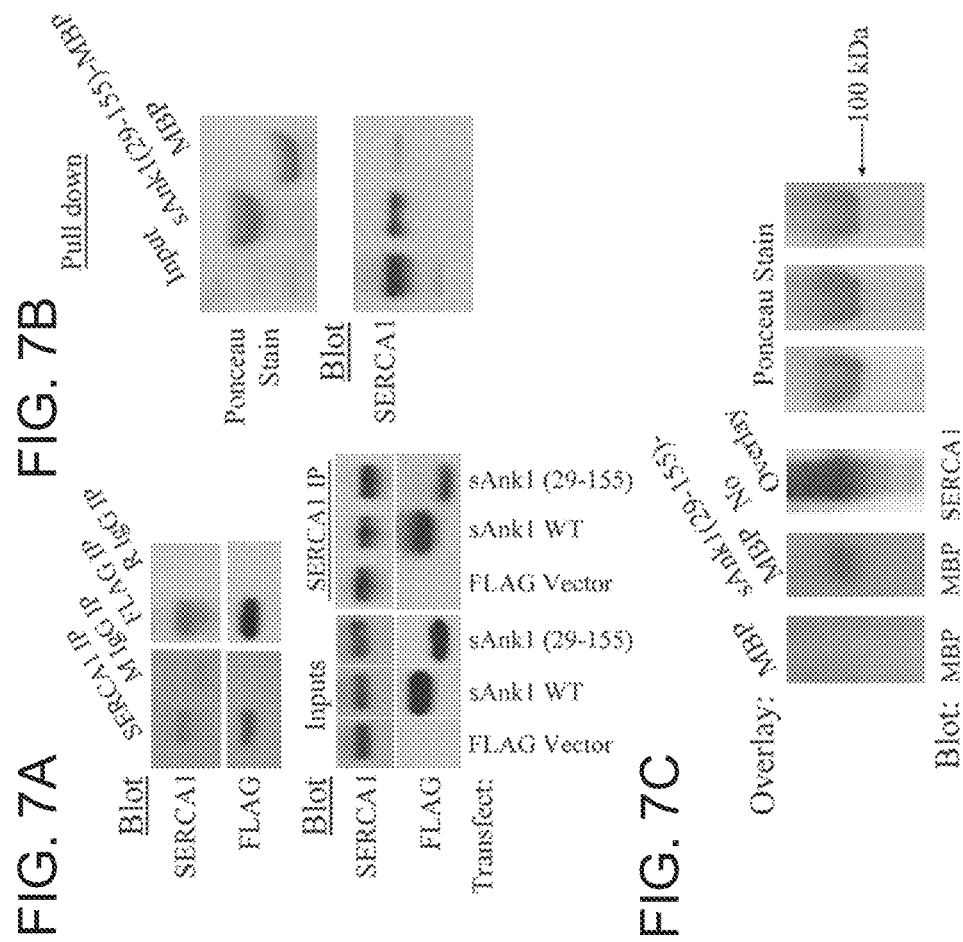

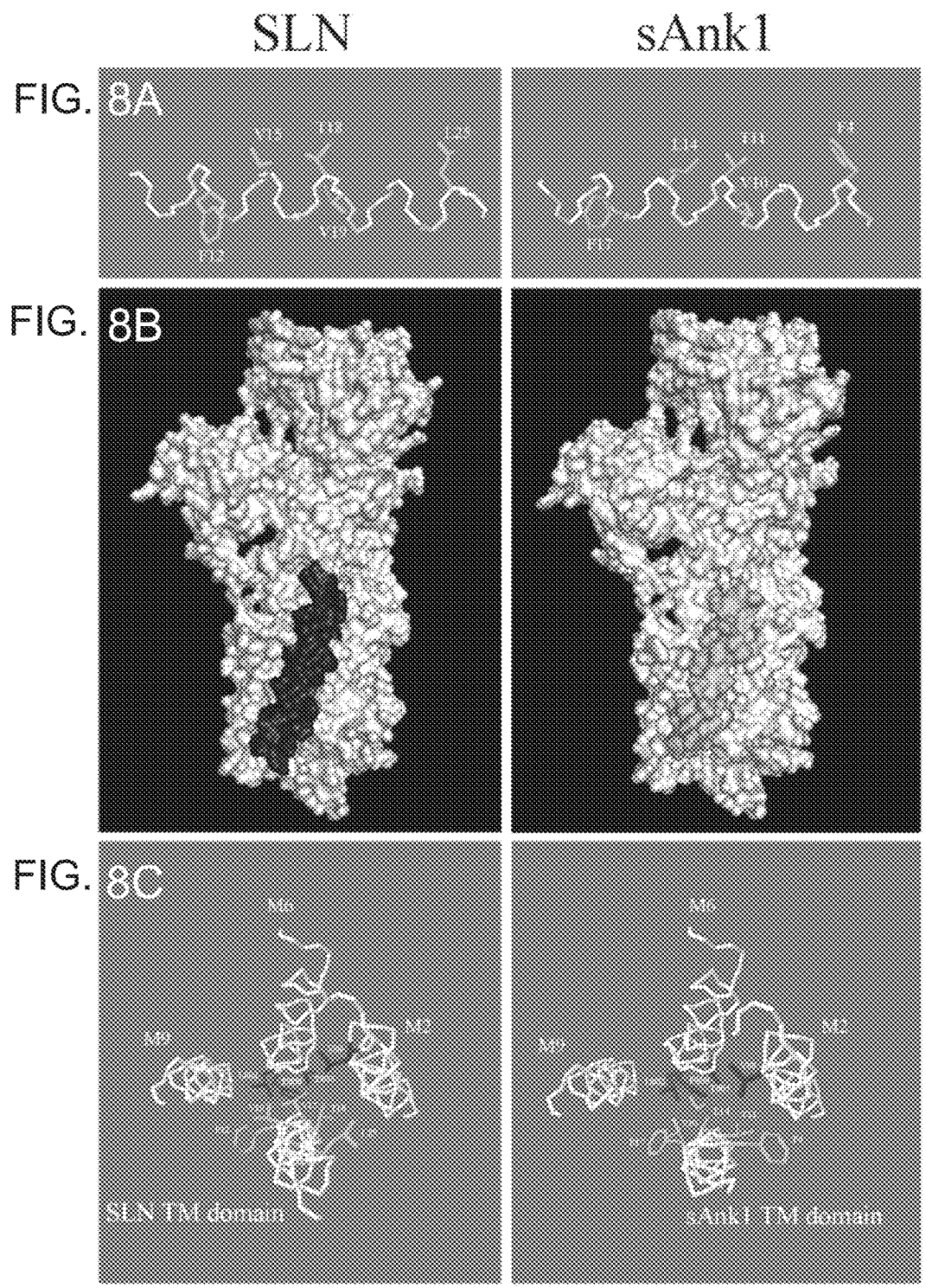

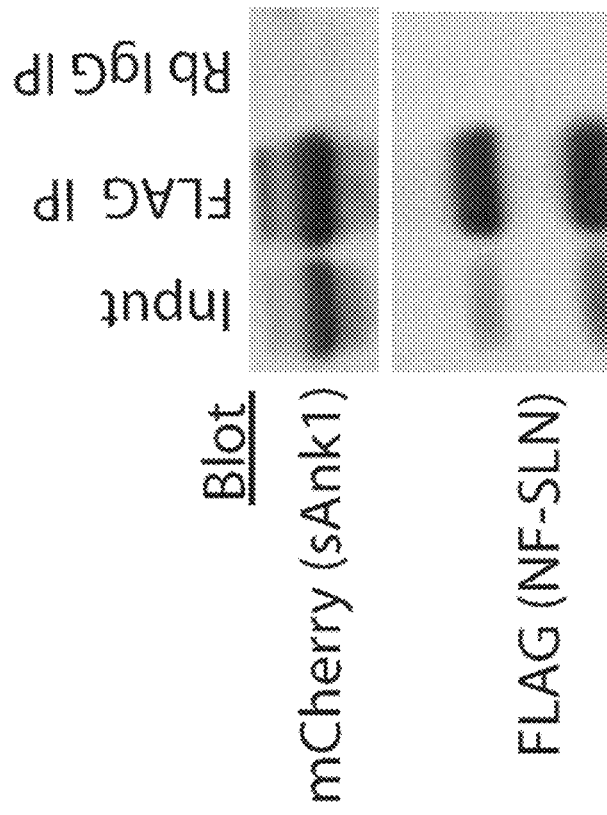
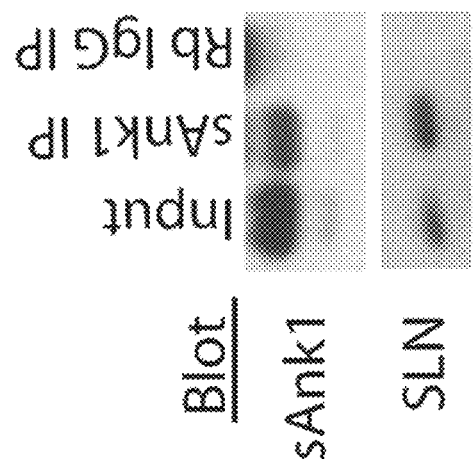

FIG. 12A
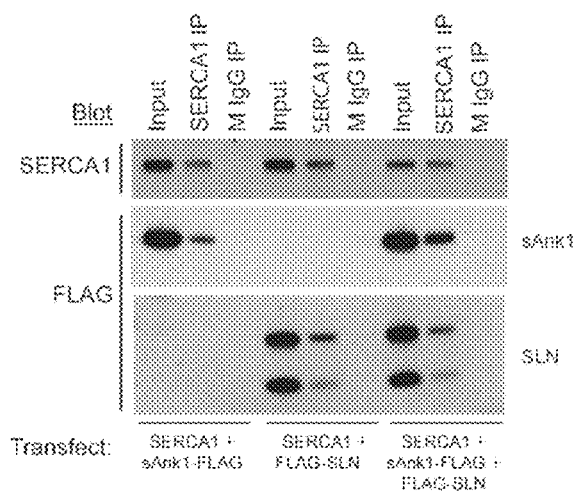
FIG. 12B
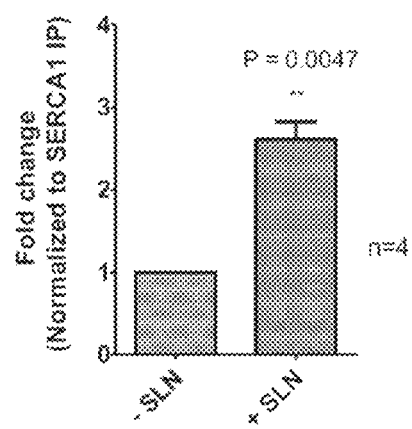
FIG. 12C
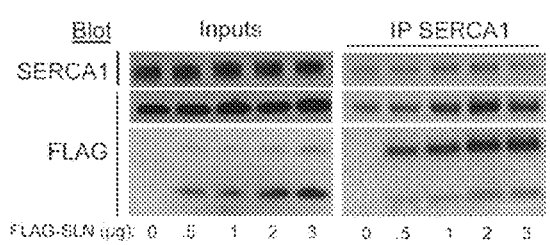
FIG. 12D
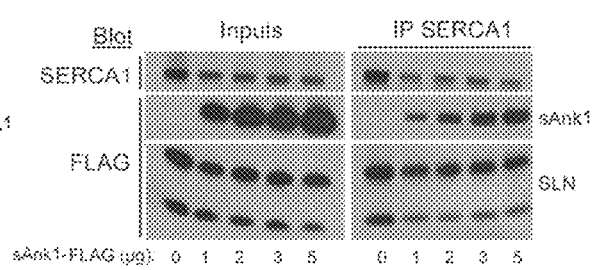
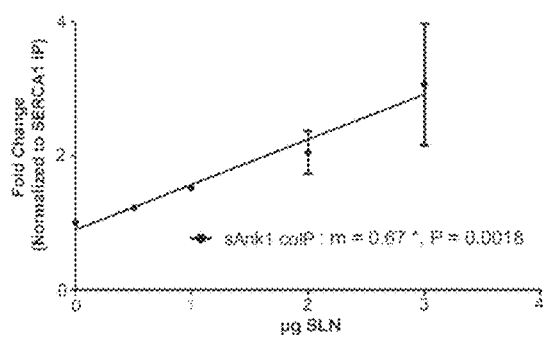
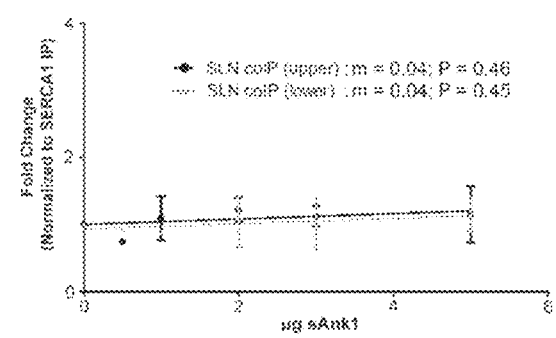
FIG. 12E
FIG. 12F FIG. 14A
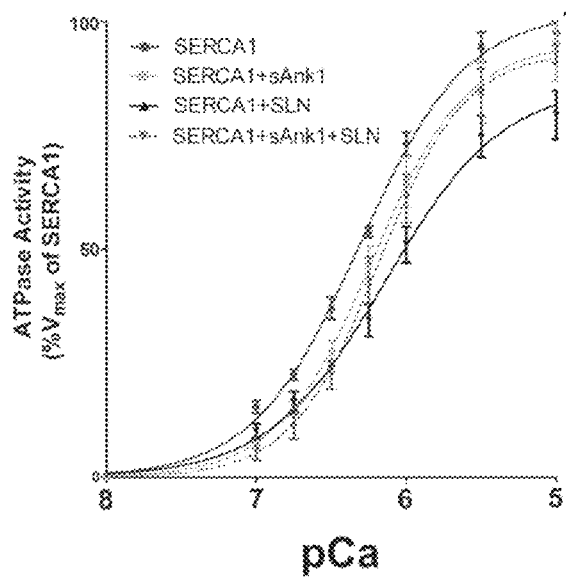
FIG. 14B
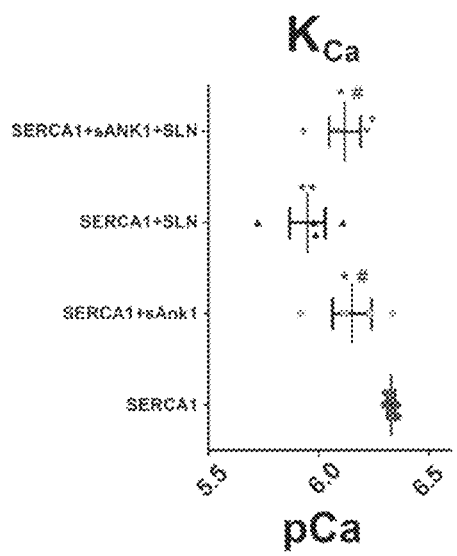
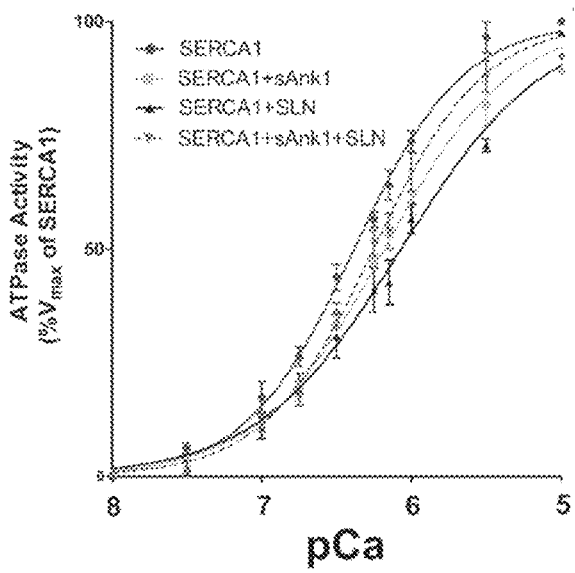
FIG. 14C
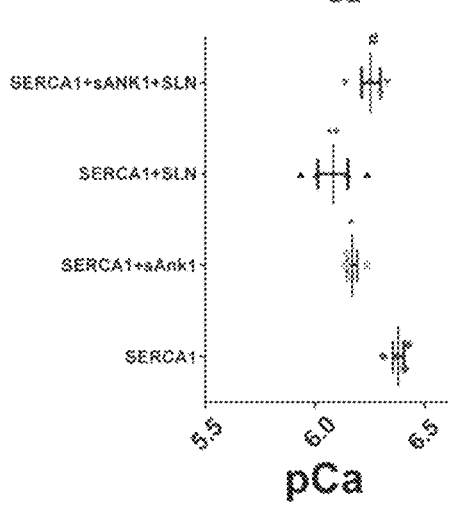
FIG. 14D

SEQUENCE LISTING

<160> NUMBER OF SEQ ID NOS: 16

<210> SEQ ID NO 1
<211> LENGTH: 468
<212> TYPE: DNA
<213> ORGANISM: Artificial Sequence
<220> FEATURE:
<223> OTHER INFORMATION: Synthetic Primer

<400> SEQUENCE: 1

```
atgtggactt tcgtcaccca gctgttggtc acgctggtgc tgctgagctt cttcctggtc      60
agctgtcaga acgtgatgca cattgtcagg gggtccctgt gctttgtgct aaagcacatc     120
caccaggagc tggacaagga gctgggggag agcgagggcc tcagtgacga cgaggagacc     180
atctccacca gggtggtccg gcggcgggtc ttcctgaagg ggaatgagtt tcagaatatt     240
ccaggggagc aggtgacaga ggagcaattc acggatgagc agggcaacat tgtcaccaag     300
aagatcattc gcaaggtggt tcgacagata gacttgtcca gcgccgatgc cgcccaggag     360
cacgaggagg tggagctgag agggagtggc ctacagccgg acctgataga gggcaggaag     420
ggggcgcaga tagtgaagcg ggccagcctg aaaaggggga acagtga                   468
```

<210> SEQ ID NO 2
<211> LENGTH: 155
<212> TYPE: PRT
<213> ORGANISM: Artificial Sequence
<220> FEATURE:
<223> OTHER INFORMATION: Synthetic Peptide

<400> SEQUENCE: 2

```
Met Trp Thr Phe Val Thr Gln Leu Leu Val Thr Leu Val Leu Leu Ser
1               5                  10                  15

Phe Phe Leu Val Ser Cys Gln Asn Val Met His Ile Val Arg Gly Ser
            20                  25                  30

Leu Cys Phe Val Leu Lys His Ile His Gln Glu Leu Asp Lys Glu Leu
        35                  40                  45

Gly Glu Ser Glu Gly Leu Ser Asp Asp Glu Glu Thr Ile Ser Thr Arg
    50                  55                  60

Val Val Arg Arg Arg Val Phe Leu Lys Gly Asn Glu Phe Gln Asn Ile
65                  70                  75                  80

Pro Gly Glu Gln Val Thr Glu Glu Gln Phe Thr Asp Glu Gln Gly Asn
                85                  90                  95

Ile Val Thr Lys Lys Ile Ile Arg Lys Val Val Arg Gln Ile Asp Leu
            100                 105                 110

Ser Ser Ala Asp Ala Ala Gln Glu His Glu Glu Val Glu Leu Arg Gly
        115                 120                 125

Ser Gly Leu Gln Pro Asp Leu Ile Glu Gly Arg Lys Gly Ala Gln Ile
    130                 135                 140

Val Lys Arg Ala Ser Leu Lys Arg Gly Lys Gln
145                 150                 155
```

<210> SEQ ID NO 3

<211> LENGTH: 3304
<212> TYPE: DNA
<213> ORGANISM: Artificial Sequence
<220> FEATURE:
<223> OTHER INFORMATION: Synthetic Primer

<400> SEQUENCE: 3

| | | | | | |
|---|---|---|---|---|---|
| gtcacccggg | ccactcaggg | cagagcctgg | ctgctgggca | gaagggcact | tgggccgggc | 60
| tgcttcagcc | gagagggcca | ttcggtgtcc | tgcccacaga | gagagaaaca | gtgagagacc | 120
| aagagagcaa | accagagaga | tagggagggg | gaatgcaagg | ggtccctggg | ggactcagga | 180
| gtcccagtgg | agaatgagag | gcaggccccc | cgtggtggcc | ggggcccctgg | ctgccagagg | 240
| accgggctgg | tgaggaggcg | aggatgtgga | ctttcgtcac | ccagctgttg | gtcacgctgg | 300
| tgctgctgag | cttcttcctg | gtcagctgtc | agaacgtgat | gcacattgtc | aggggggtccc | 360
| tgtgctttgt | gctaaagcac | atccaccagg | agctggacaa | ggagctgggg | gagagcgagg | 420
| gcctcagtga | cgacgaggag | accatctcca | ccagggtggt | ccggcggcgg | gtcttcctga | 480
| agggggaatga | gtttcagaat | attccagggg | agcaggtgac | agaggagcaa | ttcacgcatg | 540
| agcagggcaa | cattgtcacc | aagaagatca | ttcgcaaggt | ggttcgacag | atagacttgt | 600
| ccagcgccga | tgccgcccag | gagcacgagg | aggtggagct | gagagggagt | ggcctacagc | 660
| cggacctgat | agagggcagg | aaggggggcgc | agatagtgaa | gcgggccagc | ctgaaaaggg | 720
| ggaaacagtg | accccgagcc | gctctccttg | gagtagcctc | tcgggaggat | cacacctcga | 780
| caccccaaccc | ctgaacccca | cacactctgc | catgcacaca | ggaggagagc | tggacctgag | 840
| ggccaccgca | gcggtgcaca | cattcctctg | ggctgacggc | atgacctctg | taagggactc | 900
| ctgctagtcc | cctcttggca | tgaatgactg | actgtagacg | catgacctcc | aggcttcaat | 960
| cctgcctctt | gcaatgacag | ctgatctgtc | ggaaccagga | cacaaaagca | gcaagaagcg | 1020
| gggagagaga | gggatagaaa | acaagcgcag | gagagcctgc | gaacgcaaaa | gtgaatgagg | 1080
| gctttttgtg | gctggggatg | ggttttggtt | ttggggtttt | tttttaaat | tgttttgact | 1140
| tcgtacaggg | tactttttcc | caacctcatc | tgtcagaaat | ccatgtgggc | ttcctggaaa | 1200
| gaaaaaaaaa | aaaagaaaaa | ctaggcatga | aatcagttta | acaccttaat | cttaagccat | 1260
| gtcctcatct | gcccacccctc | cccaacccac | atacctccat | tccacttgtg | acacccctc | 1320
| gactccctgg | tgacgctcct | cccagatcgc | tctacatgac | attcaggaca | cacacacaca | 1380
| cacacacaca | ccactcgcct | ccactgaatc | tacacacaga | ttttactgtg | acttctgaag | 1440
| ctgtatagac | tctgctgtgg | ataaattgga | atttttttatg | ttgtctctct | ctctgccaat | 1500
| ttcaatacga | atcatcttcc | aatggaaaat | cattaccttg | aagagtgcat | tcggggttcc | 1560
| ttgtgttagg | gacttaagaa | tctgaggcga | ggacccccag | gcttacctgt | aggactcaaa | 1620
| gggagccagg | accccatctg | aaagggtctc | ctctctcagt | tgggggacag | gccggtggct | 1680
| gacccaggat | tgcaccagca | tgtccataga | aagaggtttt | tctatgtctt | caagcactat | 1740
| atcatagtcc | gtgttcaaag | tgtaaactgt | acagtaatca | gccttgtgta | tatgaaaaac | 1800
| aataaatact | atgcaaacca | atagaaacat | ttagcagtac | gtacagagcc | tgacagcgca | 1860
| gctcctgagg | acttctgcgg | ctgcaggaga | aggagctgtg | gcctgtcttt | cagtgaaaga | 1920
| ggaaggaaag | gagtagggct | agtgaatgta | tctgccaggt | cttagaagtc | aggaccaccc | 1980
| agggtctccc | agagtgaact | tggtgctcta | agtccaggca | gcctgcaggc | tggggaccct | 2040
| gggtgcaggt | gccaggctcg | aggctgttcc | ctgtcctgcc | tcagtgcctc | ccctctgccc | 2100
| agccccctgtg | gcctcttgga | gaggcgagcc | aggggggctcc | ccggaccgca | tggccggtga | 2160

-continued

```
gagtagagtc ggaggcggag agcctggacg cccagaggcc ggggccaggc tctgggtcaa    2220
ggcaggaagg agacagacag ctggcagttc ctcgcctcgg tgccatcagg gaggagcctt    2280
aagttccact agagcctccg gcccaggag gccagaatca gcacaatccc ggccccgccc     2340
tcgcggcggg cgccccagg gccaggagag agagacaggg ctggctcctc tcgcccctgg     2400
agccgcggtg tggacggccc ggccccgtcc gccccgccgc tctgcgggag tgtcctcggg    2460
acacacttaa accttccaag tagcacagaa gcccctcca cgtcagaggc ccctggccg      2520 cggggcctgt gagcggagag gggccctgct tcccacacaa atccgccccg gtgcacccc     2580 ggccaggcag gccccgggc ggcctaggcg ccttgtcggc cggggtggg gctgcttttg      2640 cttcctttag aggggcgggc agggagagga agctctagct ccgggcctga gtttccccga    2700
ggctgcgtcg gaggagctgc agggcgagcc cggacggctg ccgtctccgc cagaggccac    2760
cccggcccgg cctccagggc gcagaggcgc cccctccat cctcccccat cccggggcc      2820 acggcagggg ggccgcacag cgcggctggg accgattcgg tgacggccca aggaagctgg    2880
gctcagggct cgcctctccc gcctcgatcc tgcaccttcc tctcccaggt cgctgctgca    2940
gccaacccag tagcccccctt agcgccccg cggaccccgc agctccagac tccgctttgg    3000
cacctctgct ccggctggca tggctgcacg ctccggctgc tagtaggagc cgttagggga    3060
ggagtttggg gtctccacac gatgcctaga gaatgctgca gtctgcacat tagacgcttt    3120
ttagaagttt tgaaattacc ttgatttttt taattgttat gaaaatggat cttttcttga    3180
ctctcccaca tgctctgtta tgggagagaa tcccctaccc tactctgatg tatagaccat    3240
tctcccttca ccagccgaac caatgtcaaa attaataaag aaatggacta atggcaaaaa    3300
aaaa                                                                3304
```

```
<210> SEQ ID NO 4
<211> LENGTH: 103
<212> TYPE: DNA
<213> ORGANISM: Artificial Sequence
<220> FEATURE:
<223> OTHER INFORMATION: Synthetic Primer

<400> SEQUENCE: 4
ccgatcatgg agcgatccac ccgggagctg tgtctcaact tcactgttgt ccttattaca    60
gtgatcctta tttggctcct tgtgaggtcc taccagtact gag                     103

<210> SEQ ID NO 5
<211> LENGTH: 111
<212> TYPE: DNA
<213> ORGANISM: Artificial Sequence
<220> FEATURE:
<223> OTHER INFORMATION: Synthetic Primer

<400> SEQUENCE: 5
aattctcagt actggtagga cctcacaagg agccaaataa ggatcactgt aataaggaca    60
acagtgaagt tgagacacag ctcccgggtg gatcgctcca tgatcggagc t             111

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(6)
```

<223> OTHER INFORMATION: Xaa can be any naturally occurring amino acid

<400> SEQUENCE: 6

Phe Xaa Xaa Xaa Xaa Xaa Thr Val Leu Leu
1               5                   10

<210> SEQ ID NO 7
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 7

Met Glu Arg Ser Thr Gln Glu Leu Phe Ile Asn Phe Thr Val Val Leu
1               5                   10                  15

Ile Thr Val Leu Leu Met Trp Leu Leu Val Arg Ser Tyr Gln Tyr
            20                  25                  30

<210> SEQ ID NO 8
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 8

Met Trp Thr Phe Ile Thr Gln Leu Leu Val Thr Leu Val Leu Ile Gly
1               5                   10                  15

Phe Phe Leu Val Ser Cys Gln Asn Val Met His
            20                  25

<210> SEQ ID NO 9
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 9

Met Glu Arg Ser Thr Gln Glu Leu Phe Ile Asn Phe Thr Val Val Leu
1               5                   10                  15

Ile Thr Val Leu Leu Met Trp Leu Leu Val Arg Ser Tyr Gln Tyr
            20                  25                  30

<210> SEQ ID NO 10
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 10

Met Trp Thr Phe Ile Thr Gln Leu Leu Val Thr Leu Val Leu Leu Gly
1               5                   10                  15

Phe Phe Leu Val Ser Cys Gln Asn Val Met His
            20                  25

<210> SEQ ID NO 11
<211> LENGTH: 31
<212> TYPE: PRT
<213> ORGANISM: Artificial Sequence
<220> FEATURE:
<223> OTHER INFORMATION: Synthetic Peptide

```
<400> SEQUENCE: 11

Met Gly Ile Asn Thr Arg Glu Leu Phe Leu Asn Phe Thr Ile Val Leu
1               5                  10                 15

Ile Thr Val Ile Leu Met Trp Leu Leu Val Arg Ser Tyr Gln Tyr
                20                  25                 30

<210> SEQ ID NO 12
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 12

Met Trp Thr Phe Val Thr Gln Leu Leu Val Thr Leu Val Leu Leu Ser
1               5                  10                 15

Phe Phe Leu Val Ser Cys Gln Asn Val Met His
                20                  25

<210> SEQ ID NO 13
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 13

Met Trp Thr Phe Ile Thr Gln Leu Leu Val Thr Leu Val Leu Ile Gly
1               5                  10                 15

Phe Phe Leu Val Ser Cys Gln Asn Val Met His
                20                  25

<210> SEQ ID NO 14
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 14

Met Glu Arg Ser Thr Gln Glu Leu Phe Ile Asn Phe Thr Val Val Leu
1               5                  10                 15

Ile Thr Val Leu Leu Met Trp Leu Leu Val Arg Ser Tyr Gln Tyr
                20                  25                 30

<210> SEQ ID NO 15
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 15

Gly Ala Arg Gly Asn Leu Gly Asn Leu Phe Ile Asn Phe Cys Leu Ile
1               5                  10                 15

Leu Ile Leu Cys Leu Leu Leu Ile Cys Ile Ile Val Met Leu Leu
                20                  25                 30

<210> SEQ ID NO 16
<211> LENGTH: 26
<212> TYPE: PRT
<213> ORGANISM: Artificial Sequence
<220> FEATURE:
<223> OTHER INFORMATION: Synthetic Peptide
```

```
<400> SEQUENCE: 16

Ile Leu Gly Arg Leu Leu Lys Ile Leu Phe Val Leu Phe Val Asp Leu
1               5                   10                  15

Met Ser Ile Met Tyr Val Val Ile Thr Ser
            20                  25
```

REGULATING CALCIUM IN EXCITABLE CELLS WITH A NOVEL PROTEIN

This application claims priority to U.S. Provisional Patent Application Ser. No. 62/112,195, filed Feb. 5, 2015, which is incorporated by reference herein in its entirety.

This invention was made with government support under Grant Number AR056330 awarded by The National Institutes of Health. The government has certain rights in the invention.

TECHNICAL FIELD

The present invention generally relates at least to the fields of molecular biology, cell biology, muscle biology, calcium regulation, and medicine. In particular, the disclosure relates to small Ankyrin 1 (sAnk1), a regulator of SERCA activity, which may be utilized in the treatment of a variety of medical conditions, including heart failure and certain muscular dystrophies linked to calcium misregulation, for example.

BACKGROUND

The mechanisms that regulate calcium homeostasis are critical to the function and viability of eukaryotic cells. In muscle, maintaining low resting intracellular $Ca^{2+}$ ($[Ca^{2+}]_i$ <100 nM) compared to that found extracellularly (~2 mM) or within the lumen of the sarcoplasmic reticulum (SR; free, ~0.4 mM, total ~2 mM (1-4), is critical to excitation-contraction coupling (5). The sarco(endo)plasmic reticulum calcium ATPase (SERCA) is the enzyme that pumps $Ca^{2+}$ from the cytoplasm into the lumen of the SR, leading to muscle relaxation following contraction. In mammals, there are three ATP2A genes that encode more than 10 different SERCA isoforms (6). The ubiquitous expression of one or more SERCA isoforms highlights its importance in the $Ca^{2+}$ dynamics of muscle and non-muscle cells alike. Alterations in SERCA expression and activity are linked to several forms of muscular dystrophy and cardiomyopathies, including heart failure (5, 7-10). In addition, age-related alterations in SERCA levels have been observed in both animal models of aging and senescent human myocardium, suggesting changes in SERCA activity may also be relevant to the aging process (6).

The small transmembrane (TM) proteins, phospholamban (PLN) and sarcolipin (SLN), are the two most well-known regulators of SERCA activity. PLN is expressed at high levels in the ventricles of the heart and at lower levels in the atria and in slow-twitch skeletal muscle (11-13). SLN expression is more prominent in the atria and in fast-twitch skeletal muscle of larger mammals (10, 14-18). SLN and PLN share extensive homology in their TM sequences (14, 19, 20), which mediate their binding to several of the TM helices of SERCA (21-27). The TM sequences also mediate homo- and hetero-oligomerization of PLN and SLN (19, 28-35). SLN and PLN also interact with SERCA via their lumenal and cytoplasmic sequences, respectively (36-38).

The binding of PLN or SLN to SERCA is associated with a reduction in SERCA's apparent $Ca^{2+}$ affinity (39), and both proteins together have been reported to have a synergistic effect, leading to super-inhibition of SERCA, presumably through forming a ternary complex (24, 28). Recent studies demonstrate that PLN and SLN can be co-expressed in both human and rodent skeletal muscle tissue, suggesting that super-inhibition of SERCA activity may play a significant role in the regulation of intracellular $Ca^{2+}$ (37, 40).

Another small SR protein, myoregulin (MLN), which like SLN interacts with SERCA1 and inhibits its activity, has also been recently reported (41).

Small ankyrin 1 (sAnk1, also known as Ank1.5), an alternatively spliced product of the ANK1 gene, is a 155 amino acid TM protein (42-44). The 82 C-terminal cytoplasmic residues share homology with the larger members of the ankyrin superfamily, while the 73 N-terminal residues are unique to sAnk1 and include a TM domain in its most N-terminal sequence (44-46). sAnk1 localizes to the network compartment of the SR (nSR) (44, 45, 47-52) and colocalizes with SERCA1 in the nSR surrounding Z-disks (43, 49). The C-terminus of sAnk1 protrudes into the cytoplasm (45) where it can interact with the giant myofibrillar proteins, obscurin and titin (50, 51, 53). These interactions provide a potential connection between the nSR membrane and the underlying contractile apparatus, and are thought help to organize the SR membrane around each sarcomere (50, 54, 55).

In a 2011 study, Ackermann et al. examined the effects of reducing the expression of sAnk1 in mouse myofibers using siRNA targeted to the 5' UTR of its mRNA (49). Decreases in sAnk1 mRNA and protein levels were accompanied by a reduction in both SERCA and SLN protein (but not mRNA) levels. Consistent with these results, $Ca^{2+}$ uptake kinetics and lumenal SR $Ca^{2+}$ stores were reduced in myofibers depleted of sAnk1 (49). Reintroducing sAnk1 by transfection rescued SERCA localization. Remarkably, the loss of sAnk1 significantly disrupted SERCA and SLN localization within the nSR but had much smaller effects on proteins of the triad junction and sarcomere (49). More recently, Giacomello et al. showed that muscle cells lacking sAnk1 due to homologous recombination have a compartment that was both reduced in size and slower to take up $Ca^{2+}$ (56). These observations indicate that sAnk1 may play a broader role than initially believed in the organization and stabilization of the nSR.

In particular embodiments of the disclosure, sAnk1 can interact directly with SERCA and that interaction can be modulated to satisfy needs in the art of medicine in cases where calcium homeostasis is involved with a medical condition.

BRIEF SUMMARY

The present invention is directed to methods and compositions related to modulation of calcium in muscle cells and/or brain cells. In particular embodiments, need for the modulation is associated with defective calcium homeostasis in muscle cells and/or brain cells, although in some cases the modulation is produced to enhance normal, existing calcium homeostasis in cells for a therapeutic or otherwise beneficial effect.

Embodiments of the disclosure relate to identification of small ankyrin 1 (sAnk1) as a novel sarco(endo)plasmic reticulum $Ca^{2+}$-ATPase 1 (SERCA1) regulatory protein in skeletal muscle, although other embodiments concern regulation of SERCA1 by sAnk1 in brain cells. Specific embodiments provide compositions and methods for regulating calcium in excitable cells utilizing sAnk1 compositions. In certain embodiments, modulation of sAnk1 levels and/or its ability to bind other proteins leads to restoration of normal levels of calcium in cells having aberrant calcium levels. In some embodiments, sAnk1 interacts with SLN either directly or indirectly (such as in a complex with SERCA1), and that interaction results in a reduction in SLN's inhibitory effect on SERCA1 activity; therefore, in specific embodiments overexpression of sAnk1 would diminish the inhibition of SERCA by SLN, leading to a decrease in cytosolic calcium levels to normal levels in muscle and/or brain cells. In other embodiments, inhibition of sAnk1 levels and/or its ability to interact with SERCA leads to reduction in excess calcium levels in muscle and/or brain cells.

Increasing expression of sAnk1 in cells in need of a decrease in cytosolic calcium levels may occur by any means, but in specific embodiments the level is achieved using overexpression of a sAnk1-encoding nucleic acid in the cells and/or delivery of at least part of the sAnk1 protein in the cells. In either event, the sAnk1 protein level is increased in the cells, leading at least to a reduction in SLN's ability to inhibit SERCA. The sAnk1 protein may be modified compared to wildtype and/or the sAnk1 protein may be expressed as an alternatively spliced form, and/or the sAnk1 protein may be labeled, in at least specific cases. The sAnk1-encoding nucleic acid for overexpression of sAnk1 and/or the sAnk1 polypeptide or peptide may be dispersed in a pharmaceutical formulation for delivery to an individual in need thereof, such as an individual with muscle disease or brain disease.

The disclosure also provides recombinant plasmids and viral vectors that express the sAnk1 protein or a functional fragment thereof, as well as pharmaceutical compositions comprising the sAnk1 protein or a functional fragment thereof (that may or may not be on a vector) and a pharmaceutically acceptable carrier.

Inhibition of sAnk1 may be achieved in a variety of ways, but in specific embodiments the level of sAnk1 in muscle and/or brain cells is achieved through RNA interference. Specific aspects provided herein include use of sAnk1 siRNA to reduce cellular levels of sAnk1 in muscle and/or brain cells, thereby providing a therapeutic benefit to an individual with a medical condition in which calcium homeostasis is defective.

In specific embodiments, the sAnk1 siRNA comprises a sense RNA strand and an antisense RNA strand that form an RNA duplex. The sense RNA strand comprises a nucleotide sequence identical to a target sequence of about 19 to about 25 contiguous nucleotides in the sAnk1 mRNA, in at least some cases.

The disclosure also provides recombinant plasmids and viral vectors that express the sAnk1 siRNA of the disclosure, as well as pharmaceutical compositions comprising the sAnk1 siRNA of the disclosure (that may or may not be on a vector) and a pharmaceutically acceptable carrier.

The invention further provides a method of inhibiting expression of human sAnk1, or an alternative splice form, mutant or cognate thereof, comprising administering to a subject an effective amount of the sAnk1 siRNA of the disclosure such that the target sAnk1 mRNA is degraded.

The disclosure further provides a method of treating a muscle-related disease or brain-related disease, either or which relate to defective calcium homeostasis, comprising administering to a subject in need of such treatment an effective amount of an sAnk1 siRNA targeted to human sAnk1 mRNA, or an sAnk1 siRNA targeted to an alternative splice form, mutant or cognate thereof, such that the disease is treated (for example, at least one symptom is ameliorated). The treatment may encompass complete amelioration of the disease, or the treatment may encompass a reduction in progression of the disease.

Embodiments of the disclosure include methods of treating a medical condition in an individual, comprising the step of providing to the individual a therapeutically effective amount of a composition that modulates the level and/or activity of small Ankyrin 1 (sAnk1) in muscle cells and/or brain cells of the individual, wherein the medical condition comprises aberrant calcium homeostasis in muscle cells and/or brain cells, respectively. In specific embodiments, the composition increases the level and/or activity of sAnk1 in muscle cells and/or brain cells of the individual. The composition may comprise nucleic acid, and the composition may comprise an expression vector. In specific embodiments, the nucleic acid encodes part or all of the sAnk1 coding sequence, which may or may not be modified compared to wildtype sAnk1 sequence. In specific embodiments, the nucleic acid encodes a fusion protein that comprises part or all of the sAnk1 coding sequence with a fusion entity, which may be a label. In cases wherein one or more expression vectors are employed, an expression vector may be a viral vector (such as an adenoviral vector, an adeno-associated viral vector, a lentiviral vector, or a retroviral vector) or a non-viral vector.

Some embodiments of the methods utilize compositions that comprise a polypeptide or peptide. The polypeptide may comprise part or all of the sAnk1 protein, and the sAnk1 protein may or may not be modified compared to wildtype sAnk1 protein sequence. In specific embodiments, the sAnk1 protein is part of a fusion protein that comprises part or all of the sAnk1 protein with a fusion entity, and the fusion entity may be a label.

In particular embodiments, a composition reduces the level and/or activity of sAnk1 in muscle cells and/or brain cells of the individual. Such a composition may comprise a nucleic acid molecule that comprises a nucleotide sequence that binds to at least a portion of SEQ ID NO:1 or SEQ ID NO:3. In specific cases, a region of the nucleic acid molecule is at least 70%, 75%, 80%, 85%, 90%, 95%, 97%, or 99% complementary to at least a portion of SEQ ID NO:1 or SEQ ID NO:3. The composition may be an RNA molecule, such as a siRNA molecule, which may or may not be comprised on a vector, including a viral vector (such as an adeno-associated viral vector, an adenoviral vector, a retroviral vector, or a lentiviral vector) or a non-viral vector. In some cases, expression of the siRNA molecule is regulated by a muscle-specific regulatory region, such as a muscle-specific regulatory region is from muscle creatine kinase (MCK); the Duchenne muscular dystrophy gene; Pitx3; troponin I; skeletal alpha-actin; desmin; or a combination thereof, for example.

In particular embodiments of the methods, the muscle cells are heart muscle cells or skeletal muscle cells. In certain aspects, the medical condition is cardiomyopathy, muscular dystrophy, or skeletal myopathy. In specific cases, the composition reduces the level and/or activity of sAnk1 in brain cells of the individual, and the medical condition comprises symptoms related to memory, learning, or a combination thereof.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 1A, 1B, 1C, and 1D. Sequence comparison in transmembrane regions of sAnk1 and SLN. 1A. Relative orientation of sAnk1 and SLN within the SR membrane. 1B. Residues that are identical or conserved in sAnk1 and SLN are highlighted in dark and light gray, respectively (SEQ ID NOS. 7-12). 1C. Percent similarity between sAnk1 and SLN. 1D. Mouse amino acid sequence comparison of the transmembrane region of sAnk1, SLN, PLN and MLN. Similar residues are highlighted in gray. (SEQ ID NOS. 13-16)

FIGS. 3A, 3B, 3C, and 3D. CoIP of SERCA and sAnk1 from COS7 cells. 3A. Extracts of COS7 cells transfected as indicated below were subjected to IP with antibodies to SERCA1, sAnk1, or mCherry. Non-immune rabbit or mouse IgG was used as controls. The results show that SERCA1 and WT sAnk1 coIP specifically in COS7 cells, consistent with the results from muscle tissue. 3B. Compared to sAnk1 (WT), expression of a form of sAnk1 in which all of its transmembrane amino acids were converted to leucines [sAnk1 (all-L)] with SERCA1 led to a significant reduction in coIP between the two proteins. This is consistent with the involvement of the transmembrane sequence of sAnk1 in its interaction with SERCA. 3C & 3D. Quantitative comparison showed that coIP was reduced by ~50% for the mutant sAnk1 when normalized to coIP of SERCA1 and sAnk1 (WT). Reduction in coIP between SERCA1 and sAnk1 (all-L) ranged between 34 and 61%. This result was statistically significant by t-test (3C, p=0.0024 and 3D, p=0.0033). Note: bands observed in IP lanes above mCherry protein (3A) and above and below sAnk1 (WT)-mCh are non-specific bands due to the presence of the subunits of the antibodies used for IP.

FIGS. 7A, 7B, and 7C. The cytoplasmic domain of sAnk1 directly interacts with SERCA1 in vitro. 7A. top: Extracts of COS7 cells transfected to express SERCA1 and WT sAnk1 carrying a FLAG epitope tag (sAnk1-FLAG) were subjected to IP with antibodies to SERCA1 or FLAG. Non-immune mouse or rabbit IgG were used as controls. The results show that SERCA1 and sAnk1-FLAG specifically interact in COS7 cells, and that the epitope tag on sAnk1 does not alter this interaction. bottom: COS7 extracts were co-transfected to express SERCA1 and FLAG-tagged versions of full length sAnk1 or the cytoplasmic domain, $sAnk1_{29-155}$. A FLAG empty vector was used as controls. The results indicate that, like FLAG-tagged full length sAnk1 (sAnk1 WT), a FLAG-tagged form of the cytoplasmic domain of sAnk1 ($sAnk1_{29-155}$) also coIPs with SERCA1. 7B. Amylose resin bound to bacterially expressed $sAnk1_{29-155}$-MBP fusion protein was incubated with COS7 extracts transfected to express SERCA1. MBP protein alone was used as a control. Densitometric analysis of the eluates after SDS-PAGE and blotting with antibodies to SERCA1 revealed a 9-fold increase in the amount of SERCA1 pulled down by $sAnk1_{29-155}$ relative to the MBP control (bottom panel). Ponceau staining was used as a loading control (top panel). 7C. SR vesicle preparations were used for blot overlay assays. Blots were first overlaid with $sAnk1_{29-155}$-MBP or MBP protein alone, followed by incubation with antibodies to MBP. The labeled band at ~110 kDa (left panel) indicates that $sAnk1_{(29-155)}$-MBP, but not MBP protein alone, can bind to SERCA1 directly. Ponceau staining was used as a loading control (right panel).

FIGS. 8A, 8B, and 8C. Modeling the sAnk1 transmembrane (TM) domain. 8A. The TM domains of SLN (top) and sAnk1 (bottom) were modeled with I-TASSER webware. The results show that 5 side chains in the TM α-helix of sAnk1 occupy very similar positions along the helix as their counterparts in the TM domain of SLN (highlighted in green). 8B. ClusPro 2.0 webware was used to determine the predicted docking site of sAnk1 to SERCA1. Comparison of this model to the published crystal structure of rabbit SERCA1a docked to SLN was performed with PyMOL 1.3. The results show that sAnk1 is predicted to dock to SERCA1 in a similar, but not identical, position to SLN. 8C. Backbone helices of SERCA and sAnk1 are shown in white. SERCA residues highlighted in magenta and red are reported to be important for SLN-mediated SERCA inhibition. Similar residues shared between sAnk1 and SLN are highlighted in green. The docking model shows that the sAnk1 residues which extend into the TM binding pocket of SERCA1 are positioned similarly to those of SLN. Orientation is from inside the SR lumen, looking down into the cytoplasm.

FIGS. 9A and 9B show coIP of sAnk1 and SLN from rabbit skeletal muscle and COS7 cells. 9A. SR vesicles were solubilized and subjected to IP with antibodies to sAnk1. 9B. Extracts of COS7 cells transfected with sAnk1-mCherry and FLAG-SLN (NF-SLN) were subjected to IP with antibodies against mCherry. Non-immune rabbit IgG was used as a control. The results show that sAnk1 and SLN coIP in skeletal muscle extracts and COS7 cell lysates.

FIGS. 12A, 12B, 12C, 12D, 12E, and 12F demonstrate SLN promotes interaction between SERCA1 and sAnk1. 12A. COS7 cell extracts transfected as indicated below each panel were subjected to IP with antibodies specific to SERCA1. 12B. Quantitative densitometry analysis was performed to assess coIP between SERCA1 and sAnk1 in the presence or absence of FLAG-SLN. There was a 2.6-fold increase in coIP of sAnk1 when coexpressed with FLAG-SLN. 12C. Titration of FLAG-SLN as indicated below each panel reveals increased interaction between SERCA1 and sAnk1 with increasing expression of FLAG-SLN. 12D. Titration of sAnk1-FLAG has no effect on coIP between SERCA1 and FLAG-SLN. 12E and 12F. Graphical representation of densitometric analysis of experiments shown in 12C and 12D, respectively. Linear regression shows a significant increase in coIP of sAnk1 with SERCA1 with increasing SLN expression (panel E: m=0.0672±0.15; P=0.0018; n=2), while increasing sAnk1 expression had no significant effect on coIP of SLN with SERCA1 (panel F: m=0.0404±0.53; P=0.5921 (upper band) and m=0.3992±0.05080; P=0.6421 (lower band); n=2). Data represent slope±S.E.M.

FIGS. 14A, 14B, 14C, and 14D demonstrate $Ca^{2+}$-ATPase assays. COS7 (14A) and HEK293 (14C) cells were transfected with the indicated cDNA construct(s). ATPase activity was determined at each $[Ca^{2+}]_{free}$ compared to the $V_{max}$ measured for SERCA1 alone, following normalization of the levels of SERCA1 expression as determined by immunoblotting (see Experimental Procedures). Data were fitted to the equation for a general cooperative model for substrate binding. Results from both cell lines show that co-expression of sAnk1 with SERCA leads to a reduction of SERCA's apparent affinity for $Ca^{2+}$, but that the effect of sAnk1 is less than that of SLN. 14B and 14D. The $K_{ca}$ ($[Ca^{2+}]_{free}$ required for half-maximal activation) values were determined from each curve. COS7 mean $K_{ca}$: SERCA1 pCa=6.33 (468 nM), SERCA1+sAnk1 pCa=6.15 (708 nM), SERCA1+SLN pCa=5.95 (1122 nM), and SERCA1+sAnk1+SLN pCa=6.12 (759 nM). HEK 293 mean $K_{ca}$: SERCA1 pCa=6.38 (415 nM), SERCA1+sAnk1 pCa=6.17 (680 nM), SERCA1+SLN pCa=6.08 (830 nM), and SERCA1+sAnk1+SLN pCa=6.26 (560 nM). Statistics used 1 way ANOVA: *, p<0.05 vs SERCA1, **, p<0.01 vs SERCA1 and #, p<0.05 vs SERCA1+SLN.

DETAILED DESCRIPTION

Figure 2B:
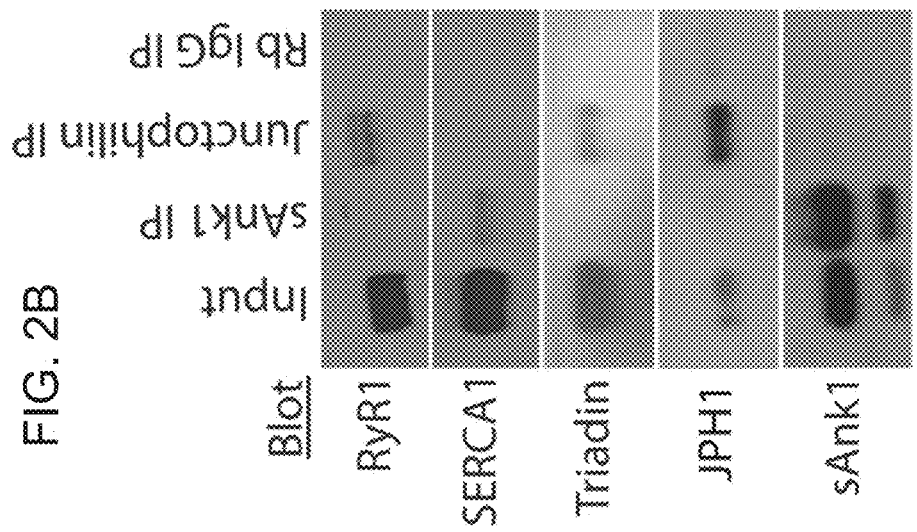
FIGS. 2A and 2B. Co-immunoprecipitation (co-IP) of SERCA and sAnk1 from rabbit skeletal muscle. 2A. SR vesicles were solubilized and subjected to IP with antibodies to SERCA1 or sAnk1. 2B. Specificity was demonstrated with an antibody to junctophilin-1 (JPH1), which co-immunoprecipitated RyR1 and TRDN but not SERCA1 or sAnk1. Non-immune rabbit or mouse IgG were used as controls and did not immunoprecipitate either SERCA1 or sAnk1. The results show that SERCA1 and sAnk1 coIP specifically from solubilized SR vesicles.

As used herein, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

I. General Embodiments

The disclosure herein concerns regulation of calcium levels in cells by targeting directly or indirectly the role that small ankyrin 1 (sAnk1) (which may also be referred to as SPH1 or SPH2) plays in cytoplasmic calcium homeostasis. sAnk1 is required for stability of the network sarcoplasmic reticulum and shares transmembrane similarity with sarcolipin. sAnk1-SERCA interactions and their effects on SERCA are demonstrated herein by co-immunoprecipitation, FRET, blot overlay and $Ca^{2+}$-ATPase assays. sAnk1 binds SERCA and reduces SERCA's affinity for $Ca^{2+}$, and sAnk1 also inhibits SLN's ability to regulate SERCA activity. Thus, in certain embodiments an increase in cellular sAnk1 is desired to enhance its inhibition of SLN, whereas in other embodiments a reduction in cellular sAnk1 is desired to reduce inhibition of SERCA by sAnk1. The increased level of sAnk1 available in cells to bind to SLN and/or the interference of SLN's ability to bind SERCA are encompassed in compositions and methods of the disclosure. The reduced level of sAnk1 available in cells to bind to SERCA and/or the interference in sAnk1's ability to bind SERCA are encompassed in compositions and methods of the disclosure.

II. Compositions

In some embodiments, an increase in sAnk1 in muscle and/or brain cells is desired to achieve a therapeutic effect in an individual, whereas in other embodiments a decrease in sAnk1 in muscle and/or brain cells is desired to achieve a therapeutic effect in an individual. To implement such outcomes, one can utilize certain sAnk1-encoding nucleic acids, siRNAs, and/or peptides and/or polypeptides.

In specific embodiments, nucleic acids will either provide increased levels of sAnk1, leading to an increase in sAnk1 protein level, or other nucleic acids will target sAnk1 mRNA, leading to reduction in sAnk1 protein level. An exemplary human sAnk1 protein is located at the NCBI GenBank database under Accession number NP_065211.2. The protein of NP_065211.2 is as follows:

A. Increasing sAnk1 Levels

In some embodiments, it is desirable to increase cellular levels of sAnk1 so that it can decrease the ability of SLN to inhibit SERCA. The increase in sAnk1 levels in cells may be achieved in a variety of ways, including by increasing nucleic acids that encode part or all of sAnk1 and/or by increasing sAnk1 polypeptides. In specific embodiments, sAnk1-encoding nucleic acids and/or sAnk1 polypeptides or peptides are utilized to increase sAnk1 levels in muscle and/or brain cells.

In specific embodiments, one can increase the levels of sAnk1 by overexpressing nucleic acids that encode part or all of the sAnk1 protein. The overexpression can be achieved by increasing numbers of sAnk1-encoding nucleic acids, such as by regulating their expression with a robust regulatory sequence (which may be referred to as a promoter). The nucleic acids that are provided to cells in need thereof may encode part or all of the sAnk1 protein. In cases wherein only part of the sAnk1 protein is encoded, the region may include the transmembrane domain (amino acids 1-29); the SERCA binding domain (amino acids 29-155); a dimerization domain; an oligomerization domain; part or all of the N-terminal 29 amino acid hydrophobic sequence that targets proteins to and anchors them in the sarcoplasmic reticulum (SR), the domain that binds SLN, and so forth.

```
                                                                    (SEQ ID NO: 2)
  1    MWTFVTQLLV TLVLLSFFLV SCQNVMHIVR GSLCFVLKHI HQELDKELGE SEGLSDDEET

61    ISTRVVRRRV FLKGNEFQNI PGEQVTEEQF TDEQGNIVTK KIIRKVVRQI DLSSADAAQE

121    HEEVELRGSG LQPDLIEGRK GAQIVKRASL KRGKQ
```

The sAnk1 protein may be encoded by the following sequence:

```
                                                  (SEQ ID NO: 1)
ATGTGGACTTTCGTCACCCAGCTGTTGGTCACGCTGGTGCTGCTGAGCTT

CTTCCTGGTCAGCTGTCAGAACGTGATGCACATTGTCAGGGGGTCCCTGT

GCTTTGTGCTAAAGCACATCCACCAGGAGCTGGACAAGGAGCTGGGGGAG

AGCGAGGGCCTCAGTGACGACGAGGAGACCATCTCCACCAGGGTGGTCCG

GCGGCGGGTCTTCCTGAAGGGGAATGAGTTTCAGAATATTCCAGGGGAGC

AGGTGACAGAGGAGCAATTCACGGATGAGCAGGGCAACATTGTCACCAAG

AAGATCATTCGCAAGGTGGTTCGACAGATAGACTTGTCCAGCGCCGATGC

CGCCCAGGAGCACGAGGAGGTGGAGCTGAGAGGGAGTGGCCTACAGCCGG

ACCTGATAGAGGGCAGGAAGGGGGCGCAGATAGTGAAGCGGGCCAGCCTG

AAAAGGGGGAAACAGTGA
```

Also encompassed herein is a sAnk1 mRNA transcript, provided as SEQ ID NO:3 (GenBank Accession Number NM_020478).

In particular embodiments of the disclosure, provided herein is inhibition of sAnk1 to bind SERCA and/or the reduction in sAnk1 cellular levels leading to a reduced pool of sAnk1 with which to bind to SERCA. Although such inhibition may occur by any suitable means in the art, in specific embodiments the reduction of sAnk1 protein levels occurs by reducing the level of sAnk1 nucleic acid, including sAnk1 mRNA levels. Such inhibition may occur using nucleic acid compositions to target sAnk1 mRNA, such as through RNA interference, for example.

In certain embodiments, the sAnk1 polypeptide, or the encoded sAnk1 polypeptide from the sAnk1 nucleic acid, may be fused to another entity. In specific embodiments, the entity enhances the ability of sAnk1 to perform its intended use, such as the enhancing the ability of sAnk1 to bind to SLN. The fusion entity may be a label or it may be an entity that enhances sAnk1 activities other than the binding to SLN. In specific embodiments, the fusions are to the C-terminal end that faces the cytoplasm.

In some embodiments, one could fuse sAnk1 to "Killer Red", a fluorescent protein that when activated by light leads to the release of reactive oxygen species. This could damage the ER or SR, leading to cell death, so in some embodiments the sAnk1-Killer Red protein could be used selectively to kill particular cell populations (e.g., in cancer, including cancers of muscle—rhabdomyosarcomas, for example).

In other embodiments, one can fuse sAnk1 with enzymes that could promote the phosphorylation or dephosphorylation of nearby proteins of the SR or ER (e.g., by introducing sequences at the C-terminus that contain such enzymatic activities, or sequences, such as those found in the AKAP family of proteins, that can bind such enzymes). Phosphorylation modulates the activity of SERCA and of the SR in a number of ways such that the modulation of the phosphorylation or dephosphorylation provides therapeutic benefit to an individual in need thereof.

In certain embodiments, the sAnk1 polypeptide, or the encoded sAnk1 polypeptide from the sAnk1 nucleic acid, may be modified compared to wild type. For example, in some embodiments modifications can affect the way sAnk1 interacts with SERCA and in other embodiments the modifications can affect its interactions with sarcolipin, and thus sarcolipin's interactions with SERCA. Site directed mutants of sAnk1 could therefore significantly improve its therapeutic efficacy. Site directed mutagenesis is routine in the art, but in specific embodiments the sequence of SEQ ID NO:1 or SEQ ID NO:3 is modified through a substitution, insertion, deletion, and so forth.

The nucleic acids of the disclosure, regardless of whether or not they encode a fusion protein may be labeled. The labels may be fluorescent, enzymatic, radioactive, or positron emitters. Fluorescent labels that may be used include, but are not limited to, BODIPY, Alexa Fluor, fluorescein, Oregon Green, tetramethylrhodamine, Texas Red, rhodamine, cyanine dye, or derivatives thereof. The labels may also more specifically be Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, DAPI, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, TET, Tetramethylrhodamine, and/or Texas Red. A labeling reagent is a composition that comprises a label and that can be incubated with the nucleic acid to effect labeling of the nucleic acid under appropriate conditions. In some embodiments, the labeling reagent comprises an alkylating agent and a dye, such as a fluorescent dye. In some embodiments, a labeling reagent comprises an alkylating agent and a fluorescent dye such as Cy3, Cy5, or fluorescein (FAM). In still further embodiments, the labeling reagent is also incubated with a labeling buffer, which may be any buffer compatible with physiological function (i.e., buffers that is not toxic or harmful to a cell or cell component) (termed "physiological buffer").

Embodiments of the disclosure concern nucleic acid compositions that directly or indirectly result in an increase in the level of sAnk1 in a cell. In specific embodiments, part or all of SEQ ID NO:1 or SEQ ID NO:3 is provided to an individual, and in some cases nucleic acid comprising part or all of SEQ ID NO:1 or SEQ ID NO:3 (respectively) is present in an expression vector. In certain embodiments, a fragment of SEQ ID NO:1 or SEQ ID NO:3 is provided to an individual, and the fragment may be of any functional size, such as at least 50, 75, 100, 125, 150, 175, 200, 225, 250, 275, 300, 325, 350, 375, or 400 nucleotides of SEQ ID NO:1 or SEQ ID NO:3, respectively. In any case, nucleic acid that is not identical to SEQ ID NO:1 or SEQ ID NO:3 may be provided to an individual, such as nucleic acid that has a certain percentage identity to SEQ ID NO:1 or SEQ ID NO:3, respectively. In particular embodiments, the nucleic acid may be at least 70, 75, 80, 85, 90, 95, 97, 98, or 99% identical to SEQ ID NO:1 or SEQ ID NO:3. The nucleic acid may be modified compared to SEQ ID NO:1 or SEQ ID NO:3, such as having a substitution, insertion, deletion, inversion, and so forth. The nucleic acid sequence of SEQ ID NO:1 or SEQ ID NO:3, or a suitable fragment thereof, may have operably linked thereto another sequence, such as one that encodes another protein entity, a label, and so forth.

Embodiments of the disclosure concern proteinaceous compositions that directly or indirectly result in an increase in the level of sAnk1 in a cell. In other embodiments, part or all of SEQ ID NO:2 is provided to an individual. In certain embodiments, a fragment of SEQ ID NO:2 is provided to an individual, and the fragment may be of any functional size, such as at least 25, 50, 75, 100, 125, or 150 amino acids of SEQ ID NO:2. In some cases, a polypeptide that is not identical to SEQ ID NO:2 is provided to an individual, such as polypeptide that has a certain percentage identity to SEQ ID NO:2. In certain embodiments, the polypeptide may be at least 70, 75, 80, 85, 90, 95, 97, 98, or 99% identical to SEQ ID NO:2. The polypeptide of SEQ ID NO:2, or a fragment thereof, may be modified compared to its corresponding wildtype sequence, such as having 1, 2, 3, 4, 5, 6, 7, 8, 9, 10, or more amino acid modifications compared to its corresponding wildtype sequence. The amino acid modification(s) may comprise an amino acid substitution, a deletion, an insertion, an inversion, or a combination thereof. Modifications can include post-translational modifications, such as glycosylation, phosphorylation, dephosphorylation, myristilation, ubiquitination, and so forth.

B. Decreasing sAnk1 Levels

In some embodiments, inhibition of sAnk1 achieves a therapeutic effect in an individual. The nucleic acid compositions that target sAnk1 mRNA may be of any length, so long as at least part of the composition hybridizes sufficiently and specifically to the sAnk1 mRNA molecule. The compositions may target any unique region of the sAnk1 mRNA. In specific embodiments, the nucleic acid compositions target a particular domain of the sAnk1 mRNA, including, for example, the transmembrane domain; the SERCA binding domain; a dimerization domain; an oligomerization domain; part or all of the N-terminal 29 amino acid hydrophobic sequence that targets proteins to and anchors them in the SR, the domain that binds SLN, and so forth. Embodiments of the disclosure concern compositions that directly or indirectly result in a decrease in the level of sAnk1 in a cell.

In specific embodiments, sAnk1 siRNAs are utilized to reduce sANK1 levels in muscle and/or brain cells. Given that only part of the cytoplasmic domain is unique to sAnk1, because the C-terminal 82 amino acids are also found in other forms of Ankyrin, in particular embodiments a common region with other forms of ankyrin is not targeted by a specific siRNA in methods of the disclosure.

siRNAs are small single or dsRNAs that do not significantly induce the antiviral response common among vertebrate cells but that do induce target mRNA degradation via the RNAi pathway. The term siRNA refers to RNA molecules that have either at least one double stranded region or at least one single stranded region and possess the ability to effect RNA interference (RNAi). It is specifically contemplated that siRNA may refer to RNA molecules that have at least one double stranded region and possess the ability to effect RNAi. The dsRNAs (siRNAs) may be generated by various methods including chemical synthesis, enzymatic synthesis of multiple templates, digestion of long dsRNAs by a nuclease with RNAse III domains, and the like. An "siRNA directed to" at least a particular region of sAnk1 means that a particular sAnk1 siRNA includes sequences that result in the reduction or elimination of expression of the target gene, i.e., the siRNA is targeted to the region or gene.

In some embodiments, the disclosure concerns an sAnk1 dsRNA or siRNA that is capable of triggering RNA interference, a process by which a particular RNA sequence is destroyed (also referred to as gene silencing). In specific embodiments, sAnk1 siRNA are dsRNA molecules that are 100 bases or fewer in length (or have 100 basepairs or fewer in its complementarity region). A dsRNA may be 15, 16, 17, 18, 19, 20, 21, 22, 23, 24, 25, 26, 27, 28, 29, 30, 40, 50, 60, 70, 80, 90, 100 110, 120, 130, 140, 150, 160, 170, 180, 190, 200, 225, 250, 275, 300, 325, 350, 375, 400, 450, 500, 550, 600, 650, 700, 750, 800, 850, 900, 950, or 1000 nucleotides or more in length. In certain embodiments, sAnk1 siRNA may be approximately 21 to 25 nucleotides in length. In some cases, it has a two nucleotide 3' overhang and a 5' phosphate. The particular sAnk1 RNA sequence is targeted as a result of the complementarity between the dsRNA and the particular sAnk1 RNA sequence. It will be understood that dsRNA or siRNA of the disclosure can effect at least a 20, 30, 40, 50, 60, 70, 80, 90 percent or more reduction of expression of a targeted sAnk1 RNA in a muscle cell and/or brain cell. dsRNA of the invention (the term "dsRNA" will be understood to include "siRNA" and/or "candidate siRNA") is distinct and distinguishable from antisense and ribozyme molecules by virtue of the ability to trigger RNAi. Structurally, dsRNA molecules for RNAi differ from antisense and ribozyme molecules in that dsRNA has at least one region of complementarity within the RNA molecule. The complementary (also referred to as "complementarity") region comprises at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, or 500 contiguous bases. In some embodiments, long dsRNA are employed in which "long" refers to dsRNA that are 1000 bases or longer (or 1000 basepairs or longer in complementarity region). The term "dsRNA" includes "long dsRNA", "intermediate dsRNA" or "small dsRNA" (lengths of 2 to 100 bases or basepairs in complementarity region) unless otherwise indicated. In some embodiments of the disclosure, dsRNA can exclude the use of siRNA, long dsRNA, and/or "intermediate" dsRNA (lengths of 100 to 1000 bases or basepairs in complementarity region).

It is specifically contemplated that a dsRNA may be a molecule comprising two separate RNA strands in which one strand has at least one region complementary to a region on the other strand. Alternatively, a dsRNA includes a molecule that is single stranded yet has at least one complementarity region as described above (such as when a single strand with a hairpin loop is used as a dsRNA for RNAi). For convenience, lengths of dsRNA may be referred to in terms of bases, which simply refers to the length of a single strand or in terms of basepairs, which refers to the length of the complementarity region. It is specifically contemplated that embodiments discussed herein with respect to a dsRNA comprised of two strands are contemplated for use with respect to a dsRNA comprising a single strand, and vice versa. In a two-stranded dsRNA molecule, the strand that has a sequence that is complementary to the targeted mRNA is referred to as the "antisense strand" and the strand with a sequence identical to the targeted mRNA is referred to as the "sense strand." Similarly, with a dsRNA comprising only a single strand, it is contemplated that the "antisense region" has the sequence complementary to the targeted mRNA, while the "sense region" has the sequence identical to the targeted mRNA. Furthermore, it will be understood that sense and antisense region, like sense and antisense strands, are complementary (i.e., can specifically hybridize) to each other.

Strands or regions that are complementary may or may not be 100% complementary ("completely or fully complementary"). It is contemplated that sequences that are "complementary" include sequences that are at least 50% complementary, and may be at least 50%, 60%, 70%, 80%, or 90% complementary. In some embodiments, siRNA generated from sequence based on one organism may be used in a different organism to achieve RNAi of the cognate target gene. In other words, siRNA generated from a dsRNA that corresponds to a human gene may be used in a mouse cell if there is the requisite complementarity, as described above. Ultimately, the requisite threshold level of complementarity to achieve RNAi is dictated by functional capability. It is specifically contemplated that there may be mismatches in the complementary strands or regions. Mismatches may number at most or at least 1, 2, 3, 4, 5, 6, 7, 8, 9, 10, 11, 12, 13, 14, 15, 16, 17, 18, 19, 20, 21, 22, 23, 24, 25 residues or more, depending on the length of the complementarity region.

The single RNA strand or each of two complementary double strands of a dsRNA molecule may be of at least or at most the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, or more (including the full-length of a particular's gene's mRNA without the poly-A tail) bases or basepairs. If the dsRNA is composed of two separate strands, the two strands may be the same length or different lengths. If the dsRNA is a single strand, in addition to the complementarity region, the strand may have 1, 2, 3, 4, 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more bases on either or both ends (5' and/or 3') or as forming a hairpin loop between the complementarity regions.

In some embodiments, the strand or strands of dsRNA are 100 bases (or basepairs) or less. In specific embodiments the strand or strands of the dsRNA are less than 70 bases in length. With respect to those embodiments, the dsRNA strand or strands may be from 5-70, 10-65, 20-60, 30-55, 40-50 bases or basepairs in length. A dsRNA that has a complementarity region equal to or less than 30 basepairs (such as a single stranded hairpin RNA in which the stem or complementary portion is less than or equal to 30 basepairs) or one in which the strands are 30 bases or fewer in length is specifically contemplated, as such molecules evade a mammalian's cell antiviral response. Thus, a hairpin dsRNA (one strand) may be 70 or fewer bases in length with a complementary region of 30 basepairs or fewer. In some cases, a dsRNA may be processed in the cell into siRNA.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the disclosure can comprise a 3' overhang. As used herein, a "3' overhang"

refers to at least one unpaired nucleotide extending from the 3'-end of a duplexed RNA strand.

Thus in one embodiment, the sAnk1 siRNA of the invention comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

In the embodiment in which both strands of the sAnk1 siRNA molecule comprise a 3' overhang, the length of the overhangs can be the same or different for each strand. In a most preferred embodiment, the 3' overhang is present on both strands of the siRNA, and is 2 nucleotides in length. For example, each strand of the sAnk1 siRNA of the invention can comprise 3' overhangs of dithymidylic acid ("TT") or diuridylic acid ("uu").

In order to enhance the stability of the present sAnk1 siRNA, the 3' overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

In certain embodiments, the sAnk1 siRNA of the disclosure comprises the sequence AA(N19)TT or NA(N21), where N is any nucleotide. These sAnk1 siRNA comprise approximately 30-70% GC, and preferably comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another embodiment, the sAnk1 siRNA of the invention comprises the sequence NAR(N17)YNN, where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

The sAnk1 siRNA of the disclosure can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Gottingen, Germany, and can be found by accessing the website of the Max Planck Institute and searching with the keyword "siRNA." Thus, the sense strand of the present siRNA comprises a nucleotide sequence identical to any contiguous stretch of about 19 to about 25 nucleotides in the target mRNA.

Generally, a target sequence on the target mRNA can be selected from a given cDNA sequence corresponding to the sAnk1 mRNA, preferably beginning 50 to 100 nt downstream (i.e., in the 3' direction) from the start codon. The target sequence can, however, be located in the 5' or 3' untranslated regions, or in the region nearby the start codon.

In certain embodiments, sAnk1 small hairpin RNA or short hairpin RNA (shRNA) is utilized; shRNA is an artificial RNA molecule with a tight hairpin turn that can be used to silence target gene expression via RNA interference (RNAi). In certain cases, expression of sAnk1 shRNA in cells is achieved through delivery of non-viral vectors (such as plasmids or bacterial vectors) or through viral vectors. shRNA is useful because it has a relatively low rate of degradation and turnover.

Furthermore, it is contemplated that any compositions, including a siRNA (or the longer dsRNA template) or a sRNA-encoding nucleic acid may be labeled. The label may be fluorescent, radioactive, enzymatic, or calorimetric. It is contemplated that a dsRNA may have one label attached to it or it may have more than one label attached to it. When more than one label is attached to a dsRNA, the labels may be the same or be different. If the labels are different, they may appear as different colors when visualized. The label may be on at least one end and/or it may be internal. Furthermore, there may be a label on each end of a single stranded molecule or on each end of a dsRNA made of two separate strands. The end may be the 3' and/or the 5' end of the nucleic acid. A label may be on the sense strand or the sense end of a single strand (end that is closer to sense region as opposed to antisense region), or it may be on the antisense strand or antisense end of a single strand (end that is closer to antisense region as opposed to sense region). In some cases, a strand is labeled on a particular nucleotide (G, A, U, or C). When two or more differentially colored labels are employed, fluorescent resonance energy transfer (FRET) techniques may be employed to characterize the dsRNA.

Labels contemplated for use in several embodiments are non-radioactive. In many embodiments of the invention, the labels are fluorescent, though they may be enzymatic, radioactive, or positron emitters. Fluorescent labels that may be used include, but are not limited to, BODIPY, Alexa Fluor, fluorescein, Oregon Green, tetramethylrhodamine, Texas Red, rhodamine, cyanine dye, or derivatives thereof. The labels may also more specifically be Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, DAPI, 6-FAM, Killer Red, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAN/IRA, TET, Tetramethylrhodamine, and/or Texas Red. A labeling reagent is a composition that comprises a label and that can be incubated with the nucleic acid to effect labeling of the nucleic acid under appropriate conditions. In some embodiments, the labeling reagent comprises an alkylating agent and a dye, such as a fluorescent dye. In some embodiments, a labeling reagent comprises an alkylating agent and a fluorescent dye such as Cy3, Cy5, or fluorescein (FAM). In still further embodiments, the labeling reagent is also incubated with a labeling buffer, which may be any buffer compatible with physiological function (i.e., buffers that is not toxic or harmful to a cell or cell component) (termed "physiological buffer").

In some embodiments of the invention, a dsRNA has one or more non-natural nucleotides, such as a modified residue or a derivative or analog of a natural nucleotide. Any modified residue, derivative or analog may be used to the extent that it does not eliminate or substantially reduce (by at least 50%) RNAi activity of the dsRNA.

A person of ordinary skill in the art is well aware of achieving hybridization of complementary regions or molecules. Such methods typically involve heat and slow cooling of temperature during incubation, for example.

In various embodiments, sAnk1 siRNAs are encoded by expression constructs. The expression constructs may be obtained and introduced into a cell. Once introduced into the cell the expression construct is transcribed to produce various siRNAs. Expression constructs include nucleic acids that provide for the transcription of a particular nucleic acid. Expression constructs include plasmid DNA, linear expression elements, circular expression elements, viral expression constructs (including adenoviral, adeno-associated viral, retroviral, lentiviral, and so forth), and the like, all of which are contemplated as being used in the compositions and methods of the present disclosure. In certain embodiments one or at least 2, 3, 4, 5, 6, 7, 8, 9, 10 or more sAnk1 siRNA molecules are encoded by a single expression construct. Expression of the sAnk1 siRNA molecules may be independently controlled by at least 2, 3, 4, 5, 6, 7, 8, 9, 10 or more regulatory elements, including muscle-specific or brain-specific regulatory elements. In certain embodiments, at least 2, 3, 4, 5, 6, 7, 8, 9, 10 or more expression constructs may introduced into the cell. Each expression construct may encode 1, 2, 3, 4, 5, 6, 7, 8, 9, 10 or more sAnk1 siRNA molecules. In certain embodiments, siRNA molecules may be encoded as expression domains. Expression domains include a transcription control element, which may or may not be independent of other control or promoter elements; a nucleic acid encoding an siRNA; and optionally a transcriptional termination element.

The nucleotide sequence of the siRNA is defined by the nucleotide sequence of its target gene. The sAnk1 siRNA contains a nucleotide sequence that is essentially identical to at least a portion of the target gene. Preferably, the siRNA contains a nucleotide sequence that is completely identical to at least a portion of the sAnk1 gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

A sAnk1 siRNA comprises a double stranded structure, the sequence of which is "substantially identical" to at least a portion of the target gene. "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated by standard practices in the art.

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. It is preferred that there be 100% sequence identity between the dsRNA for use as siRNA and at least 15 contiguous nucleotides of the target gene, although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

In some methods of the disclosure, sAnk1 siRNA molecules or template nucleic acids may be isolated or purified prior to their being used in a subsequent step. sAnk1 siRNA molecules may be isolated or purified prior to introduction into a cell. "Introduction" into a cell includes known methods of transfection, transduction, infection and other methods for introducing an expression vector or a heterologous nucleic acid into a cell. A template nucleic acid or amplification primer may be isolated or purified prior to it being transcribed or amplified. Isolation or purification can be performed by a number of methods known to those of skill in the art with respect to nucleic acids. In some embodiments, a gel, such as an agarose or acrylamide gel, is employed to isolate the sAnk1 siRNA.

In some methods of the disclosure, dsRNA is obtained by transcribing each strand of the dsRNA from one or more cDNA (or DNA or RNA) encoding the strands in vitro. It is contemplated that a single template nucleic acid molecule may be used to transcribe a single RNA strand that has at least one region of complementarity (and is thus double-stranded under conditions of hybridization) or it may be used to transcribe two separate complementary RNA molecules. Alternatively, more than one template nucleic acid molecule may be transcribed to generate two separate RNA strands that are complementary to one another and capable of forming a dsRNA. Additional methods involve isolating the transcribed strand(s) and/or incubating the strand(s) under conditions that allow the strand(s) to hybridize to their complementary strands (or regions if a single strand is employed).

In other embodiments, antibodies are utilized to reduce activity of sAnk1. As used herein, the term "antibody" includes any immunologic binding agent, such as IgG, IgM, IgA, IgD and IgE. Generally, IgG and/or IgM may be utilized because they are the most common antibodies in the physiological situation and because they are most easily made in a laboratory setting. The term "antibody" may be used to refer to any antibody-like molecule that has an antigen binding region, and includes antibody fragments such as Fab', Fab, F(ab')$_2$, single domain antibodies (DABs), Fv, scFv (single chain Fv), and the like. Monoclonal and humanized anitbodies are also contemplated in the disclosure.

III. Exemplary Vectors

Nucleic acids of the invention, particularly DNA templates or DNA constructs for sAnk1 overexpression or sAnk1 siRNA expression, may be produced recombinantly. Protein and polypeptides may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (2001) and Ausubel et al., 1994, both incorporated by reference. A vector may encode non-template sequences such as a tag or label. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

A DNA construct refers to a plasmid, viral DNA, or linear DNA molecule bearing a sAnk1 sequence or a sAnk1 siRNA sequence that is expressed by an adjacent or otherwise upstream RNA polymerase promoter element. The promoter element (which may also be referred to as a regulatory region) may be constitutive, tissue-specific, or both. In the case of sAnk1 siRNAs, the expression of siRNAs from DNA constructs has primarily been via RNA polymerase III (Brummelkamp et at 2002 and Paddison et al. 2002), though there may be expression of functional siRNAs from an RNA Polymerase II promoter (Xia et at 2002). SiRNA cocktails can be generated in mammalian cells if one or more DNA constructs bearing one or more sAnk1 siRNA expression domains are transfected or transduced into cells.

The term "expression vector" or "expression construct" refers to a vector or construct containing a nucleic acid sequence coding for at least part of a gene product capable of being transcribed (although in the case of siRNA embodiments, these sequences are not translated). Expression vectors can contain a variety of "regulatory sequences" or "control sequences," which refer to nucleic acid sequences necessary for the transcription of an operably linked coding sequence in a particular host organism. In addition to control sequences that govern transcription and translation, vectors and expression vectors may contain nucleic acid sequences that serve other functions as well and are described infra.

The term "expression domain" refers to parts of an expression construct that include a promoter element operatively linked to a nucleic acid sequence coding for all or at least part of sAnk1 or a sAnk1 siRNA. As used herein, an expression construct may contain 1, 2, 3, 4, 5, 6, 7, 8, 9, 10 or more expression domains each of which may or may not be independently transcribed. An expression construct containing multiple expression domains may contain 1, 2, 3, 4, 5, 6, 7, 8, 9, 10 or more of the same or 1, 2, 3, 4, 5, 6, 7, 8, 9, 10 or more different siRNAs and combinations thereof.

A "regulatory region" (which may also be referred to as a "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A regulatory region may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter (examples include the bacterial promoters SP6, T3, and T7), which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression, such as muscle cells or brain cells. Those of skill in the art of molecular biology generally know the use of promoters, enhancers, and cell type combinations for protein or RNA expression, for example, see Sambrook et al. (2001), incorporated herein by reference. The promoters employed may be constitutive, tissue-specific, inducible, and/or useful under the appropriate conditions to direct high level expression from the introduced DNA segment. The promoter may be heterologous or endogenous.

Other elements of a vector are well known to those of skill in the art. A vector may include a polyadenylation signal, an initiation signal, an internal ribosomal binding site, a multiple cloning site, a selective or screening marker, a termination signal, a splice site, an origin of replication, or a combination thereof.

The sAnk1-encoding nucleic acid or the sAnk1 siRNA of the disclosure can be expressed from recombinant viral vectors intracellularly at or near the area of interest in vivo (such as within the muscle tissue or brain, respectively) The recombinant viral vectors of the disclosure comprise sequences encoding the sAnk1-encoding nucleic acid or the sAnk1 siRNA of the disclosure and any suitable promoter for expressing the sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the sAnk1-encoding nucleic acid or the sAnk1 siRNA in a particular tissue (for example, muscle or brain) or in a particular intracellular environment. The use of recombinant viral vectors to deliver sAnk1-encoding nucleic acid or sAnk1 siRNA of the disclosure to cells in vivo is known in the art.

In cases where siRNA is employed, sAnk1 siRNA of the disclosure can be expressed from a recombinant viral vector either as two separate, complementary RNA molecules, or as a single RNA molecule with two complementary regions.

Any viral vector capable of accepting the coding sequences for the sAnk1-encoding nucleic acid or the sAnk1 siRNA molecule(s) to be expressed can be used, for example vectors derived from adenovirus (AV); adeno-associated virus (AAV; including AAV serotypes that are especially useful for muscle: AAV6, AAV8 and AAV9); retroviruses (e.g, lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, methods for inserting nucleic acid sequences for expressing the sAnk1-encoding nucleic acids or sAnk1 siRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; and Anderson W F (1998), Nature 392: 25-30, the entire disclosures of which are herein incorporated by reference.

Preferred viral vectors are those derived from AV and AAV. In a particularly preferred embodiment, the sAnk1 siRNA of the disclosure is expressed as two separate, complementary single-stranded RNA molecules from a recombinant AAV vector comprising, for example, either the U6 or H1 RNA promoters, or the cytomegalovirus (CMV) promoter. In cases where sAnk1-encoding nucleic acid is employed, the nucleic acid is expressed from a recombinant AAV vector comprising, for example, the cytomegalovirus (CMV) promoter, or muscle-specific or brain-specific promoters, for example.

A suitable AV vector for expressing the sAnk1 siRNA of the disclosure (or the sAnk1-encoding nucleic acids), a method for constructing the recombinant AV vector, and a method for delivering the vector into target cells, are described in Xia H et al. (2002), Nat. Biotech. 20: 1006-1010. Suitable AAV vectors for expressing the nucleic acids of the disclosure, methods for constructing the recombinant AAV vector, and methods for delivering the vectors into target cells are described in Samulski R et al. (1987), J. Virol. 61: 3096-3101; Fisher K J et al. (1996), J. Virol., 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

The ability of a sAnk1 siRNA containing a given target sequence to cause RNAi-mediated degradation of the target mRNA can be evaluated using standard techniques for measuring the levels of RNA or protein in cells. For example, sAnk1 siRNA of the invention can be delivered to cultured cells, and the levels of target mRNA can be measured by Northern blot or dot blotting techniques, or by quantitative RT-PCR. Alternatively, the levels of sAnk1 protein in the cultured cells can be measured by ELISA or Western blot. A suitable cell culture system for measuring the effect of the present siRNA on target mRNA or protein levels may be utilized. RNAi-mediated degradation of sAnk1 mRNA by an siRNA containing a given target sequence can also be evaluated with animal models, for example.

As discussed above, the sAnk1 siRNA of the disclosure target and cause the RNAi-mediated degradation of sAnk1 mRNA, or alternative splice forms, mutants or cognates thereof. Degradation of the sAnk1 mRNA by a sAnk1-directed siRNA reduces the production of a functional gene product from the sAnk1 gene. Thus, the disclosure provides a method of inhibiting expression of sAnk1 in an individual, comprising administering an effective amount of an sAnk1 siRNA of the invention to the individual, such that the target mRNA is degraded.

IV. Delivery and Pharmaceutical Compositions

In methods of the disclosure, the present sAnk1 siRNA or sAnk1-encoding nucleic acids can be administered to the subject either as naked nucleic acid, in conjunction with a delivery reagent, or as a recombinant plasmid or viral vector that expresses the nucleic acids. Delivery of the sAnk1 siRNA molecules or the sAnk1-encoding nucleic acids to an individual may occur by any suitable means, but in specific embodiments it occurs by one of the following: cyclodextrin delivery system; ionizable lipids; DPC conjugates; GalNAc-conjugates; self-assembly of oligonucleotide nanoparticles (DNA tetrahedra carrying multiple siRNAs); or polymeric nanoparticles made of low-molecular-weight polyamines and lipids (see Kanasty et al. Nature Materials 12, 967-977 (2013) for review of same).

Suitable delivery reagents for administration in conjunction with the present sAnk1 siRNA or sAnk1-encoding nucleic acids include at least the Minis Transit TKO lipophilic reagent; lipofectin; lipofectamine; cellfectin; or polycations (e.g., polylysine), or liposomes. In specific embodiments, a particular delivery reagent comprises a liposome.

Liposomes can aid in the delivery of the sAnk1-encoding nucleic acids or the sAnk1 siRNA to a particular tissue, such as muscle or brain tissue, and can also increase the blood half-life of the nucleic acids. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), Ann. Rev. Biophys. Bioeng. 9: 467; and U.S. Pat. Nos. 4,235,871, 4,501,728, 4,837,028, and 5,019,369, the entire disclosures of which are herein incorporated by reference.

In certain aspects, the liposomes encapsulating the sAnk1 siRNA or sAnk1-encoding nucleic acids comprises a ligand molecule that can target the liposome to a particular cell or tissue at or near the site of interest. Ligands that bind to receptors prevalent in the tissues to be targeted by the RNA or siRNA, such as monoclonal antibodies that bind to surface antigens, are contemplated. In particular cases, the liposomes encapsulating the sAnk1 siRNA or sAnk1-encoding nucleic acids are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand. Opsonization-inhibiting moieties for use in preparing the liposomes of the disclosure are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MIMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example solid tumors, will efficiently accumulate these liposomes; see Gabizon, et al. (1988), P.N.A.S., USA, 18: 6949-53. In addition, the reduced uptake by the RES lowers the toxicity of stealth liposomes by preventing significant accumulation in the liver and spleen. Thus, liposomes of the invention that are modified with opsonization-inhibition moieties can deliver the present siRNA to tumor cells.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes." The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60 degrees C.

Recombinant plasmids that express nucleic acids of the disclosure are discussed above. Such recombinant plasmids can also be administered directly or in conjunction with a suitable delivery reagent, including the Minis Transit LT1 lipophilic reagent; lipofectin; lipofectamine; cellfectin; polycations (e.g., polylysine) or liposomes. Recombinant viral vectors that express sAnk1 siRNA or sAnk1-encoding nucleic acids are provided herein, and methods for delivering such vectors to an area of interest in an individual are within the skill in the art.

The sAnk1 siRNA or sAnk1-encoding nucleic acids of the disclosure can be administered to the subject by any means suitable for delivering the siRNA to the cells of the tissue at or near the area of need. For example, the sAnk1 siRNA or sAnk1-encoding nucleic acids can be administered by gene gun, electroporation, or by other suitable parenteral or enteral administration routes, or by injection, for example, by intramuscular or intravenous injection. In embodiments wherein composition(s) are delivered to the brain, one either inject into the ventricles or local injection into particular brain regions, for example.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intra-retinal injection or subretinal injection); subcutaneous injection or deposition including subcutaneous infusion (such as by osmotic pumps); direct (e.g., topical) application to the area at or near the site of interest, for example by a catheter or other placement device (e.g., a corneal pellet or a suppository, eye-dropper, or an implant comprising a porous, non-porous, or gelatinous material); and inhalation. In a particular embodiment, injections or infusions of the composition(s) are given at or near the site of muscular atrophy or disease.

The sAnk1 siRNA or the sAnk1-encoding nucleic acids or the sAnk1 polypeptides or peptides of the disclosure can be administered in a single dose or in multiple doses. Where the administration of a composition is by infusion, the infusion can be a single sustained dose or can be delivered by multiple infusions. Injection of the agent directly into the tissue is at or near the site of need. Multiple injections of the agent into the tissue at or near the site of interest are encompassed within this disclosure.

One skilled in the art can also readily determine an appropriate dosage regimen for administering the sAnk1 siRNA, sAnk1-encoding nucleic acids, sAnk1 polypepides or peptides of the invention to a given subject. For example, the composition(s) can be administered to the subject once, such as by a single injection or deposition at or near the site of interest. Alternatively, the composition(s) can be administered to a subject once or twice daily to a subject once weekly for a period of from about three to about twenty-eight days, more preferably from about seven to about ten weeks. In a preferred dosage regimen, the composition(s) is injected at or near the site of interest once a day for seven days. Where a dosage regimen comprises multiple administrations, it is understood that the effective amount of composition(s) administered to the subject can comprise the total amount of composition(s) administered over the entire dosage regimen.

The composition(s) of the disclosure may be formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

In particular aspects, the present pharmaceutical formulations comprise a composition(s) of the disclosure (e.g., 0.1 to 90% by weight), or a physiologically acceptable salt thereof, mixed with a physiologically acceptable carrier medium. Preferred physiologically acceptable carrier media are water, buffered water, 0.4% saline, 0.3% glycine, hyaluronic acid and the like.

Pharmaceutical compositions of the disclosure can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like. For example, a solid pharmaceutical composition for oral administration can comprise any of the carriers and excipients listed above and 10-95%, preferably 25%-75%, of one or more compositions of the invention. A pharmaceutical composition for aerosol (inhalational) administration can comprise 0.01-20% by weight, preferably 1%-10% by weight, of one or more compositions of the invention encapsulated in a liposome as described above, and propellant. A carrier can also be included as desired; e.g., lecithin for intranasal delivery.

V. Exemplary Methods of Use

Many forms of muscle disease in humans are linked to changes in the ability of the muscle fibers to regulate cytoplasmic levels of calcium ions. SERCA is a key player in this regulation, and its activity is itself subject to careful regulation. To date, the most studied mechanisms responsible for regulating SERCA activity have been those mediated by SLN and PLN. The disclosure herein shows that sAnk1 also regulates SERCA activity and that it limits the regulatory activity of SLN. The data also show that changes in sAnk1 are associated at least with skeletal muscle pathology.

Because of its novel actions, in specific embodiments modulation of sAnk1 levels in muscle, such as heart or skeletal muscle, are utilized to regulate SERCA activity, restoring calcium homeostasis in muscle to normal, and thereby maintaining muscle health. As sAnk1 is expressed in heart and skeletal muscle, in particular embodiments it is useful in both types of tissue. Measures to regulate SERCA activity include transduction (such as viral transduction) or by pharmacologic means, in certain cases, using compositions related to sAnk1.

Methods of regulating the cytosolic calcium level in any cell of the mammalian individual are encompassed in the disclosure. In specific embodiments, the reduction in cytosolic calcium levels occurs upon delivery of compositions that inhibit the activity and/or level of sAnk1. In other embodiments the increase in cytosolic calcium levels occurs upon delivery of compositions that enhance the activity and/or level of sAnk1. The cells may be any cells in the body, but in specific embodiments the cells are muscle cells and/or brain cells.

Embodiments of the disclosure concern methods that modulate cytoplasmic calcium to achieve a therapeutic effect for an individual in need thereof, wherein the individual has defective regulation of cytoplasmic calcium as part of the etiology and/or symptom of a medical condition. In specific embodiments, the medical condition includes aberrant cellular calcium levels in muscle cells and/or brain cells. In cases wherein muscle cells may be affected in a medical condition, the muscle cells may be of any type, including cardiac, smooth, or skeletal.

In certain embodiments, there is a method of treating an individual with an effective amount of a composition that increases cellular level of sAnk1 and/or enhances its activity, wherein the individual has a medical condition for which the composition is therapeutic. The individual may have a medical condition that is caused by and/or has as a symptom one or more muscular defects, such as a form of muscular dystrophy. In certain embodiments, the muscular defect is directly or indirectly related to aberrant calcium levels in muscle cells of the defective tissue. One can measure aberrant calcium levels in an individual before and/or after treatment by routine methods in the art. For example, reducing the level of sAnk1 could increase the inhibition of SERCA by SLN in atrial muscle, which can be reduced in cases of atrial fibrillation. As another example, enhancing the level of sAnk1 could reduce the pathological levels of calcium in the cytoplasm of individuals with Duchenne muscular dystrophy by inhibiting SLN's effects on SERCA.

In certain embodiments, there is a method of treating an individual with an effective amount of an inhibitor of sAnk1 expression and/or activity, wherein the individual has a medical condition for which the inhibitor is therapeutic. The individual may have a medical condition that is caused by and/or has as a symptom one or more muscular defects, such as muscular atrophy. In certain embodiments, the muscular defect is directly or indirectly related to aberrant calcium levels in muscle cells of the defective tissue. One can measure aberrant calcium levels in an individual before and/or after treatment by routine methods in the art. In at least some cases, samples, such as biopsies, can be obtained from the individual and analyzed for calcium content. However, biopsies can also be examined for morphological and/or biochemical markers of disease to determine if the sAnk1-related treatment was effective. Alternatively, biomarkers in serum could be used for this purpose in those cases where one or more appropriate biomarkers for disease progression are known.

sAnk1 is also present in the brain, where in specific embodiments it has similar activities to those in muscle cells. As calcium homeostasis is essential for neuronal health, certain cognitive functions, such as memory, learning, perception, thinking, and reasoning, for example, may be improved by addressing the role of sAnk 1 in the central nervous system, such as through its enhancement or inhibition. An individual that has defective cognitive function may be treated with compositions of the disclosure. An individual treated with methods of the disclosure can be tested for cognitive function before, during, and/or after treated with compositions of the disclosure. Cognitive function tests are known in the art and may be given to an individual known or suspected of defective cognitive function.

Exemplary methods include the Screening Examination for Cognitive Impairment (SEFCI), the Repeatable Battery for the Assessment of Neuropsychological Status (RBANS), Rao's Brief Repeatable Battery (BRB), the complete SEP-59 Questionnaire, Selective Reminding Test, Symbol Digit Modalities Test (SDMT), Similarities Subtest, PASAT, Stroop Test, Myers-Briggs Type Indicator, Mini-Mental State Examination, and/or the PROSPER test. In other embodiments, the individual has Alzheimer's Disease, Parkinson's Disease, multiple sclerosis, Down's Syndrome, mental retardation, Autism Spectrum Disorder, Post-traumatic stress disorder, Cerebral palsy, stroke, brain damage, head injury, brain diseases, tertiary syphilis, liver disease, kidney disease, alcoholism, thyroid deficiency, muscular dystrophy, severe malnutrition, psychoses, drug abuse, meningitis, encephalitis, brain blood clot, cerebral tumor, cerebral abscess, lead poisoning, severe hypoglycemia, insulin overdosing, degenerative diseases of the nervous system, metabolic diseases, multiple infarct dementia, hypothyroidism, normal pressure hydrocephalus, vitamin B12 deficiency, lysosomal storage disease, chemotherapy, spastic quadriplegia, encephalitis, brain abscess, fetal alcohol syndrome, or is elderly.

In some embodiments, there are methods of increasing expression or levels of sAnk1 in a muscle cell and/or brain cells. Such methods may involve the compositions related to sAnk1-encoding nucleic acids and/or sAnk1 polypeptides or peptides. In particular embodiments, the present disclosure is directed to compositions that increase the intracellular level of sAnk1.

In other embodiments of the disclosure, there are methods of reducing the expression of sAnk1 in a muscle cell and/or a brain cell. Such methods may involve the compositions related to dsRNA and siRNA, as described above. In particular embodiments, the present disclosure is directed to sAnk1 siRNAs that specifically target and cause RNAi-induced degradation of sAnk1 mRNA. In some cases, compositions and methods comprising siRNA targeted to sAnk1 are advantageously used to alter cytoplasmic calcium levels, in particular for the treatment of medical conditions that comprise excessive cytoplasmic calcium levels. The siRNA of the disclosure are believed to cause the RNAi-mediated degradation of sAnk1 mRNAs, so that the protein product of the sAnk1 gene is not produced or is produced in reduced amounts. In some cases, because sAnk1 binding to SERCA directly or indirectly results in an increase in calcium levels, the sAnk1 siRNA-mediated degradation of sAnk1 mRNA reduces excessive calcium levels. Although sAnk1 inhibits SERCA, sAnk1 also promotes greater SERCA activity when SLN is present than when SERCA and SLN are present alone. So, in embodiments wherein there is no SLN in a desired tissue that is targeted to overexpress sAnk1, there will be inhibition of SERCA and an increase in cytoplasmic Ca (in specific embodiments). In embodiments wherein there is SLN in the tissue, then cytoplasmic Ca will already be high and sAnk1 will reduce it. In cases wherein sAnk1 is expressed endogenously in the tissue of interest, knockdown of sAnk1 with siRNA will have the opposite effects to sAnk1 overexpression.

Embodiments of the disclosure include methods of treating an individual that has dysfunctional cytoplasmic calcium level at least in muscle cells and/or brain cells. In specific embodiments, the individual has cardiomyopathy, muscular dystrophy, skeletal myopathies, and so forth. In some embodiments, the individual has a neurodegenerative disease that is linked to changes in cytoplasmic calcium, such as Alzheimer's.

One skilled in the art can readily determine an effective amount of the sAnk1-encoding nucleic acids or sAnk1 polypeptides/peptides or sAnk1 siRNA of the disclosure to be administered to a given individual, by taking into account factors such as the size and weight of the subject; the extent of the particular medical condition; the age, health and sex of the subject; the route of administration; and whether the administration is regional or systemic. Generally, in specific embodiments an effective amount of the sAnk1-encoding nucleic acids or sAnk1 siRNA of the disclosure comprises an intercellular concentration at or near the site of interest from about 1 nanomolar (nM) to about 100 nM, preferably from about 2 nM to about 50 nM, more preferably from about 2.5 nM to about 10 nM. It is contemplated that greater or lesser amounts of sAnk1-encoding nucleic acids or siRNA can be administered.

In particular embodiments, methods of the disclosure further include determination that an individual has a certain medical condition that would be treated by the sAnk1-encoding nucleic acids or sAnk1 polypeptides/peptides or sAnk1 siRNA compositions of the disclosure. For example, an individual may be diagnosed with a muscle-related medical condition or a brain-related medical condition using routine methods in the art. The treatment regimen for the individual may be performed by an individual or entity other than the one that detected the medical condition. The individual may be treated with compositions of the disclosure regardless of whether or not aberrant cellular calcium levels have been determined in the individual.

VI. Kits of the Disclosure

Any of the compositions described herein may be comprised in a kit. In a non-limiting example, reagents for generating or assembling the sAnk1-encoding nucleic acids or sAnk1 polypeptides/peptides or sAnk1 siRNA are included in a kit. The kit may further or alternatively include nucleic acid constructs that can be transfected or transduced into cells of interest. Vectors of any kind may be included. The kit may also comprise reagents for creating or synthesizing dsRNA. It may also include one or more buffers, such as a nuclease buffer, transcription buffer, or a hybridization buffer, compounds for preparing the DNA template or the dsRNA, and components for isolating the resultant template, dsRNA, or siRNA. In some cases, the kit comprises a generated sAnk1 siRNA composition ready for delivery, although it may or may not need to be dispersed in a carrier, for example. In other embodiments the kit comprises the fully generated sAnk1-encoding nucleic acids or sAnk1 polypeptides/peptides that may or may not be dispersed in a carrier.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

Such kits may also include components that facilitate isolation of a DNA construct, DNA template, long dsRNA, or siRNA. It may also include components that preserve or maintain the nucleic acids or that protect against their degradation. Such components may be RNAse-free or protect against RNAses, such as RNase inhibitors. Such kits generally will comprise, in suitable means, distinct containers for each individual reagent or solution.

A kit may also include instructions for employing the kit components, as well the use of any other reagent not included in the kit. Instructions may include variations that can be implemented.

EXAMPLES

The following examples are presented in order to more fully illustrate the preferred embodiments of the disclosure. They should in no way, however, be construed as limiting the broad scope of the disclosure.

Example 1

General Overview

Small Ankyrin 1 (sAnk1) is an approximately 17 kDa transmembrane (TM) protein that binds to the cytoskeletal protein, obscurin, and stabilizes the network sarcoplasmic reticulum (nSR) in skeletal muscle. As shown herein, sAnk1 shares homology in its TM amino acid sequence with sarcolipin, a small protein inhibitor of the sarco(endo)plasmic reticulum $Ca^{2+}$-ATPase (SERCA). Herein it was shown that sAnk1 interacts specifically with SERCA1 in SR vesicles isolated from rabbit skeletal muscle, and in COS7 cells transfected to express these proteins. This interaction was demonstrated by co-immunoprecipitation (coIP) and an anisotropy-based FRET method (AFRET). Binding was reduced approximately two-fold by the replacement of all the TM amino acids of sAnk1 with leucines by mutagenesis. This indicates that, like sarcolipin, sAnk1 interacts with SERCA1 at least in part via its TM domain. Binding of the cytoplasmic domain of sAnk1 to SERCA1 was also detected in vitro. ATPase activity assays show that co-expression of sAnk1 with SERCA1 leads to a reduction of SERCA1's apparent $Ca^{2+}$ affinity, but that sAnk1's effect is less than that of sarcolipin. The sAnk1 TM mutant has no effect on SERCA1 activity. The results indicate that sAnk1 interacts with SERCA1 through its TM and cytoplasmic domains to regulate SERCA1 activity and modulate sequestration of $Ca^{2+}$ in the SR lumen, in embodiments of the disclosure. The identification of sAnk1 as a novel regulator of SERCA1 has significant implications for muscle physiology and the development of therapeutic approaches at least to treat heart failure and muscular dystrophies linked to $Ca^{2+}$ misregulation.

Example 2

Experimental Procedures

Materials—

The chemiluminescence kit used for immunoblotting was from Applied Biosystems (Foster City, Calif.). Thapsagargin (TG), A23187, and ATP were from Sigma Chemical Co. (St. Louis, Mo.). Dynabeads coupled with sheep anti-mouse IgG or sheep anti-rabbit IgG and Lipofectamine were from Invitrogen (Carlsbad, Calif.). Pi ColorLock ALS reagents were from Novus Biologicals (Littleton, Colo.). Amylose resin was from New England Bioloabs (Ipswich, Mass.). All buffers were supplemented with Complete Protease Inhibitor Cocktail Tables (Roche; Indianapolis, Ind.).

Antibodies—

Primary antibodies against sAnk1 were made by injecting rabbits with the C-terminal sequence of sAnk1 (C-Ahx-VKRASLKRGKQ-OH)[3] linked to BSA. Antibody generation and affinity purification was carried out by 21$^{st}$ Century Biochemicals, Inc. (Marlborough, Mass.). Other primary antibodies used include: SERCA1 (IIH11 mAb), Ryanodine receptor-1 (RyR1) (34C mAb), and triadin (GE 4.90 mAb) from Thermo Scientific (Waltham, Mass.); Junctophilin-1 (JPH1) (ab57425 mAb) from abcam (Cambridge, Mass.); JPH1 (40-5100 rabbit pAb) from Invitrogen; FLAG (M2 mAb and rabbit pAb, Sigma; mCherry (rabbit pAb, Biovision (Milpitas, Calif.)); MBP (E8302 mAb); mouse Ig (MOPC-21, Sigma); rabbit IgG (Jackson ImmunoResearch (West Grove, Pa.)); and SLN (rabbit pAb, Proteintech Group (Chicago, Ill.)).

cDNA Construction—

Rabbit cDNAs encoding SERCA1 and an N-terminal FLAG-tagged sarcolipin (NF-SLN) in the pMT2 vector were gifts from Dr. David MacLennan (University of Toronto). SERCA1 cDNA was extracted by digestion with EcoRI, and inserted into the pCDNA3.1 (−) vector. A C-terminal FLAG-tagged sAnk1 was generated by digesting sAnk1 cDNA from the pmCherry-N1 vector constructed previously (48) with EcoRI and BamHI, and ligating it into p3×FLAG-CMV-14. Sense (5'CCGATCATGGAGCGATC-CACCCGGGAGCTGTGTCTCAACTTCACTGTTGTC-CTTAT TACAGTGATCCTTATTTGGCTCCTTGTGAG-GTCCTACCAGTACTGAG3') (SEQ ID NO. 4) and antisense (5'AATTCTCAGTACTGGTAGGACCTCA-CAAGGAGCCAAATAAGGATCACTGTAATAA GGA-CAACAGTGAAGTTGAGACACAGCTCCCGGGTG-GATCGCTCCATGATCGGAGCT 3') (SEQ ID NO. 5) oligomers of the rabbit SLN coding region were synthesized with SacI (5') and EcoRI (3') overhanging restriction sites (Integrated DNA Technologies, Coralville, Iowa) and hybridized. The hybridized SLN oligomer, as well as cDNAs encoding SERCA1 (5' SacI, 3' EcoRI), sAnk1 (5' KpnI, 3' EcoRI) and dysferlin (5' KpnI, 3' BclI) were all inserted into the pmCerulean3-C1 (CFP) and pmVenus-C1 (YFP) vectors. Construction of the mCerulean3: mVenus conjugate has been described (57, 58).

Transfection—

COS7 cells (American Type Culture Collection, Manassas, Va.) were cultured in DMEM supplemented with 10% fetal bovine serum and 1% penicillin/streptomycin in an atmosphere of 10% $CO_2$/90% air and transiently transfected with cDNA at a concentration of 1 µg/mL and either Lipofectamine 2000 (Invitrogen) or LipoD293 (SignaGen, Gaithersburg, Md.), according to manufacturer's protocols. When two cDNAs were transfected together, a ratio was used of 1:2 (SERCA1 cDNA: X, where X was sAnk1 or SLN cDNA). Cells were seeded to achieve ~70-80% confluency at time of transfection, and incubated for 48 h to allow protein expression. Cells seeded on 35 cm tissue culture plates with glass bottoms (MatTek, Ashland, Mass.) were washed with Hank's balanced salt solution+0.1% bovine serum albumin and used for anisotropy-based fluorescence resonance energy transfer (AFRET). Cells in 10 cm tissue culture dishes were washed twice with PBS, detached with a cell scraper, homogenized and subjected either to differential centrifugation (59) to obtain a microsomal fraction for ATPase measurements, or subjected to centrifugation at 12,000×g and solubilized in a solution containing 0.5% Tween-20 (see below) for co-immunoprecipitation studies.

Co-Immunoprecipitation—

CoIP experiments were performed as described in (60), with preparations of SR vesicles isolated by the method of Eletr and Inesi (61, 62) from rabbit skeletal muscle from the back and hind limb (Pel-Freez, Rogers, Ark.), or from crude membrane extracts of COS7 cells prepared as described (59, 63). For the latter, COS7 cells were harvested in PBS at 48 h following transfection, collected by centrifugation, frozen in liquid $N_2$ and stored at $-80°$ C. until needed. Briefly, pellets were homogenized with 30 strokes of a glass Dounce homogenizer in resuspension buffer (0.25 M sucrose, 10 mM Tris-HCl, pH 7.5, 20 mM $CaCl_2$, 3 mM 2-mercaptoethanol, 150 mM KCl), and solubilized with an equal volume of lysis buffer (40 mM HEPES-NaOH, pH 7.5, 300 mM NaCl, 2 mM EDTA, 1% Tween 20). SR vesicles were prepared for coIP by the same methods for resuspension and solubilization. The muscle and cell extracts were pre-cleared with 50 µL uncoated Dynabeads. The pre-cleared extracts were mixed with antibody-coated Dynabeads (5 ug antibody/50 uL beads) and incubated at 4° C. for 4 h. Following ≥5 washes in washing buffer (20 mM HEPES, pH 7.5, 150 mM NaCl, 1 mM EDTA, 0.5% Tween 20), protein was eluted by boiling the beads in 70 µL SDS-PAGE sample loading buffer. Proteins in the samples were separated by SDS-PAGE and analyzed via immunoblot as described (64).

Microscopy—

Cultures of COS7 cells transfected as described above were fixed in PBS containing 4% paraformaldehyde and 4% sucrose for 15 min at room temperature and mounted in Vectashield (Vector Laboratories, Burlingame, Calif.). Confocal microscopy used a Zeiss 510 META system (Carl Zeiss, Thornwood, N.Y.) equipped with a 63×, 1.4 numerical aperture objective lens. Images were collected by exciting the samples at 458 nm (CFP) and 514 nm (YFP), provided by an argon laser, and collected through 480-520 nm (CFP) and 530-600 nm (YFP) BP filters. Co-localization was assessed by Pearson's coefficients with ImageJ software (http://rsb.info.nih.gov/ij/index.html), and the Just Another Co-localization Plugin (65).

To study the interaction between SERCA1 and sAnk1 by AFRET, transfected COST cells on cover slips were washed with HBSS+0.1% BSA without phenol red and examined with a specially equipped Zeiss AxioObserver microscope (66) with a 20×, 0.75 numerical aperture dry objective lens. Details of the filters used to collect emissions and equations used to analyze the data have been described (66, 67). Briefly, fields were illuminated with vertically polarized light and the intensity of emitted light was measured in planes parallel (V) and perpendicular (H) to that used for illumination. Emissions were collected for donor, acceptor, and FRET (excite donor, collect acceptor) fluorescence in both planes. Image J software was used to stack and align the images (16-bit) and to collect mean intensity values from a minimum of 3 regions of interest (ROI) per cell. ROIs were excluded if their mean pixel intensity value was <2000 above background. Microsoft Excel was used to calculate anisotropies and FRET, indicated by a non-zero difference between the anisotropy measured for the FRET channel compared to the anisotropy measured for the donor ($\Delta r = rCFP - rFRET$). The many advantages of AFRET over other FRET methods have been discussed (57, 68).

Blot Overlay Assay—

The blot overlay assay was performed as described (50, 69) with minor modifications. Aliquots containing 10 µg of SR vesicle protein, purified as described above, were separated on 4-12% SDS-PAGE gels and transferred to PVDF membranes. Blots were placed in overlay buffer (50 mM Tris, pH 7.5, 120 mM NaCl, 3% BSA, 2 mM dithiothreitol, 0.5% NP-40, 0.1% Tween-20) for 4 h at 25° C. and then incubated with 3 µg/mL MBP or sAnk1 (29-155)-MBP in overlay buffer for 12 h at 4° C. The generation and purification of these fusion proteins were as described (51). A separate section of the membrane was reserved to identify SERCA1. Blots were washed extensively with overlay buffer and once with TBS, pH 7.4, plus 0.5% Tween-20 (TBST). The blots were blocked in TBST+4% non-fat dry milk for 4 h at 25° C. and probed with antibodies to MBP (overlay portion) and SERCA1 (non-overlay portion). Immunoblots were completed as described above.

MBP Pull Down Assay—

Maltose Binding Protein (MBP) and sAnk1 (29-155)-MBP fusion protein (20 µg) were bound to 50 µL of amylose resin in MBP column buffer (20 mM Tris-HCl, 200 mM NaCl, 1 mM EDTA). Resin was washed extensively with column buffer and once with IP lysis buffer (see above) and then mixed with 250 µg protein from COS7 cell lysates transfected to express SERCA1 (see above), and incubated for 12 h at 4° C. After the amylose resin was washed extensively in IP buffer, bound proteins were eluted by boiling in 50 µL SDS-PAGE sample loading buffer and analyzed via SDS-PAGE and immunoblotting methods (64).

Assay of $Ca^{2+}$-ATPase Activity—

ATPase activity was measured in microsomes prepared as described (59) from transfected COS7 cells with a colorimetric assay to detect inorganic phosphate ($P_i$) released during ATP hydrolysis. Microsomal vesicles (20 µg/ml) were incubated in assay buffer (20 mM MOPS, pH 7.0, 100 mM KCl, 5 mM $NaN_3$, 5 mM $MgCl_2$, 1 mM EGTA, 2.5 mM ATP, 2 µM ionophore A23187). Reactions were initiated by addition of different amounts of $CaCl_2$ to achieve desired $[Ca^{2+}_{free}]$, as calculated by Maxchelator webware free, (http://maxchelator.stanford.edu/webmaxc/webmaxclite115.html). Following a 30 min incubation at 37° C., reactions were loaded in triplicate onto 96 well plates and terminated by addition of $P_i$ ColorLock ALS reagent to detect $P_i$. Absorbance was read 30 min later at 635 nm on a Tecan Infinite M1000 Pro spectrophotometer. Immunoblots were used to measure levels of SERCA1 in each experimental group. Densitometric analysis with ImageJ quantified the relative expression levels of SERCA1 in the different cell preparations to normalize the measured ATPase activity. Activity values are reported as percentage of the maximum level of activity when SERCA1 was expressed alone.

Transmembrane Modeling and Protein Docking—

The TM region of sAnk1 and SLN were modeled with I-TASSER (70) and the sequences of the human proteins. ClusPro version 2.0 was used for automated protein docking simulation (71-74). The sAnk1 TM model obtained from I-TASSER was docked to the crystal structure of SERCA1 (4H1W). Models were visualized and annotated with Deep-View, the Swiss-PdbViewer version 4.10 (75).

Statistics—

Values are reported as mean±SE. Each data point for AFRET experiments represents the average Δr value from all valid ROIs (see Microscopy for criteria). T-tests compared these values to a theoretical mean of zero to determine if the mean AFRET value was statistically significant. Student's t-tests were used to compare sAnk1 (WT) and (all-L) for coIP and AFRET experiments with p<0.05 being considered significant. Results of assays of ATPase activity were fit to the equation for an allosteric sigmoidal model ($Y=V_{max}*[S]^h/(Kprime+[S]^h)$: (76, 77).) from data acquired in 4 experiments conducted on microsomes from 3 independent transfections. $K_{Ca2+}$ ($[Ca^{2+}]_{free}$ resulting in half-maximal activation) was calculated using nonlinear regression analysis. All graphs were produced with GraphPad Prism 5 software (La Jolla, Calif.). Statistics were evaluated with one-way ANOVA with p<0.05 being considered significant.

Protein Accession Numbers—

The NCBI accession numbers for the proteins studied here are: SERCA1 (Rabbit-NP_001082787), sAnk1 (Human-NP_065211.2; Mouse-NP_001264213; Rat-Not available), SLN (Human-NP_003054; Mouse-NP_079816; Rat-NP_001013265), PLN (Mouse-NP_001135399), MLN (Mouse-NP_001291668).

Example 3

Exemplary Results

The TM Domain of sAnk1 Shares Sequence Similarity with SLN—

The observation that sAnk1 colocalizes with SERCA1 and is required for the structural integrity of the nSR suggested an interaction between sAnk1 and SERCA1. SLN is the major regulator of SERCA1 activity in skeletal muscle, and it is known to associate with SERCA through transmembrane (TM) interactions (22). For these reasons, the TM amino acid sequences of sAnk1 and SLN were compared. As sAnk1 and SLN are oriented in opposite directions within the SR membrane (FIG. 1A), the two sequences were aligned accordingly (FIG. 1B). The TM domains of these proteins were 29% identical and 53% conserved, for an overall similarity of 82% (FIG. 1C). sAnk1 shared considerable sequence similarity with PLN (76%), and to a lesser extent with MLN (47%, FIG. 1D).

To determine the significance of the sequence similarity between sAnk1 and SLN, a database comprised of 13,607 TM sequences was searched for the identical residues shared between sAnk1 and SLN (78). It was determined that 0.75% of sequences in this database contain the sequence TVLL or its reverse, LLVT, suggesting that the sequence similarity is significant. The values of Senes et al. (78) were used for the frequency at which each amino acid occurs at a particular position in TM sequences, to calculate the chances of the 17-FXXXXXTVLL-8 (SEQ ID NO. 6) sequence occurring randomly. This probability was <0.00002. Consistent with these observations, NCBI BLAST alignment of the TM domains of sAnk1 and SLN gave an E-value of 7E-4. These results indicate that the similarity between these sequences is highly significant (79).

Interestingly, two of the residues that sAnk1 shares with SLN, V19 and L21 (V10 and L8 of sAnk1), mediate SLN's ability to reduce the affinity of SERCA1 for $Ca^{2+}$ (20). Therefore it was considered that, like SLN, sAnk1 interacts with SERCA1 and that this interaction occurs at least in part via its TM domain.

Interaction of sAnk1 and SERCA1—

Figure 2A:
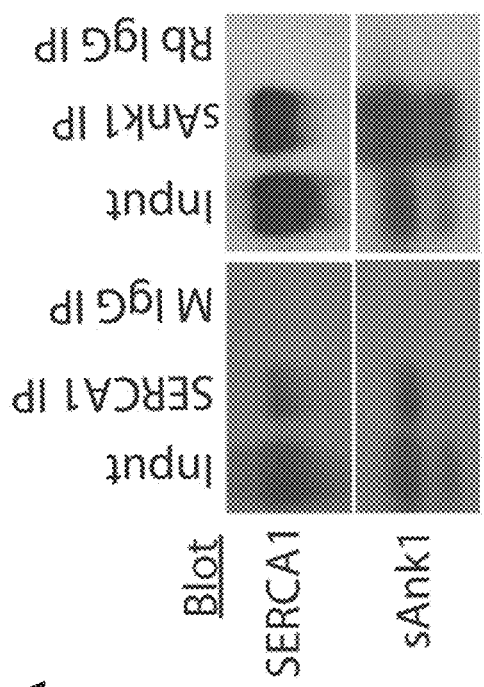

The interaction between SERCA1 and sAnk1 was first analyzed by co-immunoprecipitation (coIP), performed with SR vesicles prepared from rabbit skeletal muscle (see Methods). Immunoblots of the proteins in the precipitate indicated that IP of SERCA1 resulted in specific coIP of sAnk1 (FIG. 2A, left). Similarly, blots of immunoprecipitates (IPs) generated with antibodies specific to sAnk1 showed coIP of SERCA1 (FIG. 2A, right). Ryanodine receptor 1 (RyR1) is the calcium release channel located in the SR membrane of skeletal muscle and is known to interact with several proteins at the triad junction, including the transmembrane proteins triadin and junctophilin-1 (JPH1) (80, 81). To confirm the specific interaction between SERCA1 and sAnk1, antibodies specific for JPH1 were compared to antibodies to sAnk1 in their ability to coIP SERCA from SR vesicles. Again, western blot analysis of the eluates confirmed that SERCA1 coimmunoprecipitated with sAnk1, but that triadin and RyR1 did not. Antibodies to JPH1 resulted in coIP of both RyR1 and triadin, but not SERCA1 or sAnk1 (FIG. 2B). These results indicate that SERCA1 and sAnk1 interact specifically to form a distinct complex within the membranes of isolated SR vesicles.

Interactions between SERCA and other proteins are commonly studied with exogenous expression systems to facilitate manipulation of experimental conditions. One such method involves the preparation of microsomes from transfected eukaryotic cells (63), that is adopted here. COS7 cells were co-transfected with SERCA1-pcDNA3.1 and with either sAnk1-mCherry or empty mCherryN1 vector. A crude microsomal fraction was isolated from the cells ~48 h later, dissolved in detergent solution and subjected to IP with antibodies against SERCA1 or mCherry. Results showed that IP of either SERCA1 or sAnk1-mCherry led to coIP of the other protein, but that coIP did not occur from homogenates containing mCherry and SERCA1 (FIG. 3A). In all cases, the level of specific IP and coIP was several fold greater than that of the non-specific signals observed after IP with non-immune IgG. IP of SERCA1 or a FLAG-tagged sAnk1 variant (sAnk1-FLAG) was also able to coIP the other protein when co-expressed in COS7 cells (FIG. 7A), indicating that the association of these proteins in COS7 cells was not impacted significantly by the epitope tag. These results further support the idea that sAnk1 and SERCA1 interact specifically.

Figure 4:
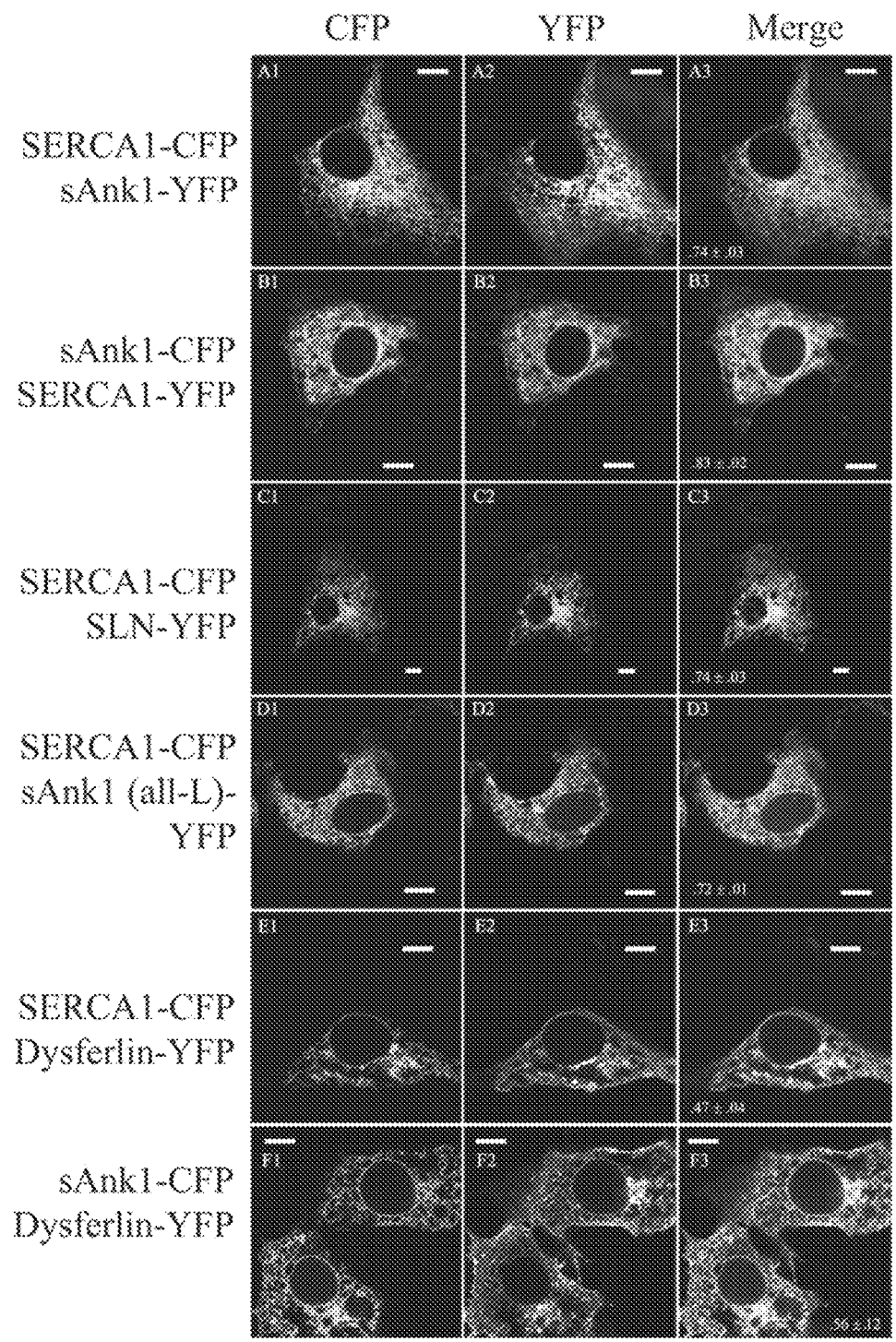
FIG. 4. Colocalization of fluorescent fusion proteins in COS7 cells. COS7 cells were transfected with cDNA encoding the indicated fluorescent fusion proteins. Significant colocalization was observed when SERCA1-CFP was co-expressed with SLN-YFP, sAnk1-YFP and sAnk1 (all-L)-YFP (see merged panels A3, B3 and C3, respectively), as measured by Pearson's correlation coefficient The values of the Pearson's coefficient is included at the bottom of the merged image for each pair of proteins studied (>0.7 for each). Scale bar=10 μm.

The interaction of SERCA and sAnk1 was examined in COS7 cells co-transfected with SERCA1-CFP and sAnk1-YFP. Both proteins distributed in a reticular pattern, typical of localization to the endoplasmic reticulum (ER; FIG. 4), although some may reside in other membrane compartments, including the Golgi complex. Co-transfections with DS-Red-KDEL (the gift of Dr. S. Feng, University of Maryland, Baltimore) confirmed the identity of this membrane compartment as ER.

Analysis with Pearson's correlation coefficient showed significant colocalization of SERCA1-CFP and sAnk1-YFP (0.74±0.03: FIG. 4A). The level of codistribution was comparable when the CFP and YFP moieties were switched (0.83±0.02; FIG. 4B). Colocalization studies of SERCA1-CFP and SLN-YFP (0.74±0.031: FIG. 4C) and SERCA1-CFP and sAnk1 (all-L)-YFP (0.72±0.01: FIG. 4D) gave similar results.

The co-transfected COS7 cells were studied further using an anisotropy-based fluorescence resonance energy transfer (AFRET) assay to determine if SERCA1 and sAnk1 reside within molecular distances (≤10 nm) of each other in living cells. The method is based on the principle that a fluorescently labeled protein excited with polarized light will emit highly polarized photons, leading to large anisotropy values (57, 68). A nearby acceptor fluorescent protein is not fully constrained to the original polarization plane, resulting in reduced anisotropy if FRET occurs between the donor and acceptor. By setting a minimum intensity cutoff required for inclusion of any region of interest (ROI), it was ensured AFRET that was examined only in areas of the cell that co-expressed donor and acceptor.

Figure 5A:
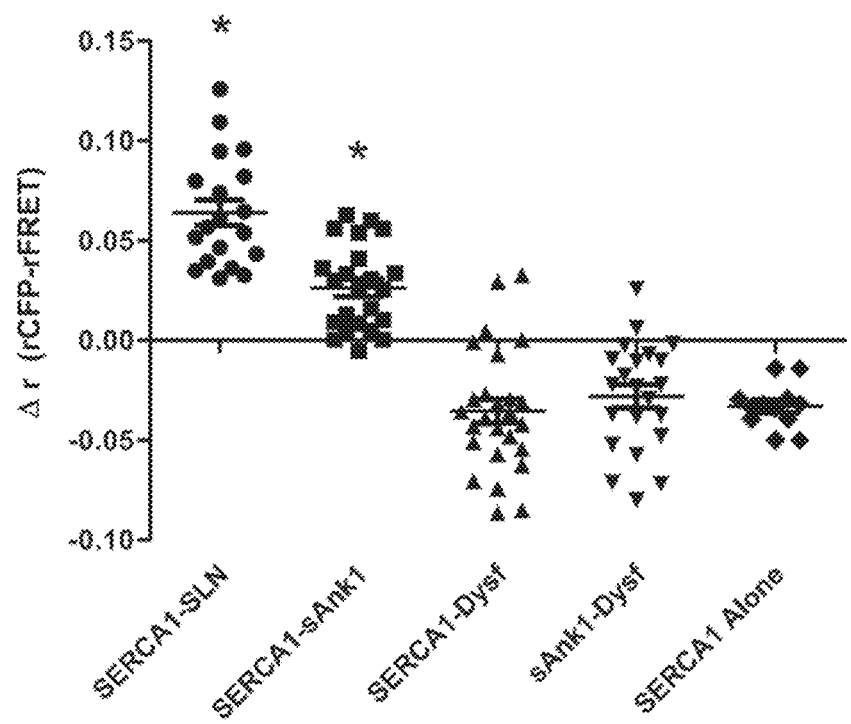
FIGS. 5A-5B. AFRET of sAnk1 and SERCA and SLN and SERCA in COS7 cells. 5A. COS7 cells were transfected with SERCA-CFP together with either sAnk1-YFP, sAnk1 (all-L)-YFP, SLN-YFP, or dysferlin-YFP. SERCA-CFP alone was used as a control. One day post-transfection, AFRET was measured and expressed as Ar (rCFP-rFRET). Each point represents the average AFRET for a single cell. T-tests for each sample set were performed against a theoretical mean of zero; * indicates that the mean is statistically greater than zero (p<0.0001). Results show energy transfer between sAnk1 and SERCA1, and SLN and SERCA1, but not between SERCA1 and dysferlin, sAnk1 and dysferlin, or SERCA1 alone. 5B. When compared to sAnk1 via t-test (WT), sAnk1 (all-L) showed a significant reduction in Ar, suggesting reduced binding due to the mutated TM domain (***, p=0.0008).

The results with COS7 cells transfected with cDNAs encoding SERCA1-CFP and sAnk1-YFP are shown in FIG. 5A. A construct encoding the CFP and YFP proteins tethered to one another was used as an intramolecular control to ensure effective transfection and detection of AFRET ($\Delta r_{mean}$=0.125±0.004). The results indicate that the FRET donor-acceptor pair, SERCA1-CFP and sAnk1-YFP, exhibited energy transfer ($\Delta r_{mean}$=0.026±0.004). This value was significantly different from zero (p<0.0001), but less than that obtained in similar studies of SERCA1-CFP and SLN-YFP ($\Delta r_{mean}$=0.064±0.006; p<0.0001). Dysferlin, a protein of the transverse tubules of skeletal muscle (82), was used as a negative control. In COS7 cells, YFP-tagged dysferlin localizes primarily to the ER with SERCA1 and sAnk1 (Pearson's coefficient=0.47±0.04 and 0.56±0.12, respectively; FIGS. 4E and 4F), with small amounts in the plasma membrane and, perhaps, the Golgi complex. When YFP-dysferlin was used as the acceptor, FRET measured in the intracellular membrane compartment was not observed when SERCA1-CFP or sAnk1-CFP was co-expressed as the donor ($\Delta r_{mean}$–0.035±0.006 and –0.028±0.006, respectively). Additionally, there was no AFRET observed in the absence of acceptor (SERCA alone; $\Delta r_{mean}$=–0.033±0.003). These data indicate that sAnk1 and SERCA1, co-expressed as fluorescent fusion proteins in COS7 cells, reside within molecular distances of one another.

sAnk1 Interacts with SERCA1 Through its Transmembrane Domain—

The TM domains of SLN and PLN play a pivotal role in the ability of each to interact with SERCA (24). Due to the sequence similarity between sAnk1 and SLN, it was considered that sAnk1's TM domain would play a role in its association with SERCA1. To test this, a sAnk1 mutant was constructed that had TM amino acid residues 4-20 mutated to leucine, sAnk1 (all-L). Importantly, sAnk1 (all-L) is expressed and targeted in a manner indistinguishable from WT sAnk1 (FIGS. 3 and 4). Analysis of its colocalization with SERCA1 gave Pearson's coefficients that were identical to wild type (0.72±0.01), indicating that it too concentrates with SERCA1 in the ER. Experiments in COS7 cell extracts showed that antibodies to sAnk1 coimmunoprecipitated only 49±6% of SERCA1 from microsomes with sAnk1 (all-L) compared to WT (FIG. 3B (right) and 3D). Similarly, antibodies to SERCA1 coimmunoprecipitated 49±5% sAnk1 (all-L) compared to WT sAnk1 (FIG. 3B (left) and 3C). These results indicate that the TM domain mediates binding of sAnk1 to SERCA1 in the microsomes of COS7 cells.

Figure 5B:
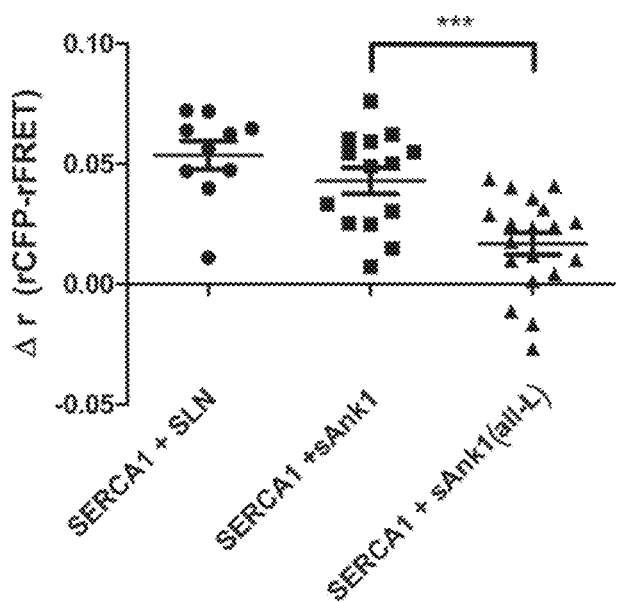

AFRET was utilized to determine if the sAnk1 (all-L) mutant interacts with SERCA1 in living cells. As expected, sAnk1 (all-L) showed a reduced AFRET signal ($\Delta r_{mean}$=0.017±0.005) compared to that of WT sAnk1 ($\Delta r_{mean}$ 0.043±0.005; FIG. 5B p=0.0008). As above, SERCA-CFP and SLN-YFP was used as a positive control ($\Delta r_{mean}$=0.054±0.006). These results support the idea that the TM domain of sAnk1 plays a role in binding to SERCA1 in living cells.

Effect of sAnk1 on SERCA1s $Ca^{2+}$-ATPase Activity—

Figure 6A:
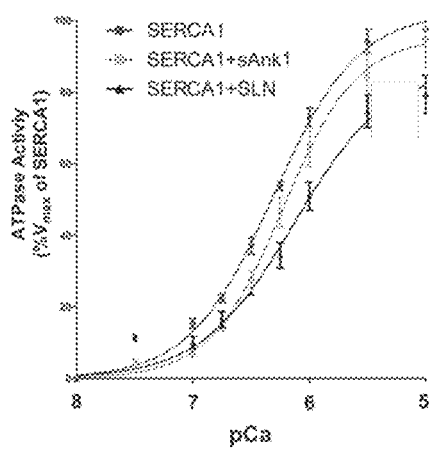
FIGS. 6A-6D. $Ca^{2+}$-ATPase assay in COS7 microsomes. 6A. COS7 cells were transfected with the indicated cDNA construct(s). ATPase activity was determined at each $[Ca^{2+}]_{free}$ compared to the $V_{max}$ measured for SERCA1 alone, following normalization of the levels of SERCA1 expression as determined by immunoblotting (see Experimental Procedures). Data were fitted to the equation for a general cooperative model for substrate binding. Results show that co-expression of sAnk1 with SERCA leads to a reduction of SERCA's apparent affinity for $Ca^{2+}$, but that the effect of sAnk1 is less than that of SLN. 6B. The $K_{ca}$ ($[Ca^{2+}]_{free}$ required for half-maximal activation) values were determined from each curve. Mean $K_{ca}$: SERCA1 pCa=6.33 (468 nM), SERCA1+sAnk1 pCa=6.15 (708 nM), SERCA1+SLN pCa=5.95 (1122 nM). 6C. Unlike sAnk1 (WT), sAnk1 (all-L) did not significantly alter the affinity of SERCA1 for $Ca^{2+}$. 6D. Mean $K_{ca}$: SERCA1 pCa=6.31 (488 nM), SERCA1+sAnk1 pCa=6.10 (794 nM), SERCA1+sAnk1 (all-L) pCa=6.30 (502 nM). Statistics used 1 way ANOVA: *, p<0.05 vs SERCA1, **, p<0.01 vs SERCA1 and #, p<0.05 vs SERCA1+sAnk1 (all-L).
Figure 6B:
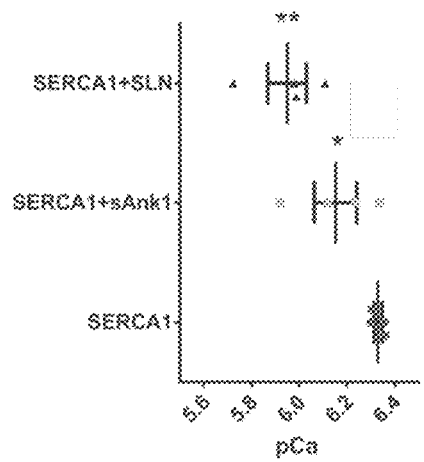

A colorimetric assay was used of Pi release to determine if sAnk1 alters SERCA1's ATPase activity. Microsomes were prepared from COST cells that were transfected to express SERCA1 alone, or SERCA1 in combination with FLAG-SLN or sAnk1-FLAG, and were assayed for $Ca^{2+}$-dependent, thapsigargin-sensitive ATPase activity. The microsomes containing only SERCA1 showed the highest apparent affinity for $Ca^{2+}$, with a $K_{Ca2+}$ ([$Ca^{2+}$]$_{free}$ resulting in half-maximal activation) of 468 nM, equivalent to a $pCa^{2+}$=6.33; Table 1). Expression of a C-terminal FLAG-tagged sAnk1 variant with SERCA1 significantly inhibited SERCA1 by reducing its apparent $Ca^{2+}$ affinity by –0.18 $pCa^{2+}$ units in this experiment (p<0.05; FIGS. 6A and 6B; the value was –0.20 for all studies; Table 1). This was significantly less than the inhibition obtained following co-expression of SERCA1 with SLN carrying an N-terminal FLAG tag (FLAG-SLN), which shifted SERCA1s apparent $Ca^{2+}$ affinity by –0.38 $pCa^{2+}$ units (p<0.05). These results suggest that sAnk1 inhibits SERCA1 by reducing its affinity for $Ca^{2+}$, but that it is a less potent inhibitor than SLN.

Figure 6C:
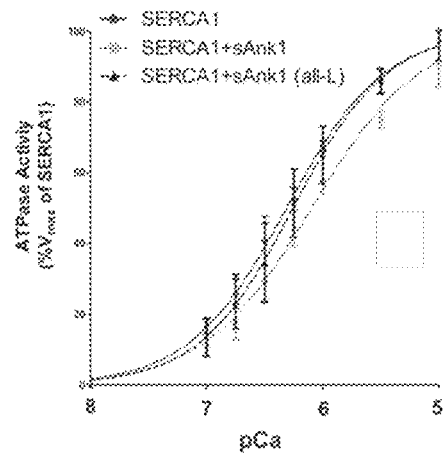
Figure 6D:
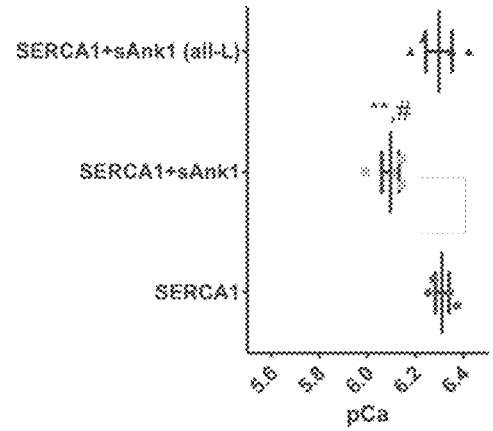

To assess the role of the TM domain in sAnk1's inhibition of SERCA1 activity, ATPase activity was measured in microsomes containing sAnk1 (all-L) and SERCA1. Expression of SERCA1 alone gave a value for $pCa^{2+}$=6.31±0.028. Unlike WT sAnk1, which again significantly reduced SERCA1's apparent $Ca^{2+}$ affinity ($\Delta K_{Ca2+}$=–0.22 $pCa^{2+}$ units), the mutant sAnk1 failed to inhibit SERCA1 activity significantly ($\Delta K_{Ca2+}$=–0.01 $pCa^{2+}$ units; FIGS. 6C and 6D). The compiled results and statistical analysis for all ATPase assays performed for this study are summarized in Table 1. These findings suggest that, like SLN, the contacts made between the TM domain of sAnk1 and SERCA1 are essential to sAnk1's ability to regulate SERCA1 activity.

TABLE 1

ATPase assays.

| | $K_{Ca2+}$ | | | |
| --- | --- | --- | --- | --- |
| | nM [C] | $pCa^{2+}$ | $\Delta K_{Ca2+}$ | n |
| SERCA1 Alone | 479 ± 17 | 6.32 ± .015 | NA | 8 |
| SERCA1 + sAnk1 | 759 ± 83 | 6.12 ± .046*#† | –0.20 | 8 |
| SERCA1 + SLN | 1122 ± 242 | 5.95 ± .081*† | –0.37 | 4 |
| SERCA1 + sAnk1 (all-L) | 501 ± 64 | 6.3 ± .055$ | –0.02 | 4 |

Summary of the compiled results of all ATPase assays presented in FIG. 6. The $K_{Ca2+}$ ([$Ca^{2+}$] required for half-maximal activation) is given in $pCa^{2+}$ units (right column) and nM concentration (left column). The change in $K_{Ca2+}$ ($\Delta K_{Ca2+}$) relative to control (SERCA1 Alone) is given in $pCa^{2+}$ units.
Results are mean values ± SEM.
The following indicate significant difference (p < 0.05) in mean $pCa^{2+}$ as measured by one-way ANOVA:
*compared to SERCA1 Alone;
compared to SERCA1 + SLN; compared to SERCA1 + sAnk1 (all-L).
$Not significantly different from SERCA1 Alone.

sAnk1's Cytoplasmic Domain Interacts with SERCA1 In Vitro—

In addition to TM contacts, SLN and PLN are known to make luminal and cytoplasmic contacts with SERCA1, respectively (36, 83, 84). As sAnk1 also has a long cytoplasmic extension, and as the coIP studies suggested that mutation of the TM domain alone was not sufficient to eliminate sAnk1-SERCA1 association, the possible interaction of sAnk1's cytoplasmic domain with SERCA1 in vitro was investigated.

CoIP studies were performed on extracts of COS7 cells transfected to express SERCA1 and WT sAnk1 or the cytoplasmic domain of sAnk1 (sAnk1$_{29-155}$), each with a FLAG epitope at its C-terminus. Empty FLAG vector was used as a control. Immunoblots of the IP generated with antibodies to SERCA1 probed with anti-FLAG antibodies showed coIP of not only the WT sAnk1, as reported above, but also of sAnk1$_{29-155}$. (FIG. 7A, bottom panel). The intensity of the band in the coIP was less for the cytoplasmic domain than for the full length protein, however, consistent with the role of TM interactions in sAnk1-SERCA1 interactions noted in the experiments above.

The interaction between the cytoplasmic domain of sAnk1 and SERCA1 was further confirmed using a bacterially expressed sAnk1$_{29-155}$ fused to maltose binding protein (MBP). Amylose resin was bound to sAnk1$_{29-155}$-MBP or MBP protein alone and incubated these samples with detergent extracts of COS7 cells transfected to express SERCA1. Pull down of SERCA1 by the resins was assessed by immunoblot analysis. The sAnk1$_{29-155}$-MBP fusion protein pulled down ~9-fold more SERCA1 than the MBP control (FIG. 7B, top panel).

Finally, blot overlay assays were performed to determine if SERCA1 interacts with the cytoplasmic domain of sAnk1 directly. SR vesicle proteins were separated by SDS-PAGE, transferred to PVDF membranes and incubated with sAnk1$_{29-155}$-MBP fusion protein or MBP protein alone. Probing the blots with anti-MBP revealed a band at ~110 kDa only where sAnk1$_{29-155}$-MBP was overlaid. Equivalent lanes were probed with anti-SERCA1 to show this band corresponded with SERCA1 (FIG. 7C, left panel). Equal loading was demonstrated by staining with Ponceau Red, which also showed a distinct band for SERCA1 at ~110 kDa. Taken together with the coIP, $Ca^{2+}$-ATPase assays, and AFRET data (FIG. 5), these results indicate that sAnk1 associates with SERCA1 directly and that both its TM and cytoplasmic domains mediate this association.

Interaction of sAnk1 and SLN—

Co-immunoprecipitation (coIP) was used to study the ability of sANk1 to interact with SLN in SR vesicles prepared from rabbit skeletal muscle tissue. When antibodies against sAnk1 were used to generate the immunoprecipitate, immunoblot analysis revealed coIP of SLN (FIG. 9A). This suggests that sAnk1 and SLN are able to interact to form a complex within the SR membrane. The ability of sAnk1 and SLN to interact in an exogenous expression system was determined. Using extracts from COS7 cells transfected to express the sAnk1-mCherry and FLAG-SLN fusion proteins showed similar results. Immunoblots of the IP generated using anti-FLAG showed sAnk1-mCherry was co-eluted with SLN (FIG. 9B), consistent with their interaction in SR vesicles.

Figure 10A:
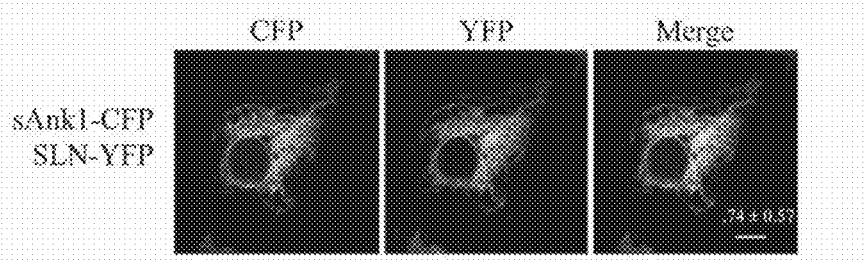
FIGS. 10A and 10B show colocalization of sAnk1 and SLN and sAnk1, SERCA1, and SLN in COS7 cells. 10A. COS7 cells were transfected with cDNAs encoding sAnk1-CFP and SLN-YFP. Significant colocalization was observed as measured by Pearson's correlation coefficient (see bottom right of merged panel). 10B. Additionally, cotransfection of the indicated fluorescent fusion-proteins along with a DS-Red-KDEL marker revealed colocalization of these proteins to the ER. Similar results were observed when SERCA1-CFP, sAnk1-YFP, and SLN-mCherry were coexpressed.
Figure 10B:
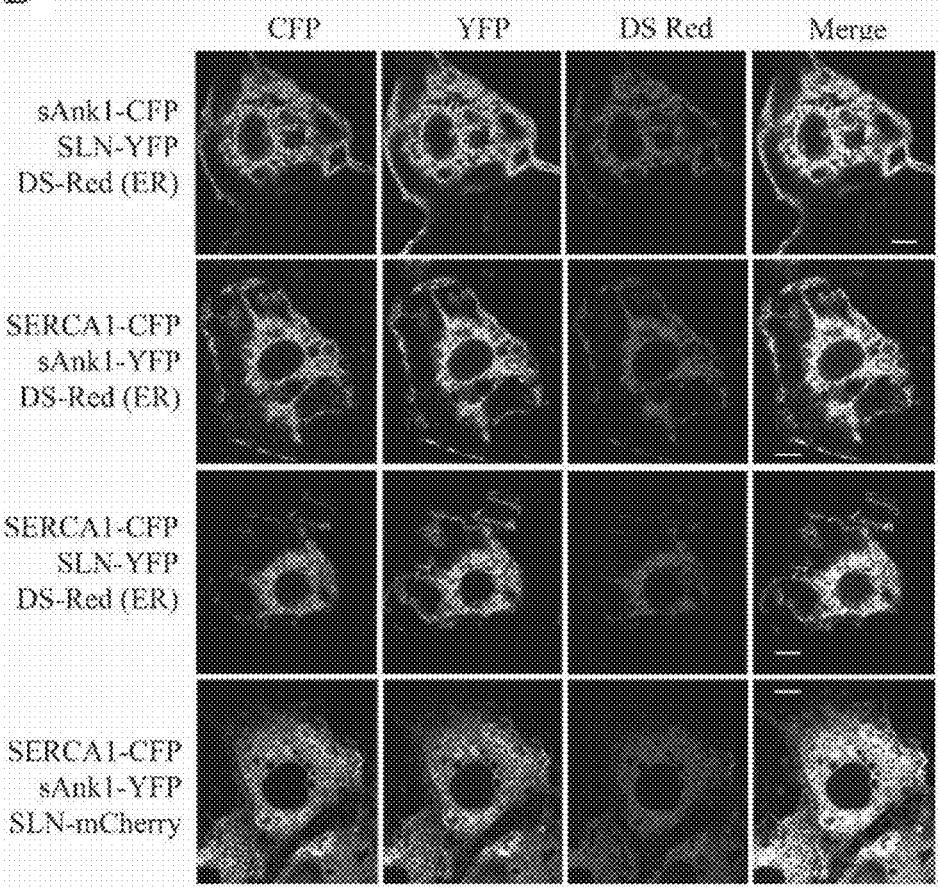

As a second method to investigate the interaction between sAnk1 and SLN, an anisotropy-based fluorescence resonance energy transfer (AFRET) assay was used to demonstrate interaction between sAnk1 and SERCA1. Confocal microscopy was used to assess expression and localization of the fluorescent fusion proteins used for the AFRET studies. COS7 cells transfected to co-express sAnk1-CFP and SLN-YFP showed significant co-localization of the two fluorescent proteins to the endoplasmic reticulum (ER). Analysis with Pearson's correlation coefficient showed a similar level of co-localization between sAnk1 and SLN, as was found with SERCA1 and sAnk1 or SLN (FIG. 10A; 0.74±0.057). ER localization was confirmed via co-transfection with the ER marker, DS-Red-KDEL (FIG. 10B).

AFRET analysis was performed to determine if sAnk1 and SLN reside within 10 nm or less of one another. This method takes advantage of the intrinsically high anisotropy of fluorescent proteins (in contrast to small fluorescent molecules). A donor fluorophore excited with polarized light will have polarized emissions and high anisotropy values. Nearby acceptor molecules may accept photons outside the original plane of polarization via energy transfer, leading to a reduction in the measured anisotropy. This method also reduces the likelihood of false positives caused by overlapping spectra, and eliminates the need for other methods of FRET confirmation such as donor dequenching after acceptor photobleach.

Figure 11:
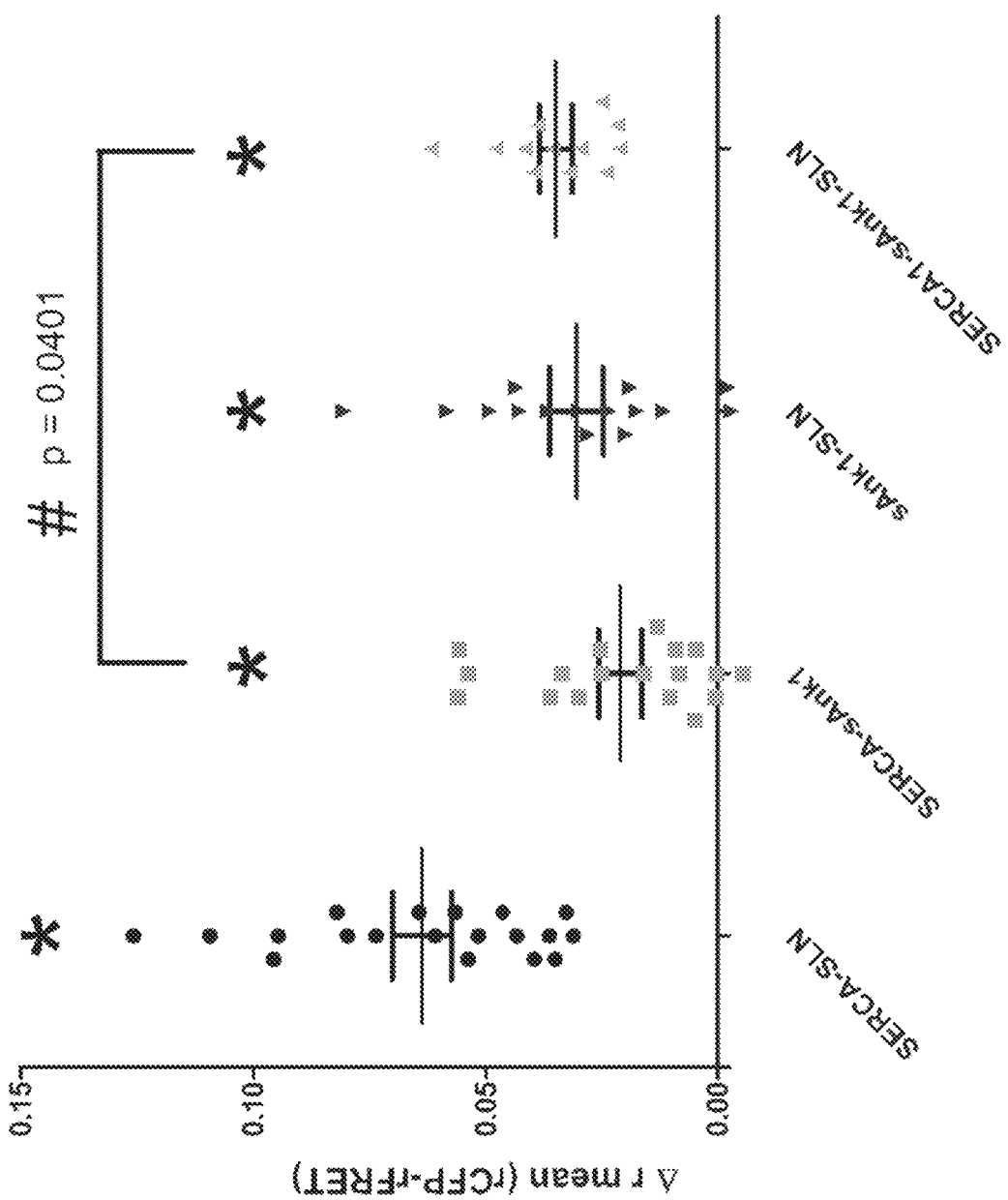
FIG. 11 demonstrates AFRET of sAnk1 and SLN in COS7 cells. COS7 cells were transfected with the donor-acceptor pairs (e.g. SERCA-CFP/SLN-YFP) indicated below the panel. One day post-transfection, AFRET was measured and expressed as Ar (rCFP-rFRET). Each point represents the average AFRET for a single cell. T-tests for each sample set were performed against a theoretical mean of zero; * indicates that the mean is statistically greater than zero ($p<0.0001$). The combinations of sAnk1 and SERCA1 and SLN and SERCA1 were used as a positive control. AFRET was observed between sAnk1-CFP and SLN-YFP. When FLAG-SLN was cotransfected with SERCA-CFP and sAnk1-YFP the average AFRET value was significantly increased as measured by T-test statistically analysis (#, p=0.0401).

Results for the AFRET experiments in COS7 cells are shown in FIG. 11. Energy transfer occurred in cells co-expressing sAnk1-CFP and SLN-YFP ($\Delta r_{mean}$=0.03±0.006). This value was determined to be statistically significant when tested against a theoretical mean of zero (p=0.0001). The AFRET value measured for sAnk1-CFP and SLN-YFP was in a range similar to that observed between SERCA-CFP and SLN-YFP 0.068±0.007), and SERCA-CFP and sAnk1-YFP ($\Delta r_{mean}$=0.021±0.005). In contrast, dysferlin, a protein of the transverse tubules in skeletal muscle, failed to show energy transfer with sAnk1 when it served as the acceptor fluorophore). The observed FRET between sAnk1 and SLN indicate these two proteins reside within the molecular distances of one another required for direct interaction.

SLN Promotes Interaction of sAnk1 and SERCA1—

Figure 13:
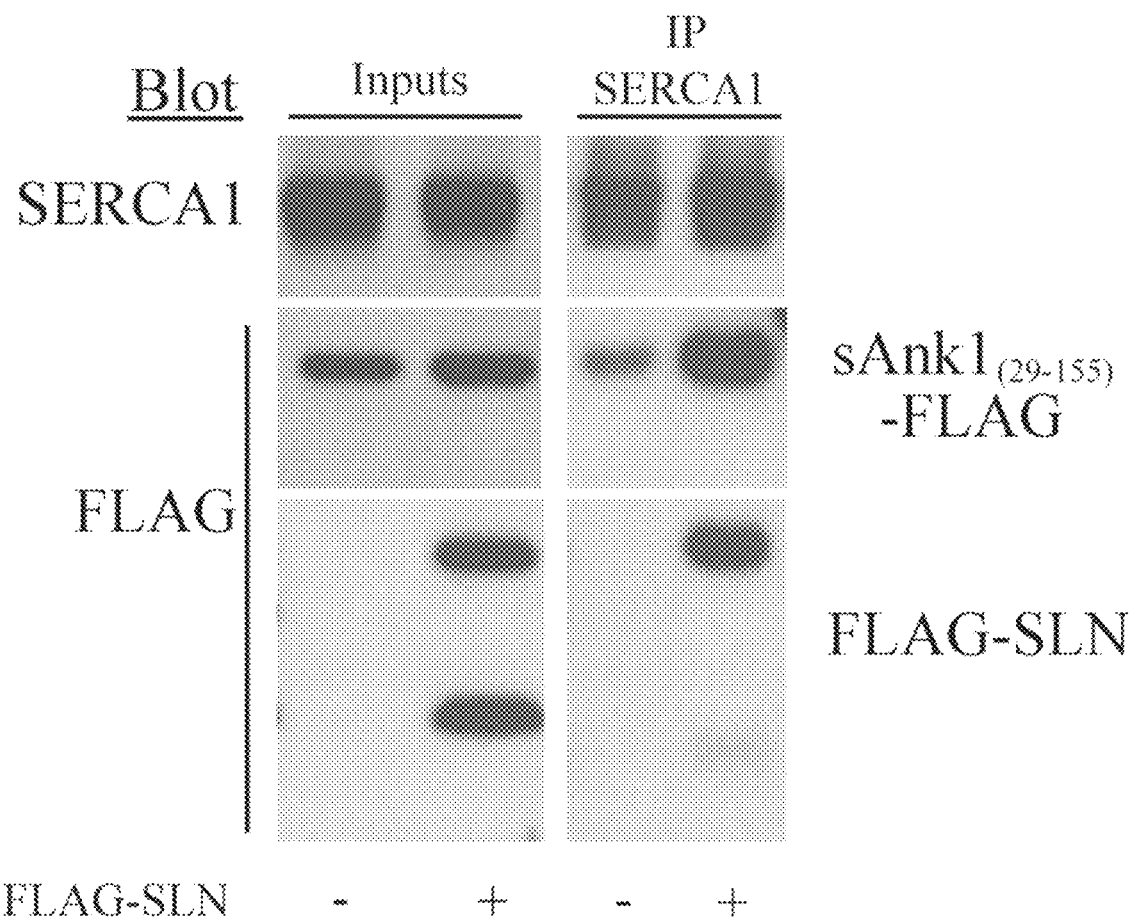
FIG. 13 shows that SLN promotes interaction between sAnk1's cytoplasmic domain ($sAnk_{29-155}$) and SERCA1. Extracts of COS7 cells transfected with SERCA1 and sAnk1 (29-155)-FLAG in the presence or absence of FLAG-SLN (NF-SLN) were subjected to IP with antibodies against SERCA1. Non-immune mouse IgG was used as a control. The results show that the interaction between SERCA1 and the cytoplasmic domain of sAnk1 is increased in the presence of SLN.

The results presented above raised the question of how sAnk1 and SLN may alter the other's ability to interact with SERCA1. To address this coIP experiments were first performed in COS7 cells transfected with SERCA1 and sAnk1-FLAG or FLAG-SLN, or with all three vectors. Interestingly, when compared to co-transfection of SERCA1 and sAnk1, the addition of FLAG-SLN led to a dramatic increase in the coIP of sAnk1 with SERCA1 (FIG. 12A). Upon quantitation, this increase was statistically significant (2.6-fold; p=0.0047; FIG. 12B). It is important to note that two bands (~5 kDa and ~10 kDa) are observed when immunoblotting for FLAG-SLN. This is likely due to SLN's ability to form stable homodimers that persist even following boiling in the solutions containing SDS preparatory to SDS-PAGE (19). Further experiments demonstrated that, increasing the expression of FLAG-SLN by introducing more FLAG-SLN plasmid during the transfection step promoted coIP of sAnk1-FLAG with SERCA1 (FIGS. 12C and 12E). The increase in coIP was linear with the amount of FLAG-SLN cDNA and was statistically significant, as determined via linear regression analysis (slope (m)=0.67; p=0.0018). The reciprocal experiment was next performed, in which sAnk1-FLAG was titrated while SERCA1 and FLAG-SLN were kept constant. Unexpectedly, there was no effect on increasing the amounts of plasmid encoding sAnk1-FLAG on coIP of FLAG-SLN with SERCA1 (FIG. 12D). Linear regression analysis confirmed that sAnk1-FLAG did not alter coIP between SERCA1 and FLAG-SLN (m=0.04, both bands; p=0.046 upper band and 0.045 lower band; FIG. 12F).

sAnk1 interacts with SERCA1 through both TM and cytoplasmic interactions as shown elsewhere herein. Here, the same cytoplasmic region of sAnk1 was used to determine if SLN had any effect on the cytoplasmic interaction between sAnk1 and SERCA1. Similar to its effect on the interaction between SERCA1 and full length sAnk1, the presence of FLAG-SLN enhanced the interaction between sAnk1 (29-155) and SERCA1 2.7-fold (FIG. 13).

AFRET was used to determine if FLAG-SLN enhanced the interaction between sAnk1 and SERCA1. Compared to the AFRET signal from COS7 cells transfected with SERCA-CFP and sAnk1-YFP, the signal from cells cotransfected with FLAG-SLN had an increased $\Delta r_{mean}$ (0.021±0.005 vs. 0.036±0.003; p=0.04; FIG. 11). Thus, SLN promotes interaction between sAnk1 and SERCA1.

sAnk1 Reduces SLN Mediated SERCA1 Inhibition—

The effects on SERCA1's Ca-ATPase activity of sAnk1 and SLN expressed together, compared to either one alone, were examined. The assays use microsomes prepared from COS7 or HEK293 cells and a colorimetric method to measure $P_i$ release. Cells transfected with SERCA1 alone served as a control, and showed the highest level of $Ca^{2+}$-dependent ATPase activity in both COS7 and HEK293 cells (pCa=6.33±0.016 and 6.38±0.025, respectively). As reported previously, sAnk1-FLAG reduced SERCA1's apparent $Ca^{2+}$ affinity, measured in pCa units, in COS7 and HEK293 cells ($\Delta K_{Ca2+}$=-0.18 and -0.21, $pCa^{2+}$ units respectively; FIG. 14). This shift was less than that produced by coexpression of FLAG-SLN ($\Delta K_{Ca2+}$=-0.38 $pCa^{2+}$ units in COS7 and -0.30 in HEK293; FIG. 14). When sAnk1-FLAG and FLAG-SLN were coexpressed with SERCA1, the level of inhibition was less than that exhibited by FLAG-SLN alone ($\Delta K_{Ca2+}$=-0.21 in COS7 and -0.12 $pCa^{2+}$ units in HEK293; FIG. 14), and was statistically identical to that seen with sAnk1 and SERCA1. These findings indicate that sAnk1 reduces SLN-mediated SERCA1 inhibition and may ablate it completely, in certain embodiments.

Significance of Certain Embodiments of the Disclosure

Regulation of SERCA activity in both skeletal and cardiac muscle has been extensively investigated for over 20 years. The majority of these efforts have focused on the homologous proteins, PLN and SLN. These small TM proteins of the SR are differentially expressed in different muscle fibers while exhibiting a similar, though distinct, ability to modulate SERCA activity, mediated in part by the binding of their TM domains to SERCA (14, 17, 20, 84, 85). Binding is thought to occur within a pocket made up of SERCA's TM helices M2, M4, M6 and M9 (26, 30), and leads to a reduction in SERCA's apparent $Ca^{2+}$ affinity (39). The research has focused on sAnk1, a small protein encoded by the ANK1 gene that concentrates with SERCA in the nSR of skeletal muscle. Previous studies established that reduced expression of sAnk1 is accompanied by disruption of the nSR and the loss of SERCA protein. Here, it is shown that the TM domain of sAnk1 shares significant sequence similarity with SLN and mediates binding to SERCA and regulation of its enzymatic activity. It is also shown that, as in PLN-SERCA interactions (36, 84), the cytoplasmic domain of sAnk1 contributes to the binding of sAnk1 to SERCA, and that this binding is direct. The results indicate that sAnk1 is a novel regulator of SERCA1 activity.

sAnk1 was first identified as a small membrane-bound protein which co-purified with SERCA1 from enriched SR fractions of rabbit skeletal muscle (43). It localizes to the SR surrounding M-bands and Z-disks, where its C-terminal, cytoplasmic domain is able to interact with obscurin (present at M-bands and Z-disks; (50, 51)) and titin (present at Z-disks; (47)). Studies with mice lacking obscurin (55) or sAnk1 (56), as well as with mutant forms of sAnk1 expressed in skeletal myofibers are consistent with the idea that sAnk1's binding to obscurin links the SR membrane to the underlying contractile apparatus. Perhaps more significantly, however, sAnk1 is crucial in maintaining integrity of the nSR. Using RNAi technology to reduce the expression of sAnk1, in flexor digitorum brevis (FDB) myofibers, it was found that sAnk1 knockdown disrupts the nSR and also reduces the amount of SERCA protein (49). These changes reduced SR $Ca^{2+}$ load and the rate of $Ca^{2+}$ clearance from the cytosol following a 4-CmC-induced $Ca^{2+}$ transient. Furthermore, quantitative analysis of colocalization revealed that the remaining sAnk1 following knock down was only ~25% localized with SERCA1 compared to ~50% in controls.

These observations raised the question of how sAnk1 influences the stability of the nSR and organization of proteins in the nSR membrane. Comparisons showed that the TM sequence of sAnk1 is very similar to the TM region of SLN. The total sequence similarity shared between both rodents and humans is >80%, with 29% and 24% sequence identity, respectively. The analyses reveal that these similarities are highly significant. As SLN interacts with SERCA via its TM domain (22), it was predicted that sAnk1 would do so, too. Co-immunoprecipitation experiments showed that sAnk1 and SERCA1 associated specifically in SR vesicles isolated from rabbit muscle and in membrane fractions from transfected COS7 cells. Similarly, AFRET experiments in COS7 cells co-expressing pairs of CFP and YFP fusion proteins showed energy transfer from SERCA1-CFP to sAnk1-YFP. This suggests that these proteins reside within 10 nm of one another in living cells (86) and are likely to interact directly. Furthermore, $Ca^{2+}$-ATPase assays showed that co-expression of sAnk1-FLAG and SERCA1 significantly reduced SERCA1's apparent $Ca^{2+}$ affinity. Together, these data support the consideration that sAnk1 is able to interact with SERCA1 to regulate its activity similar to SLN. Moreover, the experiments showing that the cytoplasmic domain of sAnk1 binds to SERCA1 in blot overlay experiments, indicate that the association of sAnk1 with SERCA1 is direct and not mediated by other proteins.

A combination of coIP, AFRET and ATPase assays were employed to elucidate the role of sAnk1's TM domain in its ability to bind to SERCA1 and inhibit its activity. The TM domain of sAnk1 is important in mediating its interaction with SERCA1. sAnk1 (all-L) and SERCA1 were found to coIP together only ~50% as efficiently as WT sAnk1 and SERCA1. Similarly, AFRET analysis revealed a decrease in the $\Delta r_{mean}$ between SERCA1-CFP and sAnk1 (all-L)-YFP compared to WT. The reduced interaction between SERCA1 and sAnk1 (all-L) suggests that sAnk1 may dock to SERCA1 in the same pocket, comprised of several of SERCA1's TM helices, used by SLN and PLN. In specific embodiments, the binding that persists between SERCA1 and sAnk1 (all-L) is due to sAnk1's cytoplasmic domain. The most interesting effect of mutating sAnk1's TM domain was the inability of the mutant to shift SERCA's apparent $Ca^{2+}$ affinity. This observation indicates that specific amino acids within the TM region of WT sAnk1 are important for its inhibitory function, in specific embodiments.

Recently, structural modeling was used to analyze the similarities between the alpha-helical TM region of SLN and myoregulin (MLN), another small protein of the SR membrane that can inhibit SERCA (41). The same software was used to compare the TM regions of sAnk1 and SLN and found that several of the conserved TM residues of sAnk1 shared similar spatial orientations with several identical and conserved residues of SLN (FIG. 8A). In agreement with the considerations and the experimental observations, automated docking simulations predicted that the TM region of sAnk1 binds the same region of SERCA as SLN (FIG. 8B). Closer examination of the predicted docking site of sAnk1 shows amino acid sidechains protruding into the binding pocket where SLN binds SERCA1 (22). When compared to a published crystal structure of the SERCA1-SLN complex, it is clear that several of these residues are shared between sAnk1 and SLN (FIG. 8C). These models are consistent with sAnk1 binding to SERCA1 in the same pocket as SLN, PLN and MLN to modulate SERCA activity.

The changes in binding and the ability of sAnk1 to inhibit SERCA1 activity when the TM domain is mutated to all leucines is particularly interesting considering the similarity between sAnk1 WT and sAnk1 (all-L). WT sAnk1's TM domain contains 6 leucine residues, and 8 of the 11 remaining TM residues are hydrophobic. Therefore only 3 of the TM amino acid residues between positions 4 and 20 represent non-conservative mutations. The 3 hydrophilic residues within the TM domain are Thr6, Glu7 and Thr11. In specific embodiments, these residues may contribute to sAnk1's ability to inhibit SERCA1 activity, but in other embodiments several specific hydrophobic residues may also play a role in modulating SERCA activity, as with SLN and PLN (20, 24, 60, 87, 88), including V10 and L8 residues, which are conserved between sAnk1 and SLN. One can determine the specific TM residues necessary for sAnk1 to exhibit its inhibitory effect.

In addition to TM contacts, cytoplasmic and lumenal interactions are significant for PLN and SLN to regulate SERCA, respectively (36). It was shown recently that mutation or deletion of the C-terminal residues of PLN led to improper localization and impaired regulatory activity (83). Similarly, the highly conserved C-terminus of SLN is important for SLN function. Gorski et al. showed that the lumenal tail of SLN (RSYQY) was required for SLN to inhibit SERCA1 activity maximally, and that a truncated SLN mutant lacking the 4 C-terminal amino acid residues inhibited SERCA1 activity less effectively than full-length SLN (37, 38). These data are in agreement with earlier mutagenic studies that identified Y29, Q30, and Y31 as residues important for SLN's inhibitory effect (20). The significance of SLN's lumenal tail was further indicated with a chimeric PLN mutant which had these residues from SLN added to its C-terminus. This chimeric protein was super-inhibitory, and may help to explain the differences observed in the relative abilities of sAnk1 and SLN to inhibit SERCA1 activity (37). Future studies using chimeric variants of sAnk1 can address this possibility.

As a significant portion of the sAnk1 polypeptide extends into the cytosol (45), it was considered if like PLN and SLN, sAnk1 could interact with SERCA1 independently of the TM domain. This was addressed using the cytoplasmic domain of sAnk1 (residues 29-155) in coIP, pull down, and blot overlay assays. The results show that the cytoplasmic domain of sAnk1 is also able to interact with SERCA1, although less efficiently than full length sAnk1. This would be consistent with a model in which sAnk1-SERCA1 interactions are mediated by a combination of interactions occurring in the TM and cytoplasmic domains of both proteins. More extensive structural analyses and mutagenesis studies are under way to test this idea.

Although sAnk1 interacts directly with SERCA1, it is not clear how, or even if, this interaction helps to stabilize or regulate the function of the nSR in muscle. Short term incubation of myofibers with siRNA to reduce sAnk1 expression and elimination of sAnk1 completely by homologous recombination both lead to loss of the nSR and associated reductions in the rate of $Ca^{2+}$ clearance from the myoplasm (49, 56), Decreased levels of sAnk1 should increase SERCA1 activity, leading to increased rates of $Ca^{2+}$ clearance, but the effects of any such increase may be overridden by the loss of the nSR itself. They may also be altered by changes in other proteins, such as SLN, that regulate SERCA activity but that may also interact with sAnk1 and the sAnk1-SERCA1 complex. These interactions may influence the stability of the nSR membrane either directly, through altered membrane curvature or changes in protein-protein or protein-lipid binding, or indirectly, through changes in the handling of $Ca^{2+}$. Alternatively, the ability of sAnk1 to bind to cytoskeletal proteins, including obscurin (44, 48, 50, see also 52), may influence the stability of the nSR. It will be of considerable interest to learn whether or not sAnk1's cytoplasmic domain can bind obscurin and SERCA1 simultaneously.

Alterations in expression and activity of SERCA in skeletal and cardiac muscle are linked to several forms of muscular dystrophy and cardiomyopathies, including heart failure (5, 7-10). In addition, age-related alterations in SERCA levels have been observed in both animal models and senescent human myocardium, suggesting that it may be relevant to the aging process (6). SERCA activity has also been shown to play a critical role in the pathogenesis of Alzheimer's disease, exemplifying the broad implications of understanding SERCA regulation (89-91) and the significance of discovering potential targets for manipulating SERCA activity.

Herein, it is demonstrated that sAnk1 is able to interact with SERCA1 in skeletal muscle in a way much like SLN. Furthermore, this interaction results in SERCA1 inhibition, as measured by a reduction in SERCA1's apparent $Ca^{2+}$ affinity. The possibility that the expression of sAnk1 is not limited to striated muscle suggests that it may play a more universal role as a regulator of SERCA activity in other tissues. Co-expression of sAnk1 with either SLN, PLN, or MLN in various tissues also suggests a more intricate level of co-regulation by multiple micropeptides and small proteins. One can determine if sAnk1 can interact with SLN and super-inhibit SERCA activity.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

1. Ziman, A. P., Ward, C. W., Rodney, G. G., Lederer, W. J., and Bloch, R. J. (2010) Quantitative measurement of Ca(2)(+) in the sarcoplasmic reticulum lumen of mammalian skeletal muscle. Biophys. J. 99, 2705-2714
2. Launikonis, B. S., Zhou, J., Royer, L., Shannon, T. R., Brum, G., and Rios, E. (2005) Confocal imaging of [Ca2+] in cellular organelles by SEER, shifted excitation and emission ratioing of fluorescence. J. Physiol. 567, 523-543
3. Kabbara, A. A., and Allen, D. G. (1999) Measurement of sarcoplasmic reticulum Ca2+ content in intact amphibian skeletal muscle fibres with 4-chloro-m-cresol. Cell Calcium. 25, 227-235
4. Somlyo, A. V., Gonzalez-Serratos, H. G., Shuman, H., McClellan, G., and Somlyo, A. P. (1981) Calcium release and ionic changes in the sarcoplasmic reticulum of tetanized muscle: an electron-probe study. *J. Cell Biol.* 90, 577-594

5. Brini, M., and Carafoli, E. (2009) Calcium pumps in health and disease. *Physiol. Rev.* 89, 1341-1378
6. Periasamy, M., and Kalyanasundaram, A. (2007) SERCA pump isoforms: their role in calcium transport and disease. *Muscle Nerve.* 35, 430-442
7. Adachi, T. (2010) Modulation of vascular sarco/endoplasmic reticulum calcium ATPase in cardiovascular pathophysiology. *Adv. Pharmacol.* 59, 165-195
8. Diaz, M. E., Graham, H. K., O'neill, S. C., Trafford, A. W., and Eisner, D. A. (2005) The control of sarcoplasmic reticulum Ca content in cardiac muscle. *Cell Calcium.* 38, 391-396
9. Schmidt, A. G., Zhai, J., Carr, A. N., Gerst, M. J., Lorenz, J. N., Pollesello, P., Annila, A., Hoit, B. D., and Kranias, E. G. (2002) Structural and functional implications of the phospholamban hinge domain: impaired SR Ca2+ uptake as a primary cause of heart failure. *Cardiovasc. Res.* 56, 248-259
10. Vangheluwe, P., Tjwa, M., Van Den Bergh, A., Louch, W. E., Beullens, M., Dode, L., Carmeliet, P., Kranias, E., Herijgers, P., Sipido, K. R., Raeymaekers, L., and Wuytack, F. (2006) A SERCA2 pump with an increased Ca2+ affinity can lead to severe cardiac hypertrophy, stress intolerance and reduced life span. *J. Mol. Cell. Cardiol.* 41, 308-317
11. Koss, K. L., Ponniah, S., Jones, W. K., Grupp, I. L., and Kranias, E. G. (1995) Differential phospholamban gene expression in murine cardiac compartments. Molecular and physiological analyses. *Circ. Res.* 77, 342-353
12. Tada, M., and Toyofuku, T. (1998) Molecular regulation of phospholamban function and expression. *Trends Cardiovasc. Med.* 8, 330-340
13. Briggs, F. N., Lee, K. F., Wechsler, A. W., and Jones, L. R. (1992) Phospholamban expressed in slow-twitch and chronically stimulated fast-twitch muscles minimally affects calcium affinity of sarcoplasmic reticulum Ca(2+)-ATPase. *J. Biol. Chem.* 267, 26056-26061
14. Odermatt, A., Taschner, P. E., Scherer, S. W., Beatty, B., Khanna, V. K., Cornblath, D. R., Chaudhry, V., Yee, W. C., Schrank, B., Karpati, G., Breuning, M. H., Knoers, N., and MacLennan, D. H. (1997) Characterization of the gene encoding human sarcolipin (SLN), a proteolipid associated with SERCA1: absence of structural mutations in five patients with Brody disease. *Genomics.* 45, 541-553
15. Vangheluwe, P., Schuermans, M., Zador, E., Waelkens, E., Raeymaekers, L., and Wuytack, F. (2005) Sarcolipin and phospholamban mRNA and protein expression in cardiac and skeletal muscle of different species. *Biochem. J.* 389, 151-159
16. Babu, G. J., Zheng, Z., Natarajan, P., Wheeler, D., Janssen, P. M., and Periasamy, M. (2005) Overexpression of sarcolipin decreases myocyte contractility and calcium transient *Cardiovasc. Res.* 65, 177-186
17. Gayan-Ramirez, G., Vanzeir, L., Wuytack, F., and Decramer, M. (2000) Corticosteroids decrease mRNA levels of SERCA pumps, whereas they increase sarcolipin mRNA in the rat diaphragm. *J. Physiol.* 524 Pt 2, 387-397
18. Stammers, A. N., Susser, S. E., Hamm, N. C., Hlynsky, M. W., Kimber, D. E., Kehler, D. S., and Duhamel, T. A. (2015) The regulation of sarco(endo)plasmic reticulum calcium-ATPases (SERCA). *Can. J. Physiol. Pharmacol.* 1-12
19. Hellstern, S., Pegoraro, S., Karim, C. B., Lustig, A., Thomas, D. D., Moroder, L., and Engel, J. (2001) Sarcolipin, the shorter homologue of phospholamban, forms oligomeric structures in detergent micelles and in liposomes. *J. Biol. Chem.* 276, 30845-30852
20. Odermatt, A., Becker, S., Khanna, V. K., Kurzydlowski, K., Leisner, E., Pette, D., and MacLennan, D. H. (1998) Sarcolipin regulates the activity of SERCA1, the fast-twitch skeletal muscle sarcoplasmic reticulum Ca2+-ATPase. *J. Biol. Chem.* 273, 12360-12369
21. Afara, M. R., Trieber, C. A., Glaves, J. P., and Young, H. S. (2006) Rational design of peptide inhibitors of the sarcoplasmic reticulum calcium pump. *Biochemistry.* 45, 8617-8627
22. Asahi, M., Sugita, Y., Kurzydlowski, K., De Leon, S., Tada, M., Toyoshima, C., and MacLennan, D. H. (2003) Sarcolipin regulates sarco(endo)plasmic reticulum Ca2+-ATPase (SERCA) by binding to transmembrane helices alone or in association with phospholamban. *Proc. Natl. Acad. Sci. U.S.A.* 100, 5040-5045
23. Hutter, M. C., Krebs, J., Meiler, J., Griesinger, C., Carafoli, E., and Helms, V. (2002) A structural model of the complex formed by phospholamban and the calcium pump of sarcoplasmic reticulum obtained by molecular mechanics. *Chembiochem.* 3, 1200-1208
24. Morita, T., Hussain, D., Asahi, M., Tsuda, T., Kurzydlowski, K., Toyoshima, C., and Maclennan, D. H. (2008) Interaction sites among phospholamban, sarcolipin, and the sarco(endo)plasmic reticulum Ca(2+)-ATPase. *Biochem. Biophys. Res. Commun.* 369, 188-194
25. Seidel, K., Andronesi, O. C., Krebs, J., Griesinger, C., Young, H. S., Becker, S., and Baldus, M. (2008) Structural characterization of Ca(2+)-ATPase-bound phospholamban in lipid bilayers by solid-state nuclear magnetic resonance (NMR) spectroscopy. *Biochemistry.* 47, 4369-4376
26. Toyoshima, C., Asahi, M., Sugita, Y., Khanna, R., Tsuda, T., and MacLennan, D. H. (2003) Modeling of the inhibitory interaction of phospholamban with the Ca2+ATPase. *Proc. Natl. Acad. Sci. U.S.A.* 100, 467-472
27. Traaseth, N. J., Ha, K. N., Verardi, R., Shi, L., Buffy, J. J., Masterson, L. R., and Veglia, G. (2008) Structural and dynamic basis of phospholamban and sarcolipin inhibition of Ca(2+)-ATPase. *Biochemistry.* 47, 3-13
28. Asahi, M., Kurzydlowski, K., Tada, M., and MacLennan, D. H. (2002) Sarcolipin inhibits polymerization of phospholamban to induce superinhibition of sarco(endo)plasmic reticulum Ca2+-ATPases (SERCAs). *J. Biol. Chem.* 277, 26725-26728
29. Autry, J. M., Rubin, J. E., Pietrini, S. D., Winters, D. L., Robia, S. L., and Thomas, D. D. (2011) Oligomeric interactions of sarcolipin and the Ca-ATPase. *J. Biol. Chem.* 286, 31697-31706
30. Buffy, J. J., Buck-Koehntop, B. A., Porcelli, F., Traaseth, N. J., Thomas, D. D., and Veglia, G. (2006) Defining the intramembrane binding mechanism of sarcolipin to calcium ATPase using solution NMR spectroscopy. *J. Mol. Biol.* 358, 420-429
31. Harrer, J. M., and Kranias, E. G. (1994) Characterization of the molecular form of cardiac phospholamban. *Mol. Cell. Biochem.* 140, 185-193
32. Li, M., Reddy, L. G., Bennett, R., Silva, N. D., Jr, Jones, L. R., and Thomas, D. D. (1999) A fluorescence energy transfer method for analyzing protein oligomeric structure: application to phospholamban. *Biophys. J.* 76, 2587-2599

33. Simmerman, H. K., Kobayashi, Y. M., Autry, J. M., and Jones, L. R. (1996) A leucine zipper stabilizes the pentameric membrane domain of phospholamban and forms a coiled-coil pore structure. *J. Biol. Chem.* 271, 5941-5946
34. Traaseth, N. J., Verardi, R., Torgersen, K. D., Karim, C. B., Thomas, D. D., and Veglia, G. (2007) Spectroscopic validation of the pentameric structure of phospholamban. *Proc. Natl. Acad. Sci. U.S.A.* 104, 14676-14681
35. Watanabe, Y., Kijima, Y., Kadoma, M., Tada, M., and Takagi, T. (1991) Molecular weight determination of phospholamban oligomer in the presence of sodium dodecyl sulfate: application of low-angle laser light scattering photometry. *J. Biochem.* 110, 40-45
36. Toyofuku, T., Kurzydlowski, K., Tada, M., and MacLennan, D. H. (1994) Amino acids Glu2 to Ile18 in the cytoplasmic domain of phospholamban are essential for functional association with the Ca(2+)-ATPase of sarcoplasmic reticulum. *J. Biol. Chem.* 269, 3088-3094
37. Gorski, P. A., Glaves, J. P., Vangheluwe, P., and Young, H. S. (2013) Sarco(endo)plasmic reticulum calcium ATPase (SERCA) inhibition by sarcolipin is encoded in its luminal tail. *J. Biol. Chem.* 288, 8456-8467
38. Gramolini, A. O., Kislinger, T., Asahi, M., Li, W., Emili, A., and MacLennan, D. H. (2004) Sarcolipin retention in the endoplasmic reticulum depends on its C-terminal RSYQY sequence and its interaction with sarco(endo) plasmic Ca(2+)-ATPases. *Proc. Natl. Acad. Sci. U.S.A.* 101, 16807-16812
39. MacLennan, D. H., Asahi, M., and Tupling, A. R. (2003) The regulation of SERCA-type pumps by phospholamban and sarcolipin. *Ann. N.Y. Acad. Sci.* 986, 472-480
40. Fajardo, V. A., Bombardier, E., Vigna, C., Devji, T., Bloemberg, D., Gamu, D., Gramolini, A. O., Quadrilatero, J., and Tupling, A. R. (2013) Co-expression of SERCA isoforms, phospholamban and sarcolipin in human skeletal muscle fibers. *PLoS One.* 8, e84304
41. Anderson, D. M., Anderson, K. M., Chang, C. L., Makarewich, C. A., Nelson, B. R., McAnally, J. R., Kasaragod, P., Shelton, J. M., Liou, J., Bassel-Duby, R., and Olson, E. N. (2015) A micropeptide encoded by a putative long noncoding RNA regulates muscle performance. *Cell.* 160, 595-606
42. Birkenmeier, C. S., White, R. A., Peters, L. L., Hall, E. J., Lux, S. E., and Barker, J. E. (1993) Complex patterns of sequence variation and multiple 5' and 3' ends are found among transcripts of the erythroid ankyrin gene. *J. Biol. Chem.* 268, 9533-9540
43. Zhou, D., Birkenmeier, C. S., Williams, M. W., Sharp, J. J., Barker, J. E., and Bloch, R. J. (1997) Small, membrane-bound, alternatively spliced forms of ankyrin 1 associated with the sarcoplasmic reticulum of mammalian skeletal muscle. *J. Cell Biol.* 136, 621-631
44. Armani, A., Galli, S., Giacomello, E., Bagnato, P., Barone, V., Rossi, D., and Sorrentino, V. (2006) Molecular interactions with obscurin are involved in the localization of muscle-specific small ankyrin1 isoforms to subcompartments of the sarcoplasmic reticulum. *Exp. Cell Res.* 312, 3546-3558
45. Porter, N. C., Resneck, W. G., O'Neill, A., Van Rossum, D. B., Stone, M. R., and Bloch, R. J. (2005) Association of small ankyrin 1 with the sarcoplasmic reticulum. *Mol. Membr. Biol.* 22, 421-432
46. Hopitzan, A. A., Baines, A. J., and Kordeli, E. (2006) Molecular evolution of ankyrin: gain of function in vertebrates by acquisition of an obscurin/titin-binding-related domain. *Mol. Biol. Evol.* 23, 46-55
47. Bagnato, P., Barone, V., Giacomello, E., Rossi, D., and Sorrentino, V. (2003) Binding of an ankyrin-1 isoform to obscurin suggests a molecular link between the sarcoplasmic reticulum and myofibrils in striated muscles. *J. Cell Biol.* 160, 245-253
48. Borzok, M. A., Catino, D. H., Nicholson, J. D., Kontrogianni-Konstantopoulos, A., and Bloch, R. J. (2007) Mapping the binding site on small ankyrin 1 for obscurin. *J. Biol. Chem.* 282, 32384-32396
49. Ackermann, M. A., Ziman, A. P., Strong, J., Zhang, Y., Hartford, A. K., Ward, C. W., Randall, W. R., Kontrogianni-Konstantopoulos, A., and Bloch, R. J. (2011) Integrity of the network sarcoplasmic reticulum in skeletal muscle requires small ankyrin 1. *J. Cell. Sci.* 124, 3619-3630
50. Kontrogianni-Konstantopoulos, A., Jones, E. M., Van Rossum, D. B., and Bloch, R. J. (2003) Obscurin is a ligand for small ankyrin 1 in skeletal muscle. *Mol. Biol. Cell.* 14, 1138-1148
51. Kontrogianni-Konstantopoulos, A., and Bloch, R. J. (2003) The hydrophilic domain of small ankyrin-1 interacts with the two N-terminal immunoglobulin domains of titin. *J. Biol. Chem.* 278, 3985-3991
52. Gokhin, D. S., and Fowler, V. M. (2011) Cytoplasmic gamma-actin and tropomodulin isoforms link to the sarcoplasmic reticulum in skeletal muscle fibers. *J. Cell Biol.* 194, 105-120
53. Kontrogianni-Konstantopoulos, A., Ackermann, M. A., Bowman, A. L., Yap, S. V., and Bloch, R. J. (2009) Muscle giants: molecular scaffolds in sarcomerogenesis. *Physiol. Rev.* 89, 1217-1267
54. Kontrogianni-Konstantopoulos, A., Catino, D. H., Strong, J. C., Randall, W. R., and Bloch, R. J. (2004) Obscurin regulates the organization of myosin into A bands. *Am. J. Physiol. Cell. Physiol.* 287, C209-17
55. Lange, S., Ouyang, K., Meyer, G., Cui, L., Cheng, H., Lieber, R. L., and Chen, J. (2009) Obscurin determines the architecture of the longitudinal sarcoplasmic reticulum. *J. Cell. Sci.* 122, 2640-2650
56. Giacomello, E., Quarta, M., Paolini, C., Squecco, R., Fusco, P., Toniolo, L., Blaauw, B., Formoso, L., Rossi, D., Birkenmeier, C., Peters, L. L., Francini, F., Protasi, F., Reggiani, C., and Sorrentino, V. (2015) Deletion of small ankyrin 1 (sAnk1) isoforms results in structural and functional alterations in aging skeletal muscle fibers. *Am. J. Physiol. Cell. Physiol.* 308, C123-38
57. Rizzo, M. A., Springer, G., Segawa, K., Zipfel, W. R., and Piston, D. W. (2006) Optimization of pairings and detection conditions for measurement of FRET between cyan and yellow fluorescent proteins. *Microsc. Microanal.* 12, 238-254
58. Markwardt, M. L., Kremers, G. J., Kraft, C. A., Ray, K., Cranfill, P. J., Wilson, K. A., Day, R. N., Wachter, R. M., Davidson, M. W., and Rizzo, M. A. (2011) An improved cerulean fluorescent protein with enhanced brightness and reduced reversible photoswitching. *PLoS One.* 6, e17896
59. Fu, M. H., and Tupling, A. R. (2009) Protective effects of Hsp70 on the structure and function of SERCA2a expressed in HEK-293 cells during heat stress. *Am. J. Physiol. Heart Circ. Physiol.* 296, H1175-83
60. Asahi, M., Kimura, Y., Kurzydlowski, K., Tada, M., and MacLennan, D. H. (1999) Transmembrane helix M6 in sarco(endo)plasmic reticulum Ca(2+)-ATPase forms a functional interaction site with phospholamban. Evidence for physical interactions at other sites. *J. Biol. Chem.* 274, 32855-32862

61. Eletr, S., and Inesi, G. (1972) Phase changes in the lipid moieties of sarcoplasmic reticulum membranes induced by temperature and protein conformational changes. *Biochim. Biophys. Acta.* 290, 178-185
62. Kosk-Kosicka, D. (2013) Measurement of Ca(2)(+)-ATPase activity (in PMCA and SERCA1). *Methods Mol. Biol.* 937, 343-356
63. Maruyama, K., and MacLennan, D. H. (1988) Mutation of aspartic acid-351, lysine-352, and lysine-515 alters the Ca2+ transport activity of the Ca2+-ATPase expressed in COS-1 cells. *Proc. Natl. Acad. Sci. U.S.A.* 85, 3314-3318
64. Lencesova, L., O'Neill, A., Resneck, W. G., Bloch, R. J., and Blaustein, M. P. (2004) Plasma membrane-cytoskeleton-endoplasmic reticulum complexes in neurons and astrocytes. *J. Biol. Chem.* 279, 2885-2893
65. Bolte, S., and Cordelieres, F. P. (2006) A guided tour into subcellular colocalization analysis in light microscopy. *J. Microsc.* 224, 213-232
66. Piston, D. W., and Rizzo, M. A. (2008) FRET by fluorescence polarization microscopy. *Methods Cell Biol.* 85, 415-430
67. Gade, P., Ramachandran, G., Maachani, U. B., Rizzo, M. A., Okada, T., Prywes, R., Cross, A. S., Mori, K., and Kalvakolanu, D. V. (2012) An IFN-gamma-stimulated ATF6-C/EBP-beta-signaling pathway critical for the expression of Death Associated Protein Kinase 1 and induction of autophagy. *Proc. Natl. Acad. Sci. U.S.A.* 109, 10316-10321
68. Rizzo, M. A., and Piston, D. W. (2005) High-contrast imaging of fluorescent protein FRET by fluorescence polarization microscopy. *Biophys. J.* 88, L14-6
69. Kontrogianni-Konstantopoulos, A., Huang, S. C., and Benz, E. J., Jr (2000) A nonerythroid isoform of protein 4.1R interacts with components of the contractile apparatus in skeletal myofibers. *Mol. Biol. Cell.* 11, 3805-3817
70. Zhang, Y. (2008) I-TASSER server for protein 3D structure prediction. *BMC Bioinformatics.* 9, 40-2105-9-40
71. Comeau, S. R., Gatchell, D. W., Vajda, S., and Camacho, C. J. (2004) ClusPro: a fully automated algorithm for protein-protein docking. *Nucleic Acids Res.* 32, W96-9
72. Comeau, S. R., Gatchell, D. W., Vajda, S., and Camacho, C. J. (2004) ClusPro: an automated docking and discrimination method for the prediction of protein complexes. *Bioinformatics.* 20, 45-50
73. Kozakov, D., Brenke, R., Comeau, S. R., and Vajda, S. (2006) PIPER: an FFT-based protein docking program with pairwise potentials. *Proteins.* 65, 392-406
74. Kozakov, D., Beglov, D., Bohnuud, T., Mottarella, S. E., Xia, B., Hall, D. R., and Vajda, S. (2013) How good is automated protein docking?. *Proteins.* 81, 2159-2166
75. Guex, N., and Peitsch, M. C. (1997) SWISS-MODEL and the Swiss-PdbViewer: an environment for comparative protein modeling. *Electrophoresis.* 18, 2714-2723
76. Bombardier, E., Smith, I. C., Vigna, C., Fajardo, V. A., and Tupling, A. R. (2013) Ablation of sarcolipin decreases the energy requirements for Ca2+ transport by sarco(endo)plasmic reticulum Ca2+-ATPases in resting skeletal muscle. *FEBS Lett.* 587, 1687-1692
77. Sahoo, S. K., Shaikh, S. A., Sopariwala, D. H., Bal, N. C., Bruhn, D. S., Kopec, W., Khandelia, H., and Periasamy, M. (2015) The N-Terminus of Sarcolipin plays an important role in uncoupling Sarco-endoplasmic Reticulum Ca2+ATPase (SERCA) ATP hydrolysis from Ca2+ transport. *J. Biol. Chem.*
78. Senes, A., Gerstein, M., and Engelman, D. M. (2000) Statistical analysis of amino acid patterns in transmembrane helices: the GxxxG motif occurs frequently and in association with beta-branched residues at neighboring positions. *J. Mol. Biol.* 296, 921-936
79. Altschul, S. F., Gish, W., Miller, W., Myers, E. W., and Lipman, D. J. (1990) Basic local alignment search tool. *J. Mol. Biol.* 215, 403-410
80. Gyorke, I., Hester, N., Jones, L. R., and Gyorke, S. (2004) The role of calsequestrin, triadin, and junctin in conferring cardiac ryanodine receptor responsiveness to luminal calcium. *Biophys. J.* 86, 2121-2128
81. Shen, X., Franzini-Armstrong, C., Lopez, J. R., Jones, L. R., Kobayashi, Y. M., Wang, Y., Kerrick, W. G., Caswell, A. H., Potter, J. D., Miller, T., Allen, P. D., and Perez, C. F. (2007) Triadins modulate intracellular Ca(2+) homeostasis but are not essential for excitation-contraction coupling in skeletal muscle. *J. Biol. Chem.* 282, 37864-37874
82. Kerr, J. P., Ward, C. W., and Bloch, R. J. (2014) Dysferlin at transverse tubules regulates Ca(2+) homeostasis in skeletal muscle. *Front. Physiol.* 5, 89
83. Abrol, N., Smolin, N., Armanious, G., Ceholski, D. K., Trieber, C. A., Young, H. S., and Robia, S. L. (2014) Phospholamban C-terminal residues are critical determinants of the structure and function of the calcium ATPase regulatory complex. *J. Biol. Chem.* 289, 25855-25866
84. Toyofuku, T., Kurzydlowski, K., Tada, M., and MacLennan, D. H. (1994) Amino acids Lys-Asp-Asp-Lys-Pro-Val402 in the Ca(2+)-ATPase of cardiac sarcoplasmic reticulum are critical for functional association with phospholamban. *J. Biol. Chem.* 269, 22929-22932
85. Toyofuku, T., Kurzydlowski, K., Tada, M., and MacLennan, D. H. (1993) Identification of regions in the Ca(2+)-ATPase of sarcoplasmic reticulum that affect functional association with phospholamban. *J. Biol. Chem.* 268, 2809-2815
86. Förster, T. (1948) Zwischenmolekulare Energiewanderung and Fluoreszenz. *Annalen der Physik.* 437, 55-75
87. Kimura, Y., Kurzydlowski, K., Tada, M., and MacLennan, D. H. (1997) Phospholamban inhibitory function is activated by depolymerization. *J. Biol. Chem.* 272, 15061-15064
88. Kimura, Y., Asahi, M., Kurzydlowski, K., Tada, M., and MacLennan, D. H. (1998) Phospholamban domain Ib mutations influence functional interactions with the Ca2+-ATPase isoform of cardiac sarcoplasmic reticulum. *J. Biol. Chem.* 273, 14238-14241
89. Green, K. N., Demuro, A., Akbari, Y., Hitt, B. D., Smith, I. F., Parker, I., and LaFerla, F. M. (2008) SERCA pump activity is physiologically regulated by presenilin and regulates amyloid beta production. *J. Cell Biol.* 181, 1107-1116
90. Honarnejad, K., and Herms, J. (2012) Presenilins: role in calcium homeostasis. *Int. J. Biochem. Cell Biol.* 44, 1983-1986
91. Yu, J. T., Chang, R. C., and Tan, L. (2009) Calcium dysregulation in Alzheimer's disease: from mechanisms to therapeutic opportunities. *Prog. Neurobiol.* 89, 240-255

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

What is claimed is:

1. A method of treating a muscular medical condition in an individual, comprising the step of providing to the individual a therapeutically effective amount of a nucleic acid composition that increases the level of small Ankyrin 1 (sAnk1) in muscle cells of the individual, wherein the medical condition comprises aberrant calcium homeostasis in muscle cells, wherein the muscular medical condition results from an insufficient level of sAnk1, and wherein the composition is a nucleic acid that comprises SEQ ID NO:1 or SEQ ID NO:3 or is at least 90, 95, 97, 98, or 99% identical to SEQ ID NO:1 or SEQ ID NO:3.

2. The method of claim 1, wherein the composition comprises an expression vector.

3. The method of claim 1, wherein the sAnk1 coding sequence is modified compared to wildtype sAnk1 sequence.

4. The method of claim 1, wherein the nucleic acid encodes a fusion protein that comprises part or all of the sAnk1 coding sequence with a fusion entity.

5. The method of claim 4, wherein the fusion entity is a label.

6. The method of claim 2, wherein the expression vector is a viral vector or a non-viral vector.

7. The method of claim 6, wherein the viral vector is an adenoviral vector, an adeno-associated viral vector, a lentiviral vector, or a retroviral vector.

8. The method of claim 1, wherein the muscle cells are heart muscle cells.

9. The method of claim 1, wherein the muscle cells are skeletal muscle cells.

10. The method of claim 1, wherein the medical condition is cardiomyopathy, muscular dystrophy, or skeletal myopathy.

11. The method of claim 1, wherein the medical condition is muscular dystrophy.

\* \* \* \* \*